US010537987B2

(12) United States Patent
Almesfer et al.

(10) Patent No.: US 10,537,987 B2
(45) Date of Patent: Jan. 21, 2020

(54) CONTROL SYSTEM FOR A MOBILITY AID

(75) Inventors: Faisal Almesfer, Auckland (NZ); Alan John Grimmer, Auckland (NZ)

(73) Assignee: REX BIONICS LIMITED, Auckland (NZ)

(*) Notice: Subject to any disclaimer, the term of this patent is extended or adjusted under 35 U.S.C. 154(b) by 1480 days.

(21) Appl. No.: 13/381,491

(22) PCT Filed: Jul. 1, 2009

(86) PCT No.: PCT/NZ2009/000130
§ 371 (c)(1),
(2), (4) Date: Mar. 23, 2012

(87) PCT Pub. No.: WO2011/002306
PCT Pub. Date: Jan. 6, 2011

(65) Prior Publication Data
US 2012/0172770 A1    Jul. 5, 2012

(51) Int. Cl.
*A61H 3/00*    (2006.01)
*B25J 9/00*    (2006.01)

(52) U.S. Cl.
CPC .................. *B25J 9/0006* (2013.01)

(58) Field of Classification Search
CPC .. A61H 3/00; A61H 2003/001; A61H 1/0262; A61H 2201/165;
(Continued)

(56) References Cited

U.S. PATENT DOCUMENTS 5,355,064 A    10/1994    Yoshino et al.
5,402,050 A *   3/1995    Ozawa ................. B62D 57/032
                                                    180/8.6
(Continued)

FOREIGN PATENT DOCUMENTS

CN    1575939    2/2005
CN    1586434    3/2005
(Continued)

OTHER PUBLICATIONS

Jacob Rosen et al., "Performances of Hill-Type and Neural Network Muscle Models—Toward a Myosignal-Based Exoskeleton," Computers and Biomedical Research, 32, 415-439 (1999), pp. 415-439.
(Continued)

*Primary Examiner* — Michael J Tsai
*Assistant Examiner* — Christopher E Miller
(74) *Attorney, Agent, or Firm* — Dann, Dorfman, Herrell and Skillman, P.C.

(57) ABSTRACT

A control system for controlling an exoskeleton worn by a user and having one or more actuators associated with various body members of the exoskeleton each corresponding to a body part of the user. The control system comprises a user interface for receiving input data indicative of a desired movement sequence, a memory component for storing pre-programmed movement data indicative of one or more sequential instructions required to effect the movement sequence, each instruction being associated with relative actuator movements for performing the instruction, and an actuator controller for moving the one or more actuators according to the relative actuator movements for each instruction. The control system also comprises a terrain sub-system for adjusting the actuator movements upon detection of a change in terrain slope and a balance control sub-system for periodically adjusting the balance of the exoskeleton during relative movement of the one or more actuators.

23 Claims, 59 Drawing Sheets

(58) Field of Classification Search
CPC .... A61H 2201/5058; A61H 2201/5061; A61H 2201/5064; A61H 2201/5069; A61H 2201/5071; A61H 2201/5084; A61B 5/04888; B25J 9/0006; B62D 57/02; B62D 57/024; B62D 57/032; G05D 2201/0217
USPC .............. 700/245, 250, 253, 254, 256, 258; 318/568.12, 568.16, 568.17, 568.18, 318/568.22, 568.24
See application file for complete search history.

(56) References Cited

U.S. PATENT DOCUMENTS

| | | | | |
|---|---|---|---|---|
| 5,404,086 | A * | 4/1995 | Takenaka | B62D 57/032 318/568.11 |
| 5,432,417 | A * | 7/1995 | Takenaka | B62D 57/032 180/8.6 |
| 5,974,366 | A * | 10/1999 | Kawai | B62D 57/032 318/568.12 |
| 6,177,776 | B1 * | 1/2001 | Kawai | B25J 13/085 180/8.1 |
| 6,943,520 | B2 | 9/2005 | Furuta et al. | |
| 7,190,141 | B1 | 3/2007 | Ashrafiuon et al. | |
| 7,313,463 | B2 | 12/2007 | Herr et al. | |
| 7,390,309 | B2 | 6/2008 | Dariush | |
| 7,402,142 | B2 | 7/2008 | Kawai et al. | |
| 7,431,737 | B2 | 10/2008 | Ragnarsdottir et al. | |
| 7,530,410 | B2 * | 5/2009 | Takenaka | B25J 19/0091 180/6.5 |
| 7,561,941 | B2 * | 7/2009 | Kwon | A63H 11/00 180/8.2 |
| 7,650,203 | B2 * | 1/2010 | Maslov | B25J 13/085 180/8.5 |
| 7,756,605 | B2 * | 7/2010 | Hirose | B25J 13/085 700/245 |
| 2005/0029979 | A1 | 2/2005 | Lee et al. | |
| 2005/0049748 | A1 * | 3/2005 | Lee | B62D 57/032 700/245 |
| 2005/0171635 | A1 * | 8/2005 | Furuta | B62D 57/032 700/245 |
| 2005/0192677 | A1 * | 9/2005 | Ragnarsdottir | A61F 2/66 623/24 |
| 2005/0234593 | A1 | 10/2005 | Goswami et al. | |
| 2006/0106495 | A1 * | 5/2006 | Takenaka | B62D 57/032 700/253 |
| 2006/0173578 | A1 * | 8/2006 | Takenaka | B62D 57/032 700/245 |
| 2006/0211956 | A1 * | 9/2006 | Sankai | A61B 5/04888 601/5 |
| 2006/0224247 | A1 * | 10/2006 | Clausen | A61F 2/66 623/24 |
| 2006/0276728 | A1 * | 12/2006 | Ashihara | A61F 5/0102 601/5 |
| 2007/0050045 | A1 * | 3/2007 | Clausen | A61F 2/66 623/24 |
| 2007/0050047 | A1 * | 3/2007 | Ragnarsdottlr | A61F 2/68 623/24 |
| 2007/0054777 | A1 * | 3/2007 | Kawai | A61H 3/00 482/1 |
| 2007/0056592 | A1 * | 3/2007 | Angold | A61H 3/00 128/845 |
| 2007/0145930 | A1 * | 6/2007 | Zaier | B62D 57/032 318/568.12 |
| 2007/0156252 | A1 | 7/2007 | Jonsson et al. | |
| 2007/0162152 | A1 | 7/2007 | Herr et al. | |
| 2008/0161937 | A1 * | 7/2008 | Sankai | A61H 3/008 623/25 |
| 2008/0188985 | A1 | 8/2008 | Sakano | |
| 2008/0234608 | A1 * | 9/2008 | Sankai | A61B 5/04888 601/5 |
| 2008/0310705 | A1 * | 12/2008 | Asatani | B62D 57/032 382/153 |
| 2009/0030530 | A1 * | 1/2009 | Martin | A61F 2/6607 623/53 |
| 2009/0036815 | A1 * | 2/2009 | Ido | A61H 1/0237 602/23 |
| 2009/0099689 | A1 * | 4/2009 | Takenaka | B62D 57/032 700/245 |
| 2009/0222105 | A1 * | 9/2009 | Clausen | A61F 2/60 623/27 |
| 2009/0271037 | A1 * | 10/2009 | Hong | B62D 57/032 700/253 |
| 2009/0292369 | A1 * | 11/2009 | Kazerooni | A61H 3/00 623/27 |
| 2009/0306824 | A1 * | 12/2009 | Zaier | B62D 57/032 700/250 |
| 2010/0094188 | A1 * | 4/2010 | Goffer | B25J 9/0006 602/23 |
| 2010/0113980 | A1 * | 5/2010 | Herr | A61F 2/60 600/587 |
| 2010/0114329 | A1 * | 5/2010 | Casler | B25J 19/0008 623/24 |
| 2010/0126785 | A1 * | 5/2010 | Shimada | B62D 57/032 180/8.1 |
| 2010/0262044 | A1 * | 10/2010 | Siegler | A61B 5/1036 600/592 |
| 2010/0305478 | A1 * | 12/2010 | Ordway | A61B 5/1038 600/587 |
| 2011/0066088 | A1 * | 3/2011 | Little | B25J 9/0006 601/35 |
| 2011/0257764 | A1 * | 10/2011 | Herr | A61F 2/60 623/24 |

FOREIGN PATENT DOCUMENTS

| | | |
|---|---|---|
| CN | 1929797 | 3/2007 |
| EP | 1260201 | 11/2002 |
| EP | 1442703 | 8/2004 |
| EP | 1661543 | 5/2006 |
| EP | 1723941 | 11/2006 |
| EP | 1842518 | 10/2007 |
| WO | 2006113520 | 10/2006 |
| WO | 2008048658 | 4/2008 |
| WO | 2009051574 | 4/2009 |
| WO | 2009078499 | 6/2009 |

OTHER PUBLICATIONS

Jan F. Veneman et al., "Design and Evaluation of the LOPES Exoskeleton Robot for Interactive Gait Rehabilitation," IEEE Transactions on Neural Systems and Rehabilitation Engineering, vol. 15, No. 3, Sep. 2007, pp. 379-386.

AU Pat. Appln. No. 2009348961, Patent Examination Report No. 1, IP Australia, dated Jul. 23, 2013, pp. 1-4.

AU Pat. Appln. No. 2015201084, Patent Examination Report No. 1, IP Australia, dated Apr. 27, pp. 1-3.

* cited by examiner

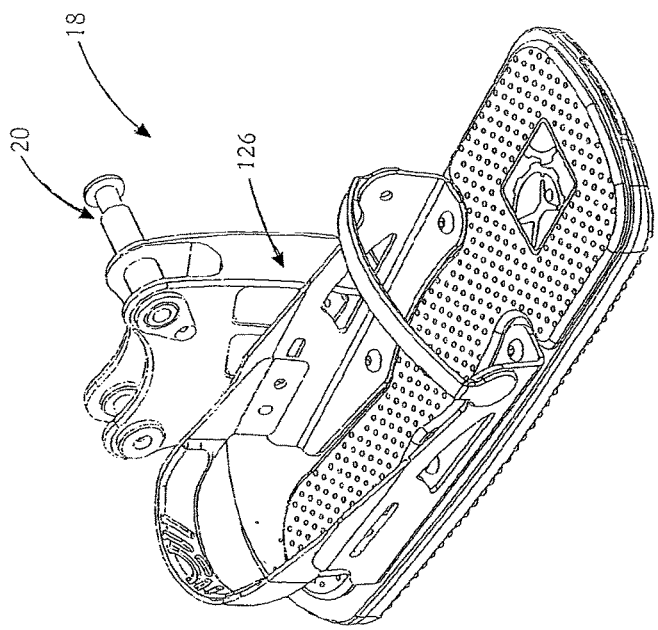
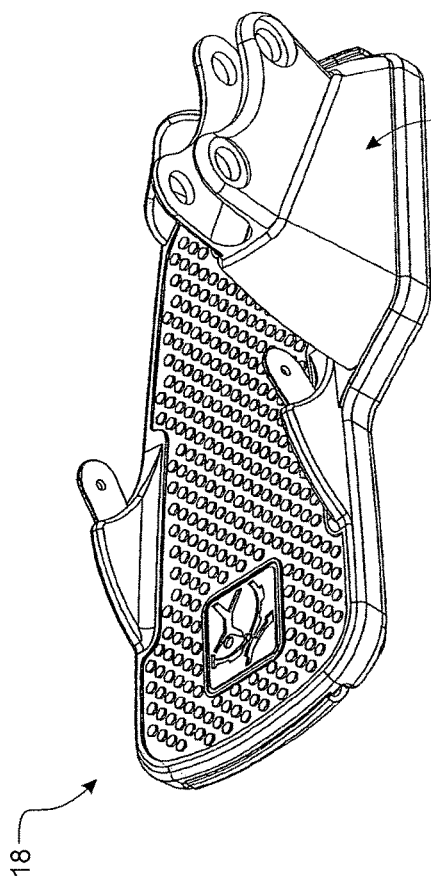
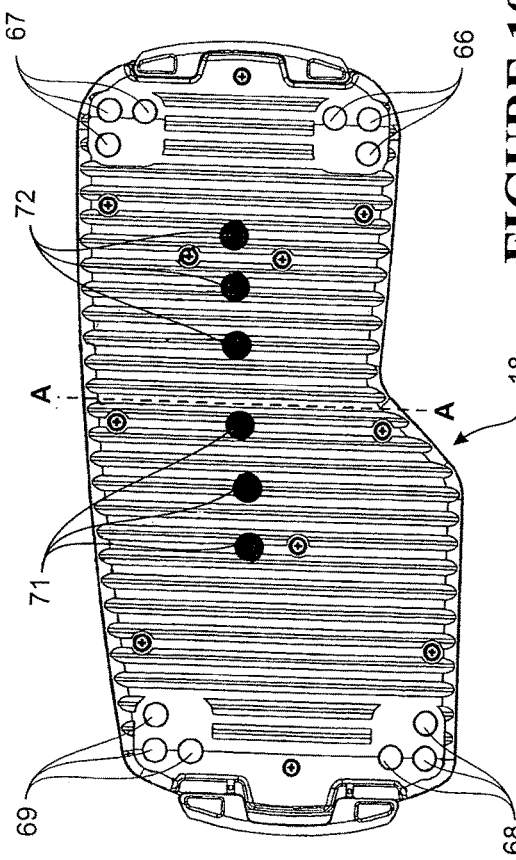
FIGURE 11
FIGURE 9
FIGURE 10

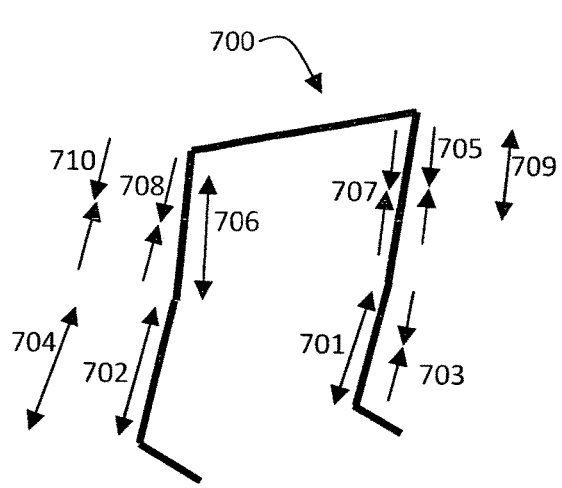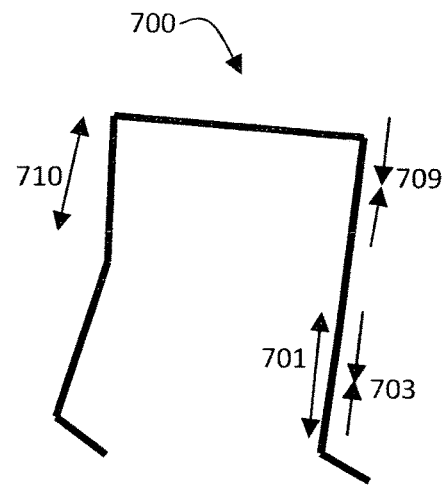
FIGURE 45a                 FIGURE 45b
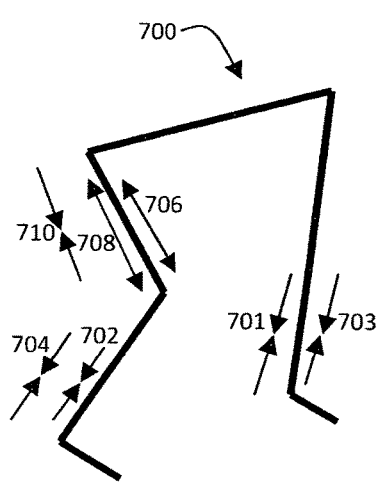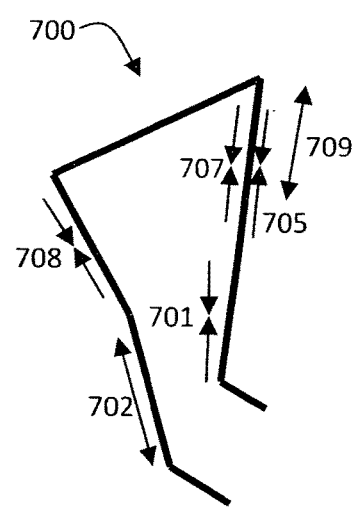
FIGURE 45c                 FIGURE 45d

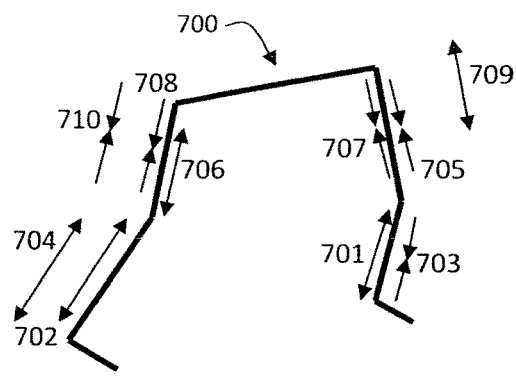
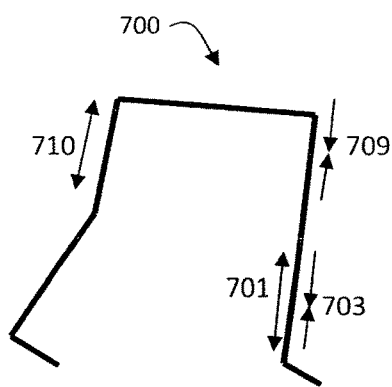
FIGURE 46a  FIGURE 46b
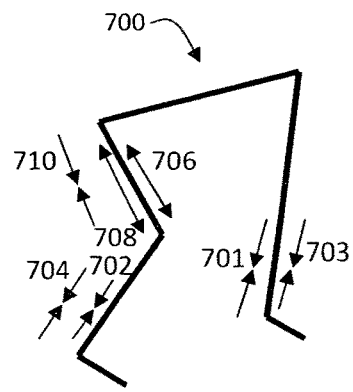
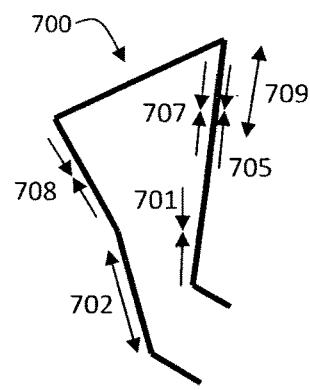
FIGURE 46c  FIGURE 46d
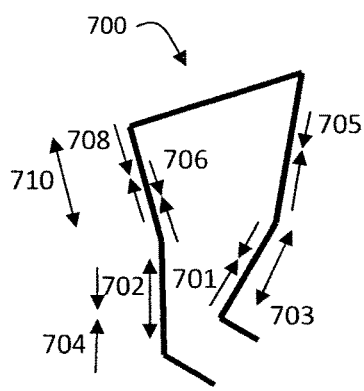
FIGURE 46e

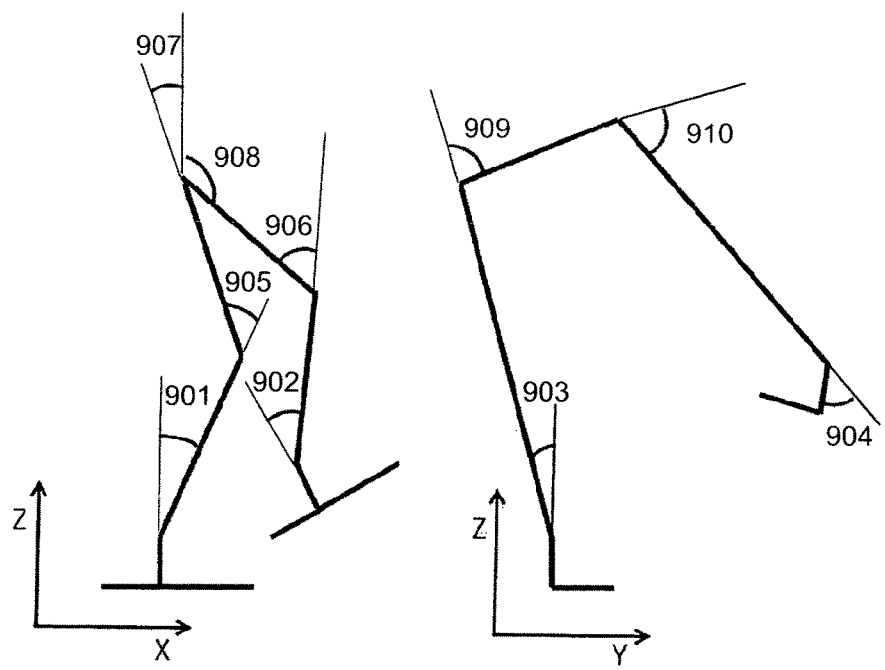
FIGURE 52a  FIGURE 52b
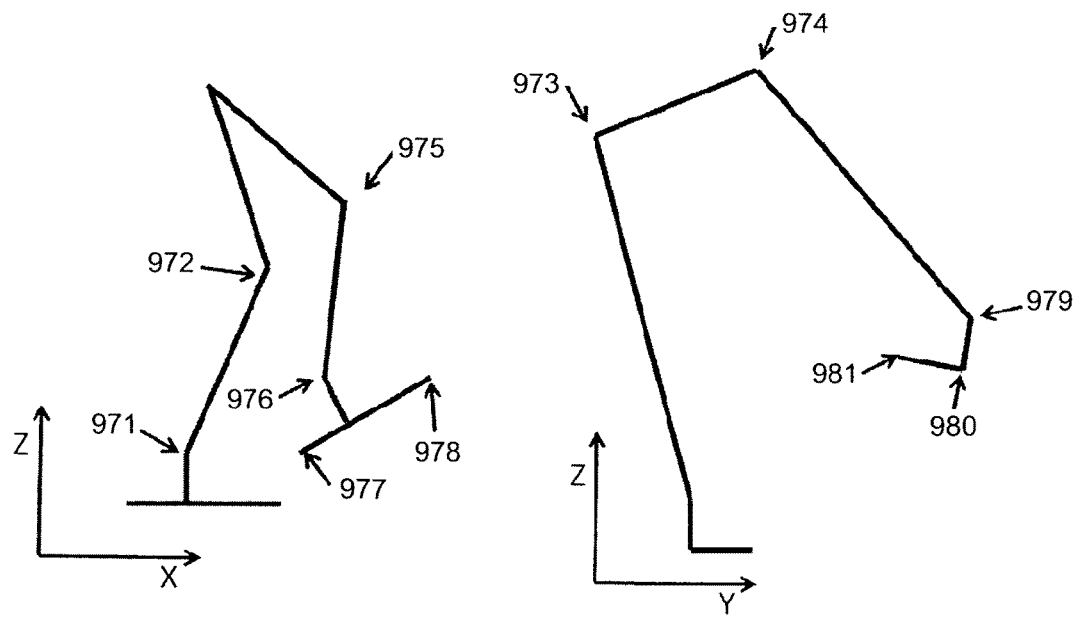
FIGURE 53a  FIGURE 53b

CONTROL SYSTEM FOR A MOBILITY AID

FIELD OF THE INVENTION

The present invention relates to control system for a mobility aid or walking aid (WA) that is suitable for supporting a mobility impaired disabled user.

BACKGROUND TO THE INVENTION

Mobility impaired people, such as those suffering from paraplegia, are often confined to a wheelchair and this serves as their only means of mobility. The extent of mobility provided by a wheelchair is limited. In addition, being confined for long periods to a wheelchair causes health problems.

To prevent such health problems, various training systems have been developed to help a mobility impaired person exercise their lower limbs to assist in muscle mass retention and increase circulation. Some such training systems comprise non-motorised brace systems that are worn by the user to help them perform locomotive exercises.

More recently, motorised or powered bracing systems, walking aids, and gait-locomotor apparatuses have been proposed to assist a mobility impaired person perform daily functional locomotive activities, such as walking. Such systems typically comprise an exoskeleton that is attached to the user and which includes leg sections having corresponding thigh, shin and foot portions that are connected with hip, knee and ankle joints. Actuators are provided for moving the thigh, shin and foot portions of the leg sections and the actuators may be operated by a joystick or other control system to effect a human gait. Such systems encounter stability problems, especially when moving across uneven terrain and when they encounter other external disturbances, including movement of the user's upper body relative to the exoskeleton. To assist with stability, the user is typically required to use crutches in combination with such powered walking aids.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide a stable walking aid that is capable of fully supporting the user when in motion, or to at least provide the public with a useful choice.

SUMMARY OF THE INVENTION

In a first aspect the invention may broadly be said to consist of a method for controlling an exoskeleton worn by a user and having one or more actuators associated with various body members of the exoskeleton each corresponding to a body part of the user, the method comprising the steps of: receiving input data indicative of a desired movement sequence; obtaining from memory pre-programmed movement data indicative of one or more sequential instructions comprising at least a landing foot instruction required to effect the movement sequence, each instruction being associated with relative actuator movements for performing the instruction; moving the one or more actuators according to the relative actuator movements for each instruction; and adjusting the landing foot instruction upon receiving data indicative of a change in terrain slope, the step of adjusting comprising: moving one or more actuators associated with a landing foot member of the exoskeleton to pivot the foot member towards a maximum allowable slope angle; and terminating movement of the one or more actuators associated with the foot member upon receiving input indicative of alignment of the foot member with the slope.

Preferably the foot member comprises at least one contact sensor at every corner region of an underside of the foot member and wherein the corner regions form two pairs of substantially aligned corner regions in a transverse direction and two pairs of substantially aligned corner regions in a longitudinal direction.

Preferably the contact sensor is a tactile sensor. Alternatively the contact sensor is a pressure sensor.

Preferably the data indicative of the change in terrain slope is received when a trigger signal is received from the sensor or sensors of only some of the corner regions upon contact of the underside of the landing foot member with the terrain.

Preferably the terrain slope consists of a longitudinal component and a transverse component, and data indicative of a change in terrain slope indicates a change in the longitudinal component of the terrain slope or a change in the transverse component of the terrain slope or both.

Preferably the maximum allowable slope angle is either a maximum allowable angle between the slope and a longitudinally extending and substantially horizontal line, or a maximum allowable transverse angle between the slope and a transversely extending and substantially horizontal line.

Preferably receiving a trigger signal from at least one contact sensor associated with only one of the two pairs of transversely aligned corner regions indicates a change in the longitudinal component of the terrain slope, and receiving a trigger signal from at least one contact sensor associated with only one of the two pairs of longitudinally aligned corner regions indicates a change in the transverse component of the terrain slope.

Preferably the step of moving one or more actuators associated with a landing foot member of the exoskeleton to pivot the foot member towards a maximum allowable slope angle comprises pivoting the foot member about an axis traversing through the pair of aligned corner regions from which a trigger signal is received.

Preferably the step of terminating movement of the one or more actuators comprises terminating the movement upon receiving a trigger signal from at least one sensor associated with an opposing pair of aligned corner regions to the pair through which the pivot axis traverses indicating alignment of the foot member with the slope of the terrain.

Preferably the maximum allowable slope angle is predetermined and stored in memory.

Preferably the method further comprises the step of halting movement of the one or more actuators upon receiving the data indicative of a change in terrain slope.

Preferably the method further comprises after the step of terminating movement of the one or more actuators, the step of storing terrain state data indicative of a current slope of the terrain.

Preferably the step of storing terrain state data indicative of a current slope of the terrain comprises: averaging an angle of the foot member and input data from an accelerometer associated with the foot member; and storing the averaged angle as the data indicative of the current slope of the terrain.

Preferably the method further comprising prior to moving the one or more actuators and after obtaining the pre-programmed movement data, the step of updating the relative actuator movements according to stored terrain state data indicative of the slope of the terrain.

Preferably moving each actuator comprises changing a length of the actuator and wherein changing the length of an actuator alters an angle of an associated joint formed between body members of the exoskeleton.

Preferably for the embodiment above, the step of moving the one or more actuators associated with the landing foot member to pivot the foot member towards a maximum allowable slope angle comprises the steps of: identifying a pivot axis and a pivot direction required to align the foot member with the slope of the terrain; obtaining from the length of each actuator the angle of the associated joint or joints; calculating a relative position of a foot joint of the exoskeleton associated with the required pivot axis and pivot direction using the angle of the foot joint; determining a desired position of the foot joint associated with the landing foot member required to effect a pivot of the foot member to a maximum allowable slope angle; using inverse kinematics to determine a desired position of each joint affecting a position of the foot joint; determining a desired joint angle from the desired positions of the joints affecting the position of the foot joint; determining a desired change in length of each actuator associated with each desired joint angle; and changing the length of each actuator associated with each desired joint angle towards the desired change in length of the actuator.

Preferably the step of using inverse kinematics comprises using a method of intersecting circles to determine a desired position of joints affecting the position of the foot joint.

Preferably the foot member comprises two middle region contact sensors for providing information regarding a state of contact of central front and back regions of the foot member with the terrain to provide increased resolution as to the alignment of the foot member with the terrain.

In a second aspect the invention may broadly be said to consist of a method for controlling an exoskeleton worn by a user and having one or more actuators associated with various body members of the exoskeleton each corresponding to a body part of the user, the method comprising the steps of: receiving input data indicative of a desired movement sequence; obtaining from memory pre-programmed movement data indicative of one or more sequential instructions required to effect the movement sequence, each instruction being associated with relative actuator movements for performing the instruction; updating the relative actuator movements according to stored adjustment data indicative of a current terrain state; and moving the one or more actuators according to the updated relative actuator movements for each instruction.

In a third aspect the invention may broadly be said to consist of a method for controlling an exoskeleton worn by a user and having one or more actuators associated with at least a foot member of the exoskeleton corresponding to a foot of the user to adjust the foot member to a change in terrain slope, the method comprising the steps of: receiving data indicative of a change in terrain slope during a landing instruction associated with the foot member; moving one or more actuators associated with the foot member to pivot the foot member towards a maximum allowable slope angle; and terminating movement of the one or more actuators associated with the foot member upon receiving input indicative of alignment of the foot member with the slope.

In a fourth aspect the invention may broadly be said to consist of a method for controlling an exoskeleton worn by a user and having one or more actuators associated with various body members of the exoskeleton each corresponding to a body part of the user, the method comprising the steps of: receiving input data indicative of a desired movement sequence; obtaining from memory pre-programmed movement data indicative of one or more sequential instructions required to effect the movement sequence, each instruction being associated with relative actuator movements for performing the instruction; moving the one or more actuators according to the relative actuator movements for each instruction; and periodically balancing the exoskeleton during movement of the one or more actuators according to a current instruction by: determining an actual centre of pressure location at an underside of at least one grounded foot member of the exoskeleton based on input pressure data indicative of pressure at one or more regions of the foot, obtaining a desired centre of pressure location associated with a current instruction to which the one or more actuators move according to, and moving one or more actuators associated with an orientation of the grounded foot member to a position which shifts the actual centre of pressure under the foot towards the desired centre of pressure for the current instruction.

Preferably the step of periodically balancing the exoskeleton occurs at predetermined time steps during the current instruction.

Preferably the step of periodically balancing the exoskeleton further comprises: determining a centre of pressure error between the actual centre of pressure location and a desired centre of pressure location for a current time step; determining a desired actuator position for a subsequent time step for each actuator associated with the orientation of the grounded foot member; adjusting the desired actuator position for the subsequent time step based on the error for each actuator; and moving each actuator towards the adjusted actuator position during the subsequent time step.

Preferably the desired centre of pressure location for a current time step is determined at a previous time step by: interpolating between an actual centre of pressure location at the previous time step and the desired centre of pressure location for the instruction; and determining from the interpolation a desired centre of pressure location for a subsequent time step.

Preferably the step of determining a desired actuator position for a subsequent time step comprises: interpolating between an actual actuator position and a desired actuator position resulting from a completed actuator movement for the current instruction; and determining from the interpolation the desired actuator position for the subsequent time step.

Preferably the step of adjusting the desired actuator position for the subsequent time step comprises: determining a change in actuator position using the centre of pressure error; and adding the change in actuator position to the desired actuator position for the subsequent time step to adjust the desired actuator position for the subsequent time step.

Preferably the step of determining a change in actuator position using the centre of pressure error is achieved by feeding the error into a proportional integral derivative (PID) controller arranged to output an indication of the change in actuator position.

Preferably moving the one or more actuators comprises changing the length of the one or more actuators.

Preferably each grounded foot member comprises at least one pressure sensor at four corners of the underside of the grounded foot.

Preferably determining the actual centre of pressure location comprises the steps of: dividing a rectangular region defined by the four corners of the underside of the foot into two large triangles; determining the centroid location for each of the large triangles using the pressure sensor inputs; forming an inner triangle within each large triangle and about the associated centroid of the large triangle using the centroid location and the pressure sensor inputs; determining the centroid location for each inner triangle; and determining the actual centre of pressure location using the pressure sensor inputs and the centroids of the inner triangles.

In a fifth aspect the invention may broadly be said to consist of a method for balancing an exoskeleton worn by a user during relative movement of one or more actuators of the exoskeleton to perform a predetermined instruction, the method for balancing comprising the steps of: calculating an actual centre of pressure under at least one grounded foot of the exoskeleton based on input pressure data indicative of pressure at one or more regions of the foot, determining a centre of pressure error between the actual centre of pressure and a desired centre of pressure for the predetermined instruction, and moving the one or more actuator to negate the centre of pressure error by shifting the actual centre of pressure under the foot towards the desired centre of pressure for the predetermined instruction.

In a sixth aspect the invention may broadly be said to consist of a control system for controlling an exoskeleton worn by a user and having one or more actuators associated with various body members of the exoskeleton each corresponding to a body part of the user, the control system comprising: a user interface for receiving input data indicative of a desired movement sequence, a memory component for storing pre-programmed movement data indicative of one or more sequential instructions required to effect the movement sequence, each instruction being associated with relative actuator movements for performing the instruction, an actuator controller for moving the one or more actuators according to the relative actuator movements for each instruction, a terrain sub-system for adjusting the actuator movements upon detection of a change in terrain slope, and a balance control sub-system for periodically adjusting the balance of the exoskeleton during relative movement of the one or more actuators.

Preferably the control system receives input from four contact sensors arranged at four corner regions of an underside of a foot member of the exoskeleton to detect a change in terrain slope.

Preferably the terrain subsystem is arranged to: determine a movement of one or more actuators associated with a foot member of the exoskeleton required to pivot the foot member towards a maximum allowable slope angle, and terminate movement of the one or more actuators associated with the foot member upon receiving input indicative of alignment of the foot member with the slope.

Preferably the balance control sub-system receives input from four pressure sensors arranged at four corner regions of an underside of a foot member of the exoskeleton.

Preferably the pressure sensor inputs enable the balance control sub-system to determine a location of the centre of pressure at the underside of the foot to thereby determine a required adjustment of the actuator movements to shift the location of the centre of pressure towards a desired centre of pressure location for a particular instruction.

In an embodiment the control system preferably receives input from two middle region contact sensors of a foot member for providing information regarding a state of contact of central front and back regions of the foot member with a terrain to provide increased resolution as to the alignment of the foot member with the terrain.

In a seventh aspect the invention may broadly be said to consist of a control system for controlling an exoskeleton worn by a user and having one or more actuators associated with various body members of the exoskeleton each corresponding to a body part of the user, the control system comprising: a user interface for receiving input data indicative of a desired movement sequence; a memory component for storing pre-programmed movement data indicative of one or more sequential instructions required to effect the movement sequence, each instruction being associated with relative actuator movements for performing the instruction; an actuator controller for moving the one or more actuators according to the relative actuator movements for each instruction; and a terrain sub-system for adjusting the actuator movements upon detection of a change in terrain slope.

In an eighth aspect the invention may broadly be said to consist of a control system for controlling an exoskeleton worn by a user and having one or more actuators associated with various body members of the exoskeleton each corresponding to a body part of the user, the control system comprising: a user interface for receiving input data indicative of a desired movement sequence; a memory component for storing pre-programmed movement data indicative of one or more sequential instructions required to effect the movement sequence, each instruction being associated with relative actuator movements for performing the instruction; an actuator controller for moving the one or more actuators according to the relative actuator movements for each instruction; and a balance control sub-system for periodically adjusting the balance of the exoskeleton during relative movement of the one or more actuators.

Preferably the exoskeleton comprises: a rigid pelvic support member including a user securing arrangement for fastening a user to at least the pelvic support member to support said user operationally; a first leg structure and a second leg structure, each of the first leg structure and the second leg structure being coupled to and extending from said pelvic support member for operational location adjacent a respective leg of a user, each of the first leg structure and second leg structure comprising: an upper leg structural member for engagement with the upper leg of the user, the upper leg structural member being pivotally engaged at a first end thereof to the pelvic support member by a hip joint; a lower leg structural member for engagement with the lower leg of the user, the lower leg structural member being pivotally engaged at a first end thereof to a second end of the upper leg structural member by a knee joint; a foot member for engagement with the foot of a user, the foot member being pivotally engaged to a second end of the lower leg member by a foot joint; a main hip actuator configured for actuating rotation of said upper leg structural member relative to said pelvic support member about said hip joint, to in use pivot the upper leg structural member in an anterior/posterior plane; a knee actuator configured for actuating rotation of said lower leg structural member relative said upper leg structural member about said knee joint; and a main foot actuator configured for actuating rotation of said foot member relative said lower leg structural member about said foot joint about an axis of rotation substantially parallel to the axis of rotation of the knee joint; and a power source configurable for providing power to at least one or more selected from said main hip actuators, knee actuators, and main foot actuators.

The term "anterior" as used in this specification and claims relates to a direction corresponding to the front or in front of a human user, and the term "anteriorly" is to be construed accordingly.

The term "posterior" as used in this specification and claims relates to a direction corresponding to the back of or behind a human user, and the term "posteriorly" is to be construed accordingly.

The phrase "anterior/posterior plane" as used in this specification and claims relates to a plane extending anteriorly and/or posteriorly from a user.

The term "medial" as used in this specification and claims relates to a direction extending inwardly towards a user's body from the user's inner arm, and the term "medially" is to be construed accordingly.

The term "lateral" as used in this specification and claims relates to a direction extending outwardly sideways from a user's body, and the term "laterally" is to be construed accordingly.

The phrase "medial/lateral plane" as used in this specification and claims relates to a plane extending medially and/or laterally from a user.

As used herein the term "and/or" means "and" or "or", or both.

As used herein "(s)" following a noun means the plural and/or singular forms of the noun.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

BRIEF DESCRIPTION OF THE DRAWINGS

Preferred embodiments of the invention will be described by way of example only and with reference to the drawings, in which:

FIG. 9 shows a left side perspective view of a foot member;

FIG. 10 shows a boot view of the foot member of FIG. 9;

FIG. 11 shows a right side perspective view of a foot member;

FIG. 36 shows a side view of a third embodiment of the WA in a standing position without covers on;

FIG. 37 shows a side view of a third embodiment of the WA in a stepping position without covers on;

FIG. 38 shows a side view of a third embodiment of the WA in a stepping position with covers on;

FIG. 39 shows a front perspective view of the third embodiment of the WA in a sitting position without covers on;

FIG. 40 shows a front view of the third embodiment of the WA in a sitting position without covers on;

FIGS. 45*a*-45*j* show a model of the exoskeleton undergoing a static step movement sequence in accordance with a preferred form of the control system of the WA;

FIGS. 46*a*-46*e* show the model of the exoskeleton undergoing a left dynamic step movement sequence in accordance with a preferred form of the control system of the WA;

FIGS. 52*a* and 52*b* show reference joint angles for a model of the exoskeleton employed in the terrain subsystem;

FIGS. 53*a* and 53*b* show body point reference locations of the exoskeleton model to be calculated by the terrain sub-system;

DETAILED DESCRIPTION OF PREFERRED EMBODIMENTS

Figure 1:
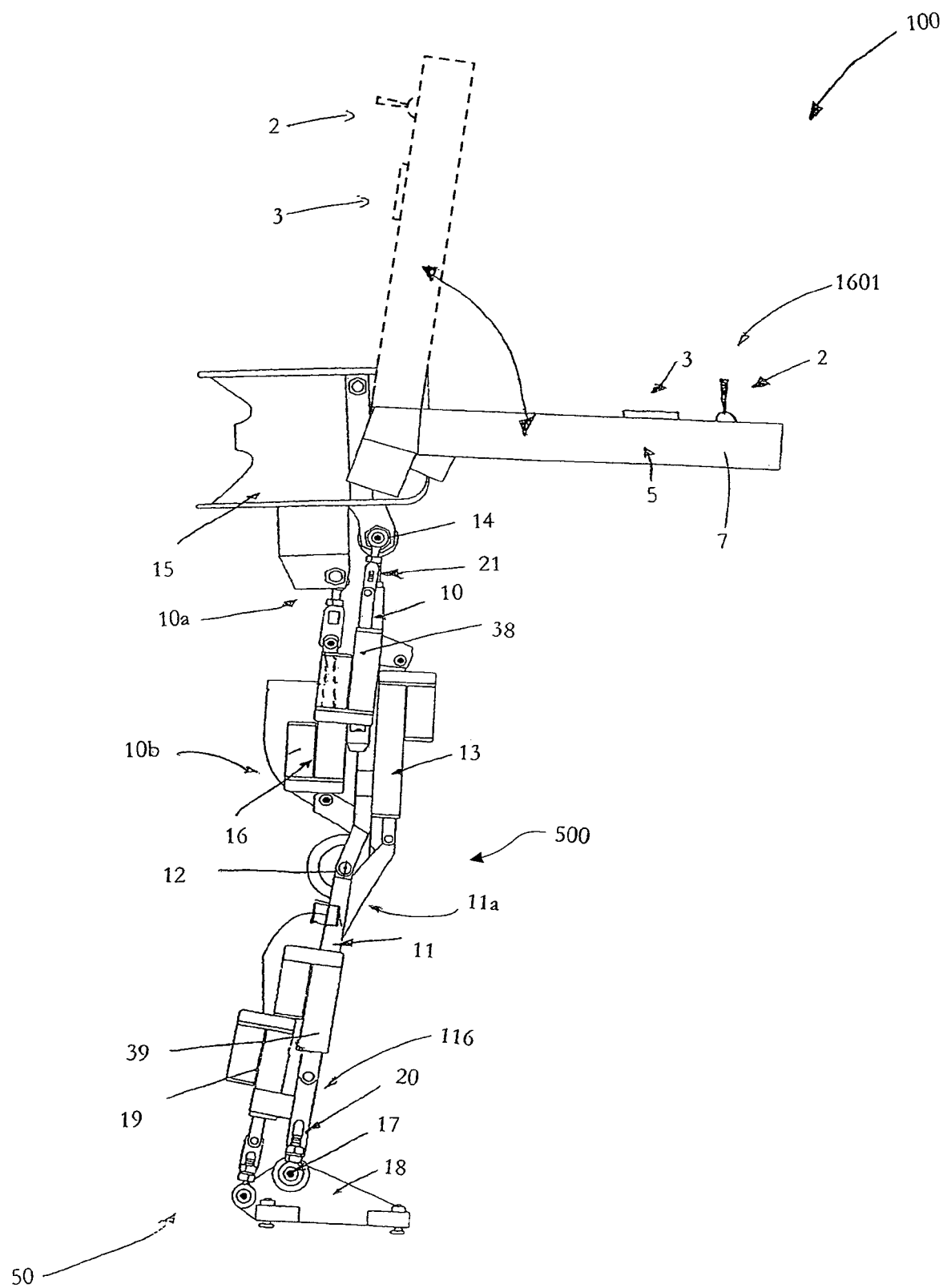
FIG. 1 shows a side view of the exoskeleton forming part of the WA with orthotics provided, shown in a first embodiment without a secondary hip actuator.

With reference to the above drawings, in which similar features are generally indicated by similar numerals, a device that may in one form be a walking aid (WA) is generally indicated by the numeral 100, and an exoskeleton suitable for use in a controllable walking aid is generally indicated by the numeral 500. The phrases walking aid and mobility aid are used interchangeably in this specification. The device may also in another form be considered a medical device that can assist in reducing adverse effects of immobility of the leg or legs of a mobility impaired disabled user, whether the device is also able to move the user in a walking or stepping manner or not.

The mechanical structure of the preferred embodiments of the WA is detailed below with reference to FIGS. 1-44. Following this, preferred forms of the control system of the WA are described with reference to FIGS. 45*a*-73.

Mechanical Structure of WA

With reference to FIGS. 1-44, the WA 100 is suitable for supporting a mobility impaired disabled user while moving through a set of movements correlating to a walking motion. The WA 100 comprises an exoskeleton 500, a power source in the form of a battery pack or other similar onboard power pack (not shown) together with its associated power supply cables (not shown), and a control system (not shown).

The exoskeleton 500 comprises a rigid pelvic support member or hip frame 15 including a pelvic harness 96, and a pair of leg structures 50 (a first leg structure and second leg structure). The hip frame 15 is required to be of a relatively low weight, while having a high rigidity and low amounts of flexing in operation. For this reason, the hip frame 15 is moulded from carbon fibre as a single unit having an interior hollow space (not shown). It is envisaged that the hip frame 15 could also be moulded from glass fibre. The hip frame 15 further includes transverse shear webs extending across its interior hollow space.

Each of the leg structures 50 comprise an upper leg structural member 10, a lower leg structural member 11, a foot member 18, a main hip actuator 16, a knee actuator 13 and a main foot actuator 19. The upper leg structural member 10 is for securing with an upper leg 610 of a user 600, the upper leg structural member 10 being pivotally engaged at a first end 10*a* thereof to the hip frame 15 by the hip joint 14. The lower leg structural member 11 is for securing with the lower leg 620 of the user 600, the lower leg structural member 11 being pivotally engaged at a first end 11*a* thereof to a second end 10*b* of the upper leg structural member 10 by a knee joint 12.

In one embodiment, it is envisaged that the knee joint 12 will only allow relative pivotal movement between the upper leg structural member 10 and the lower leg structural member 11 along a single plane. It will preferably use a roller bearing arrangement (not shown) to accomplish this. However, the knee joint 12 may be subject to large twisting forces or sideways forces, causing axial forces on the roller bearing arrangement. For this reason, it is envisaged that the knee joint will also include a thrust bearing arrangement (not shown) configured for resisting axial forces on the knee joint 12.

Each of said upper leg structural member 10 and lower leg structural member 11 include a fastening arrangement in the form of adjustable fasteners 46 for fastening the respective leg structures 50 to the associated legs of a user 600 in use. It is envisaged that the fasteners 46 may be comprised of flexible webbing or straps, and can include an adjustable fastening arrangement 47, which could be in the form of straps having a hook and loop fastening system such as Velcro® which pass through a buckle. Alternately, the adjustable fastening arrangement can include a typical buckle, ratchet buckle or catch formation.

The foot member 18 is for securing to the foot 630 of a user 600, the foot member 18 being pivotally engaged to a second end 11*b* of the lower leg structural member 11 by a foot joint 17. Each of said foot members 18 includes a foot member structural component 126 for guiding the movement of a user's feet 630 operationally.

In one embodiment, each of said foot members 18 includes a shoe 31 which is removably engageable with the foot member structural component 126, and into which the user 600 can place their feet. The shoe 31 is conveniently removably engageable with the foot member structural component 126 by means of a securing formation, such as a clip-type formation, a snap-fit type formation, a bayonet-type formation or any other suitable formation. The position of the shoe 31 relative to the foot member structural component 126 is envisaged as being adjustable, to allow the alignment of a user's ankle with the axis of rotation 17A of the foot joint 17.

In another embodiment, each of the foot members 18 include a foot engaging formation 34 for engaging indirectly (i.e. the user wearing shoes) with a user's foot 630. The foot engaging formation 34 is coupled to the foot member structural component 126 in an adjustable manner, to again allow for positioning of the user's 600 ankle.

The main hip actuator 16 is configured for actuating rotation of said upper leg structural member 10 relative to said hip frame 15 about said hip joint 14, to thereby (in use) pivot the upper leg structural member 10 in an anterior/posterior plane of the user 600.

The exoskeleton 500 further includes, for each of the leg structures 50, a secondary hip actuator 38. The secondary hip actuator 38 is configured for actuating rotation of the upper leg structural member 10 in a medial/lateral plane about the hip frame 15 and relative to the user 600 in use.

In a preferred embodiment, the secondary hip actuator 38 is configured for actuating rotation of said upper leg structural member 10 in a medial/lateral plane in a range of about 29 degrees, and more preferably about 11 degrees inwardly and 18 degrees outwardly. In alternative embodiments the range could be limited to less than 29 degrees and/or divided into an inwards and outwards component appropriately as required by the particular application.

The knee actuator 13 is configured for actuating rotation of said lower leg structural member 11 relative said upper leg structural member 10 about said knee joint 12.

The main foot actuator 19 is configured for actuating rotation of said foot member 18 relative said lower leg structural member 11 about said foot joint 17 about an axis of rotation 17A substantially parallel to the axis of rotation 12A of the knee joint 12.

Further, the exoskeleton 500 includes, for each of the leg structures 50, a secondary foot actuator 39. The secondary foot actuator 39 is configured for actuating rotation of said foot member 18 in a substantially medial/lateral plane about said foot joint 17. Each secondary foot actuator 39 is configured for actuating rotation of its associated upper leg structural members 10 in medial/lateral plane in a range of about ten degrees, and more preferably about six degrees to either side of vertical.

The power source is configurable for providing power to the actuators 16, 13, 19, 38, 39.

As will be explained later, the control system is configurable for controlling movement of the main hip actuators, secondary hip actuators, knee actuators, main foot actuators, and secondary foot actuators. This will cause movement of the exoskeleton 500 relative to the ground on which the walking aid is positioned. A walking motion may be obtained by the exoskeleton when the control system operates the actuators in the correct sequence. When a mobility impaired disabled user 600 is secured to the WA, the user 600 is caused to move their joints and thuscles through the motions of walking, thereby assisting in the prevention of deterioration of a user's 600 physiology.

It is important to note that mobility impaired disabled users need to be supported to the extent that they are not able to stand by themselves. In this context, a mobility impaired disabled user may be said to be "fully" supported. However, an important aspect of the current WA is its ability to support the mobility impaired disabled user in a position so that their own legs are weight bearing, so that their bones are being subjected to stress. Typically, a mobility impaired disabled user's leg and pelvic bones deteriorate over time. This is caused by the removal or leeching of minerals from their bones when their bones are not subjected to regular stress. In addition to the weakening of their bones, mobility impaired disabled users can suffer from downstream complications from this mineral removal, in that these minerals may build up in other parts of their bodies, for instance in, such as kidney stones or the like.

In subjecting a mobility impaired disabled user's bones to stress where they would otherwise not be, helps prevent deterioration of a user's bones and subsequent complications where minerals removed from the user's bones build up elsewhere in the user's system. Furthermore, causing movement of the user's legs assists in stimulating blood flow through their system, this allows for associated physiological benefits.

Figure 3:
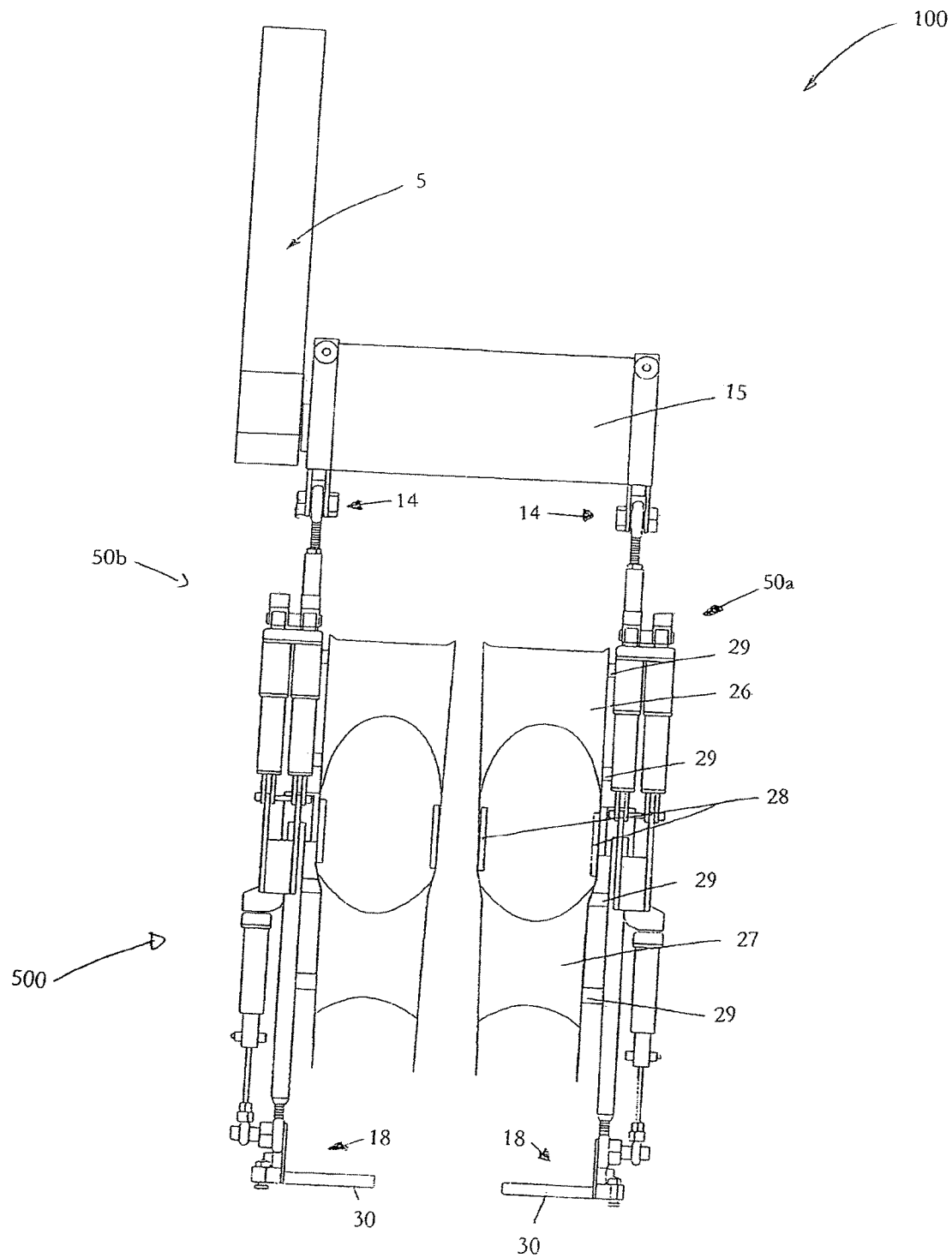
FIG. 3 is a front view of the exoskeleton and orthotics shown in FIG. 1.

With reference to the figures, in FIGS. 1 and 3 there is generally shown a walking aid (WA) 100. The WA 100 includes a moveable mechanical frame or exoskeleton 500 that a user 600 is effectively supported by. It can support and carry the user 600

The WA 100 includes an exoskeleton 500 that is a skeletal structure worn externally by a user 600. It may be powered by an onboard power pack (not shown) that is preferably chargeable from a power source such as a car or at any domestic power socket.

The user is strapped to and supported by the exoskeleton 500. It is envisaged that the WA 100 is a self supporting structure that is capable of moving the user 600. The WA 100 includes a user securing arrangement in the form of a pelvic harness 96 including braces, tethers, strapping, a harness or webbing to hold the user's 600 hips snugly to the hip frame 15, and either orthotics or adjustable fasteners to secure the user's legs and/or feet to the leg structures 50. In one embodiment the braces include orthotics 4 positioned, configured and designed to ensure correct alignment of the users limbs and joints and can also include straps or webbing.

In the preferred form, the WA is controlled by the user by way of a joystick 2 and keypad 3 normally positioned at waist height. The keypad 3 and joystick 2 may be supported by an arm 5. This may be able to pivot to move between at least one operational position (eg in use extending horizontally or pointing down vertically) and a retired position (eg extending vertically).

As will be explained later, the control system of the WA may be programmed to receive instructions and act on those instructions to move the WA. The WA may move to effect a walking forwards and backwards and turning whilst walking, turning in place and stepping to the side. It may also allow for sitting and standing. It may also allow for ascending and descending sloping surfaces through one or more planes. During both static and dynamic operation of the WA, the WA is controlled to ensure the user remains in a balanced condition. As will be explained later, the WA may amongst other things also include features to ensure it can for example adjust to the slope of a terrain automatically.

Figure 2:
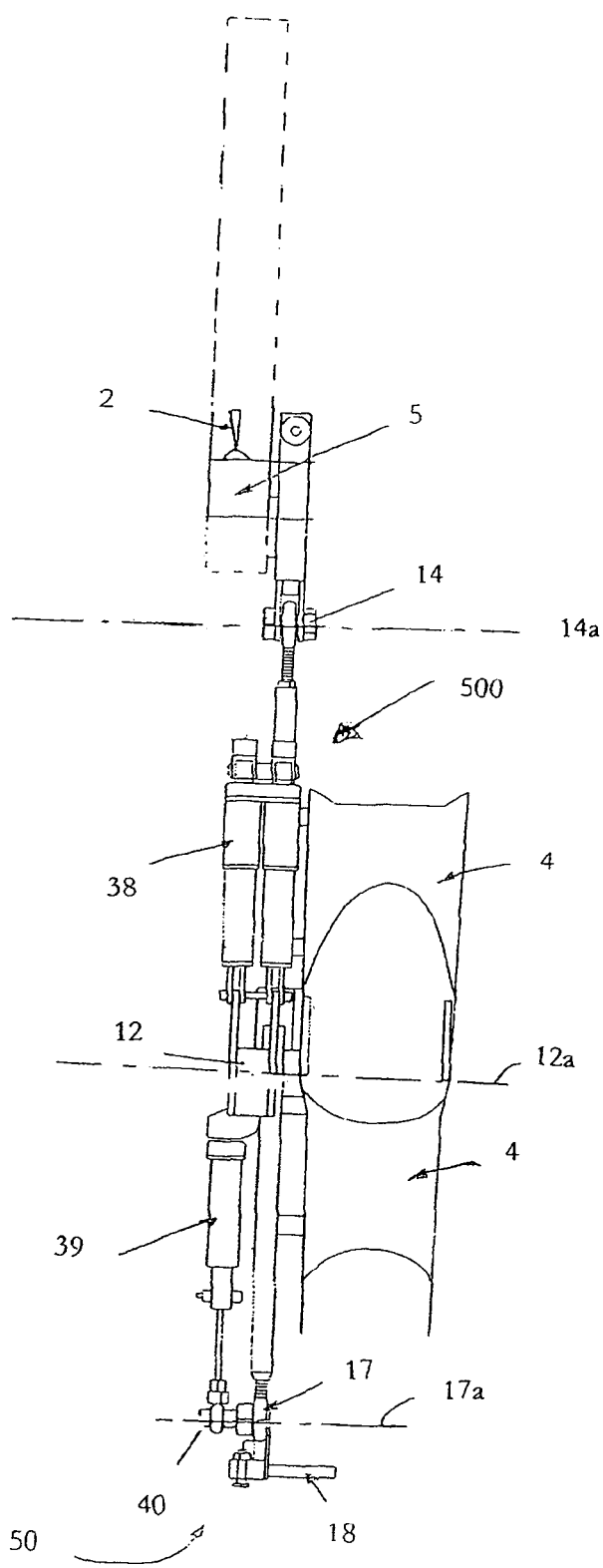
FIG. 2 is a cutaway front view of part of the exoskeleton and orthotics that is shown in FIG. 1.

With reference to FIGS. 1-3, the exoskeleton 500 includes an upper leg structural member 10 and a lower leg structural member 11. These are connected by a knee joint 12 that defines a pivot axis 12A to allow the upper leg member 10 and lower leg structural member 11 to pivot relative to each other. The pivot axis 12A ensures the upper leg member and lower leg member can rotate relative to each other but only about one pivot axis.

Movement about the knee axis 12A of the upper leg member and lower leg member can be actuated by the knee actuator 13. The knee actuator 13 extends between parts of the upper leg member and lower leg member for the purposes of actuating relative rotational movement between the upper leg member 10 and lower leg structural member 11.

Figure 43:
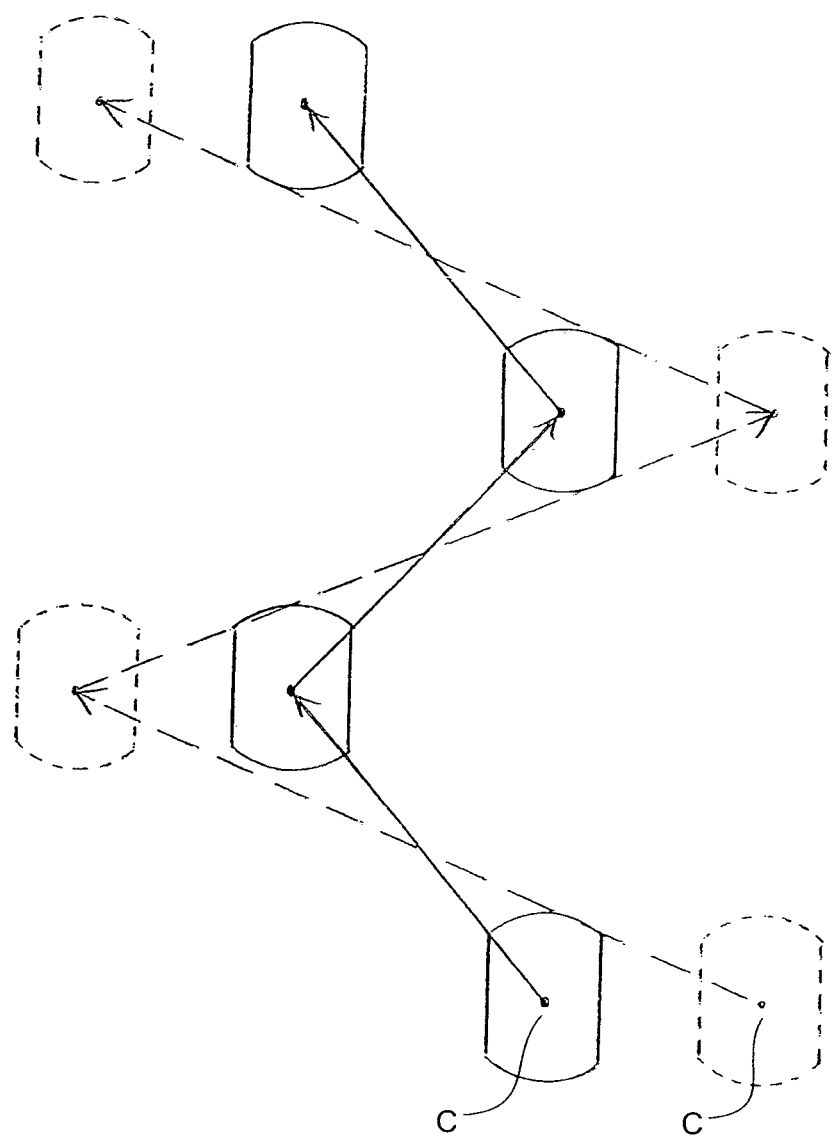
FIG. 43 shows a schematic diagram illustrating the movement of centre of mass of the WA and user between steps during a walking movement.
Figure 44:
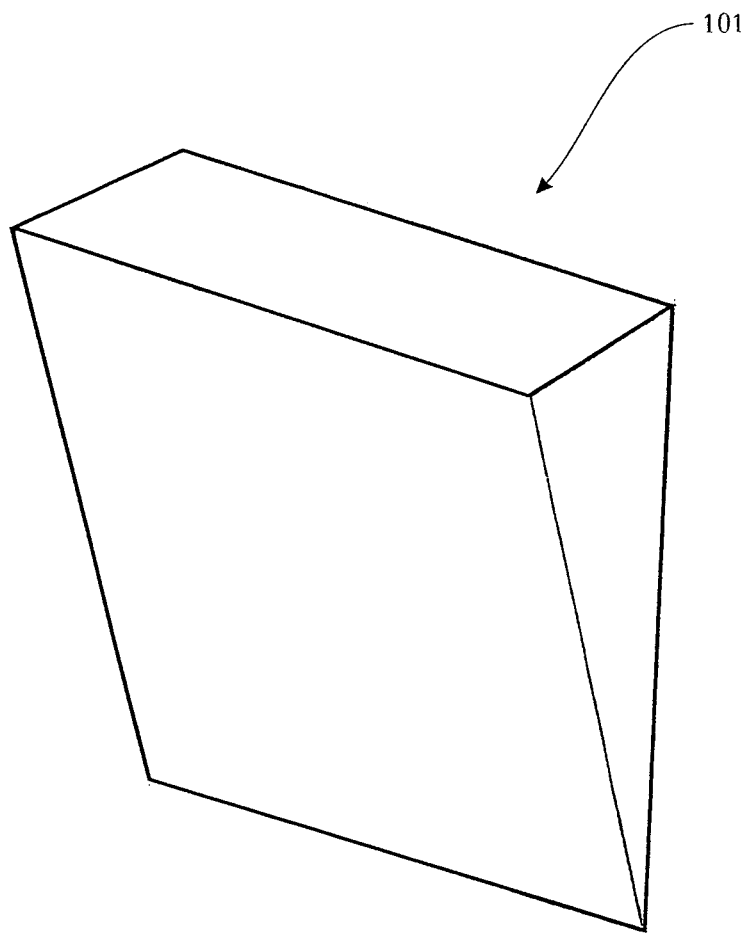
FIG. 44 shows a wedge shaped foam packing arrangement.
Figure 45E:
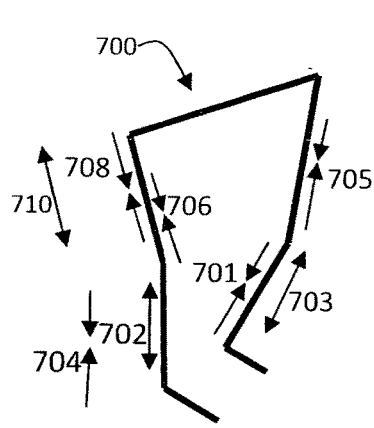
Figure 45F:
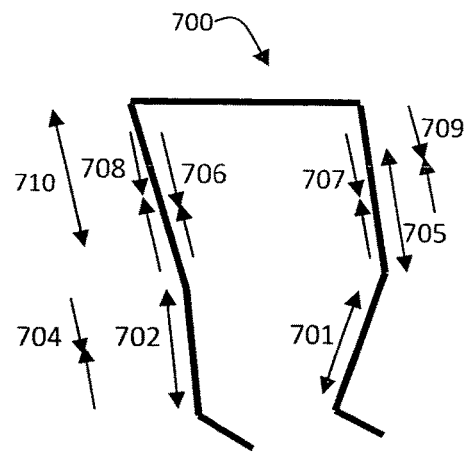
Figure 45G:
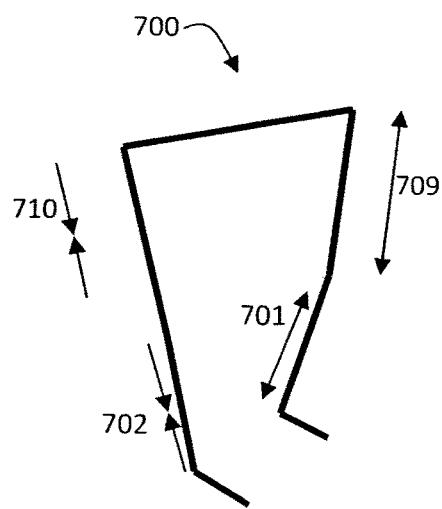
Figure 45H:
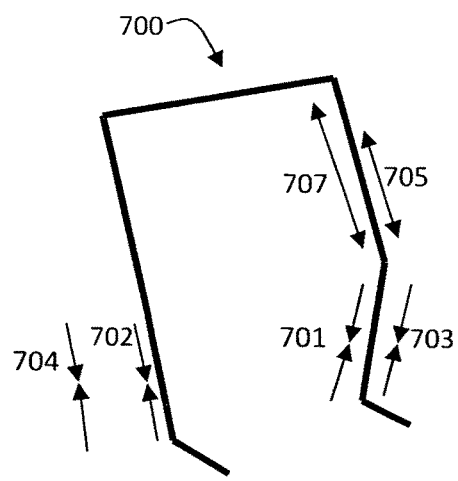
Figure 45I:
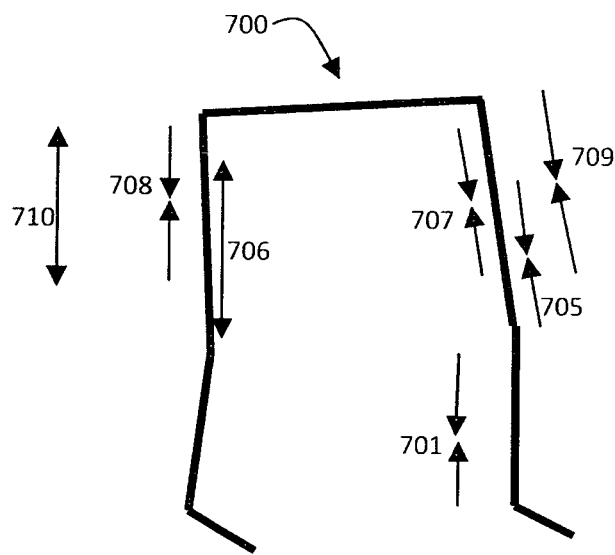
Figure 45J:
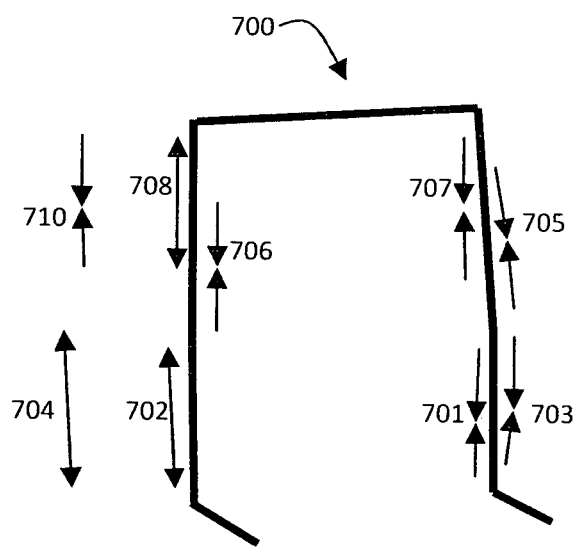
Figure 47A:
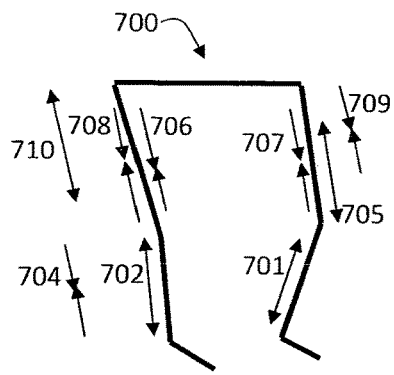
FIGS. 47*a*-47*e* show the model of the exoskeleton undergoing a right dynamic step movement sequence in accordance with a preferred form of the control system of the WA.
Figure 47B:
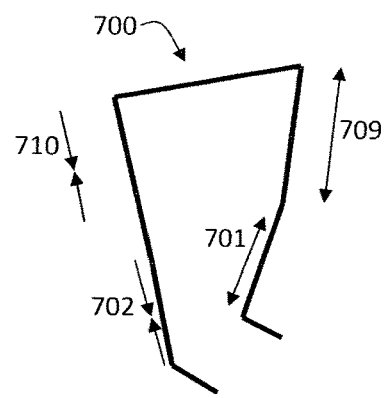
Figure 47C:
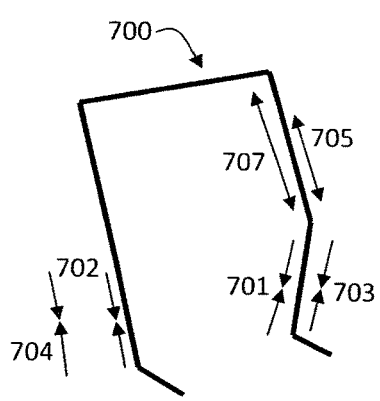
Figure 47D:
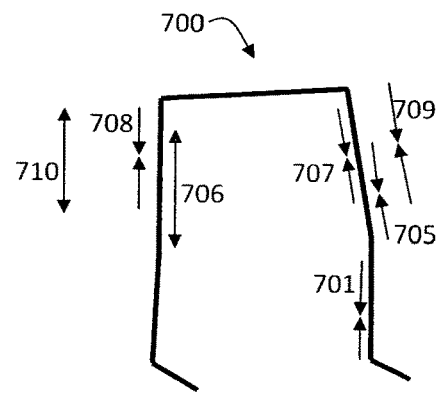
Figure 47E:
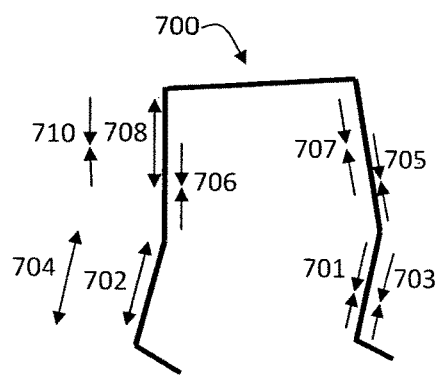

The knee joint 12 is preferably located at a distal first end 10b of the upper leg member 10. At a first end 10a of the upper leg member 10 is a hip joint 14 that pivotally engages the upper leg member 10 with the hip frame 15. The hip joint 14 defines a hip axis 14A that in use is located relative to the user 600 at or approximate to the natural axis of hip rotation in an anterior/posterior direction of movement. In a preferred embodiment, each hip joint 14 is configured relative to the hip frame 15 with its axis of rotation 14A extending downwardly in a lateral direction at an angle of between zero and ten degrees, and more preferably of about four degrees. This inclination of the axis of rotation 14A mimics a human being's upper leg alignment and is illustrated as angle α in FIG. 30. The inclination means that the foot members of the WA 100 are closer together, which allows for more natural transfer of the centre of mass (generally located about the middle of the pelvis) to a point within the support area provided by the foot members 18 when the WA 100 is controlled to move through a walking motion. This is further illustrated in FIG. 43, showing how the movement of the combined centre of mass (illustrated as point C) of the WA 100 and the user moves in a reduced side to side movement between the individual steps in a walking movement, compared to a WA not having such an inclination of the axis of rotation of the hip joint (shown in broken lines).

The hip joint 14 allows for a relative rotation between the upper leg member 10 and the hip frame 15. Such rotation is preferably primarily about an axis that is parallel to the knee axis 12A. However the hip joint 14 also allows for a rotation of the upper leg member 10 relative the hip frame 15 in a medial/lateral plane direction, which will in operation result in a movement of a user's 600 leg along a medial/lateral plane (e.g. the leg splaying outwardly). This multi axis pivoting capability can be facilitated by the use of a rose joint to define the hip joint 14. It is envisaged that the hip joint 14 (in the form of a rose joint) may be limited in its movement by a pair of horizontally aligned plastic, and preferably rigid plastic (e.g. Teflon or high density polyethylene), bushes (not shown) disposed on either side of the rose joint. A vertically aligned flange (not shown) connected to the upper leg structural member 10 will be prevented from pivotal movement in a horizontal plane in this way, at least partially preventing pivoting movement of the upper leg structural member 10 about its longitudinal axis.

Rotation of the hip frame, or also herein referred to as the pelvis harness 15 relative the upper leg member 10 about an axis parallel to the knee axis 12A, at the hip joint 14 can be achieved by the use of the main hip actuator 16.

Disposed at a second distal end 11b (the end away from the knee joint) of the lower leg structural member 11, is a foot member 18. The foot member 18 is capable to rotating relative the lower leg structural member 11 by virtue of the foot joint 17. The foot joint 17 preferably defines a pivot axis 17a that extends parallel with the knee axis 12A. Pivotal movement of foot member 18 about the foot joint 17 relative to the lower structural support member 11 in the anterior/posterior plane can be effected by the foot actuator 19. The foot joint 17 may, like the hip joint, be a rose joint to facilitate its multi-axis pivoting capability. The foot joint 17 can allow for the foot member 18 to have multiple degrees of rotational movement relative the lower leg structural member 11. In a preferred embodiment, it is envisaged that the foot joint 17 is configured for providing pivotal movement of the lower leg structural member 11 in a medial/lateral plane and an anterior/posterior plane about said foot member 18, while at least partially preventing pivoting movement of the lower leg structural member 11 relative to the foot member 18 about its longitudinal axis. This limitation on pivoting or twisting movement is accomplished in a similar manner to that of the hip joint 14, that is by the insertion of bushes made from a rigid plastics material on either side of the rose joint. It is envisaged that in a preferred embodiment, each foot joint 17 is configured with its axis of rotation 17A extending downwardly in a lateral direction at an angle of between zero and 6 degrees, and more preferably at about four degrees.

A secondary foot actuator 39 may be provided, and coupled to the foot member 18 to control a rotational movement of the foot member in a direction substantially transverse to the direction in which the main foot actuator 19 can control rotational movement and substantially along a medial/lateral plane. The secondary foot actuator 39 may be engaged to an axle or lever arm 40 of the foot member 18 to facilitate this pivoting movement.

Figure 5:
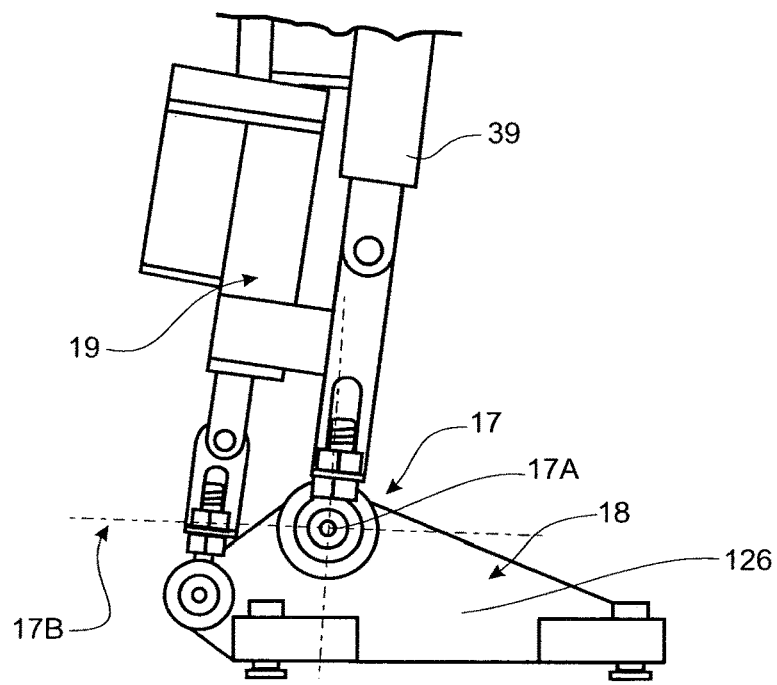
FIG. 5 is a cutaway side view of part of the exoskeleton of FIG. 1 in the region of the foot member.
Figure 6:
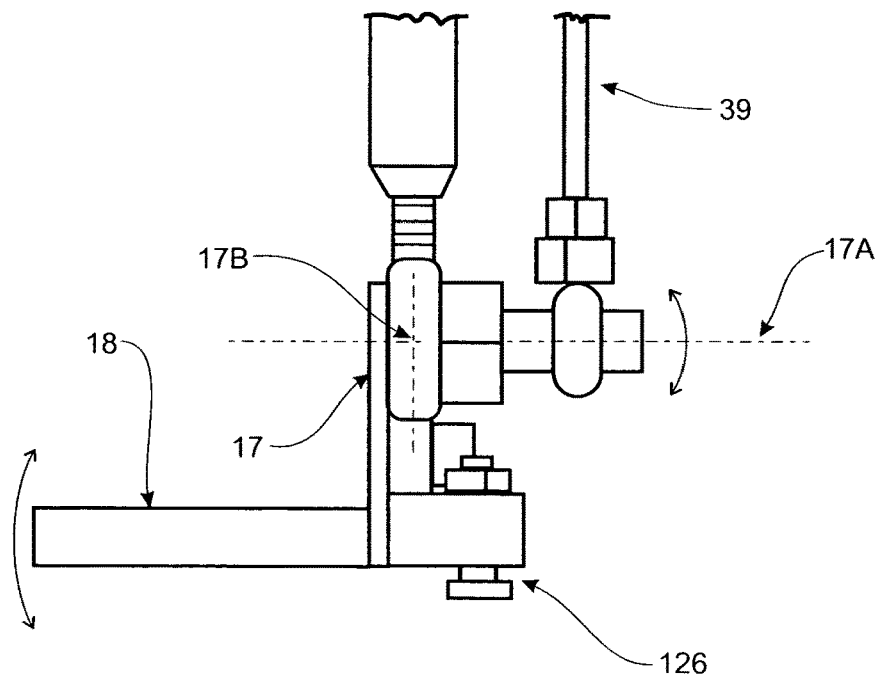
FIG. 6 is a rear view of FIG. 5.

With reference to FIGS. 5-6, in FIG. 5 there is shown a close up view of the foot member 18, foot joint 17 and lower leg structural member 11 of the device, wherein it can be seen that a secondary axis 17b is provided about which the foot member 18 can rotate as a result of operation of the secondary actuator 39.

Figure 7:
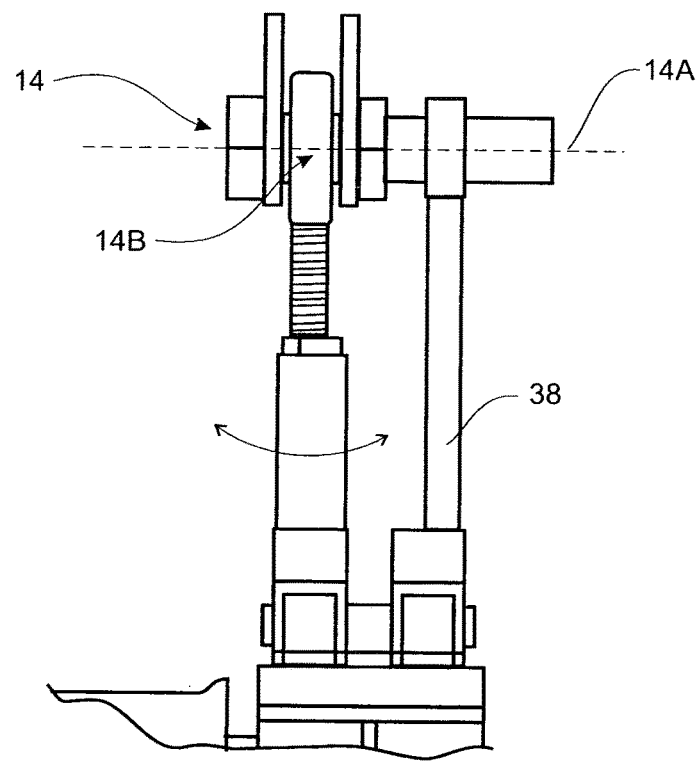
FIG. 7 is a cutaway front view of part of an exoskeleton of a second embodiment including a secondary hip actuator in the region of the hip joint.
Figure 8:
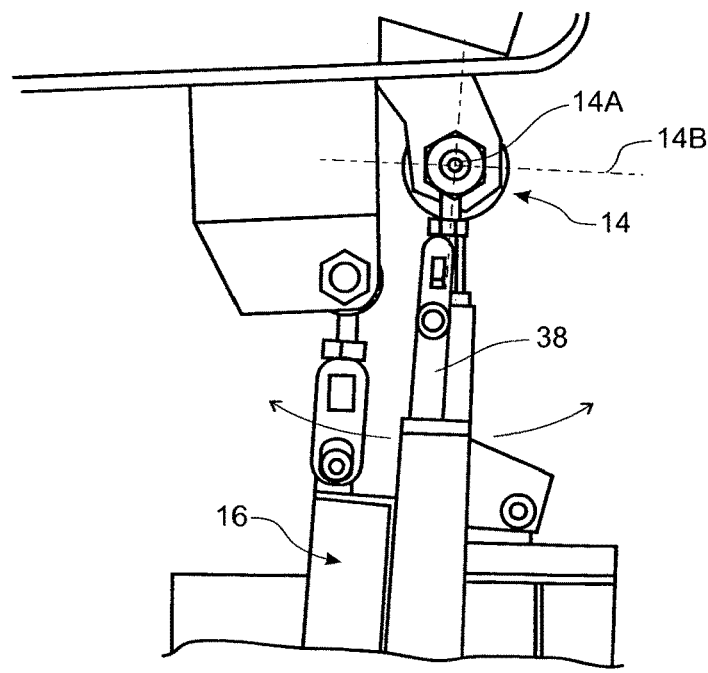
FIG. 8 is the side view of FIG. 7.
Figure 8A:
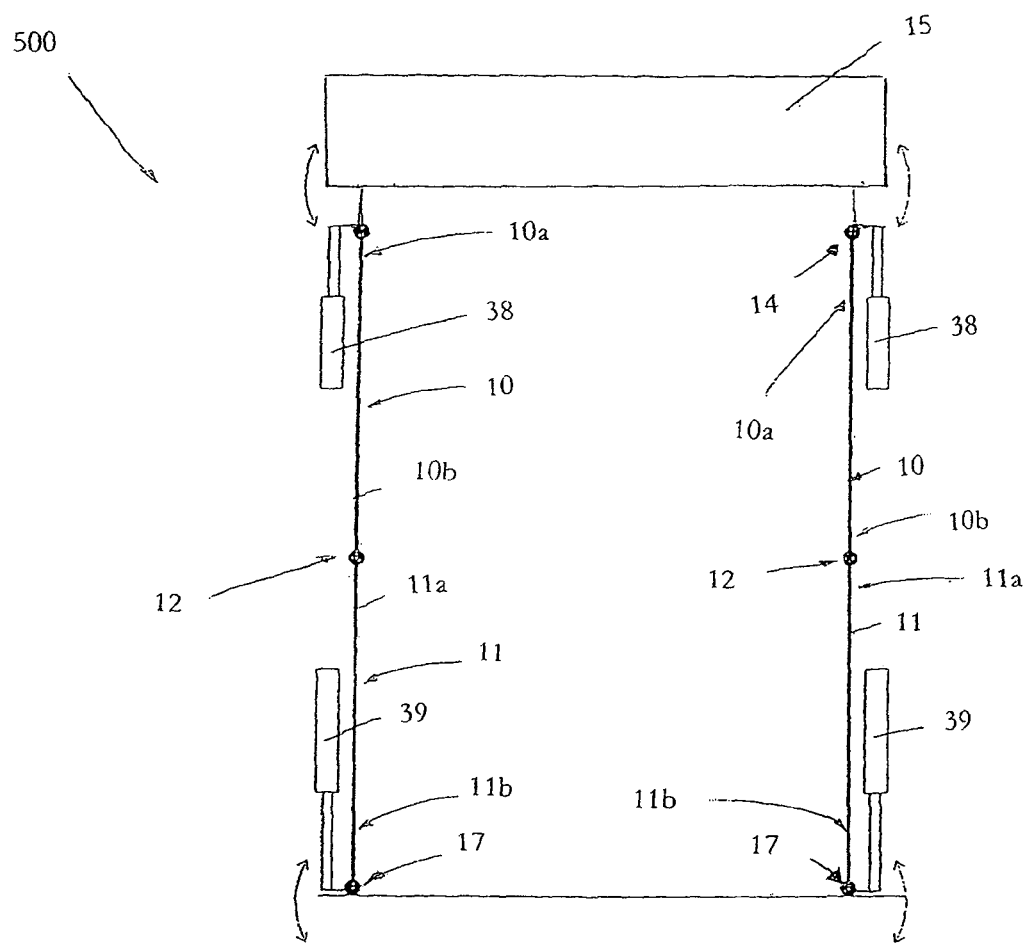
FIG. 8a shows schematic layout of the lateral movement actuators of the exoskeleton seen from the front.

With reference to FIGS. 7-8, it can be seen a primary axis of rotation is about axis 14a and a secondary axis is defined by axis 14b, movement about which can be controlled by the secondary hip actuator 38.

To allow for the WA 100 to be fitted to a user to allow the user to operate the device in a safe manner, it is important to ensure that the spacing between hip joint 14, knee joint 12 and foot joint 17 is appropriate. Appropriate positioning should be where such joints are, as close as possible, aligned with the corresponding natural joints of a user.

The exoskeleton 500, when worn by a user will sit relative a user 600 in a position defined by a combination of factors. The user is preferably held to the exoskeleton by the use of orthotics (which shall be described in more detail hereinafter) that are engaged to the exoskeleton. Adjustment of the position of the hip joint, knee joint and foot joint is achieved by virtue of an adjustment in the effective length of the upper leg member 10 and the lower leg structural member 11. Such adjustment may be achieved by a turn buckle style adjustment means 20 that may be located at the second distal end of the lower leg structural member 11 and a turn buckle 21 at the first distal end of the upper leg member 10. The turn buckle 21 can allow for the distance between the hip joint 14 and knee joint 12 to be varied and the turn buckle 20 can allow for the distance between the knee joint and the foot joint 17 to be varied. In an alternate embodiment, the length adjustment may be accomplished by the insertion of lengthening inserts, which may be screwed into the upper and lower leg structural members 10, 11. It will be appreciated that adjustment features can be provided elsewhere and may also come in different forms such as in the form of a snap fit arrangement, bayonet type arrangement, telescopic or other means of setting the distance between the joints. This adjustment can allow for the one device to be used by different users that may be of differing body shape or size.

Figure 12:
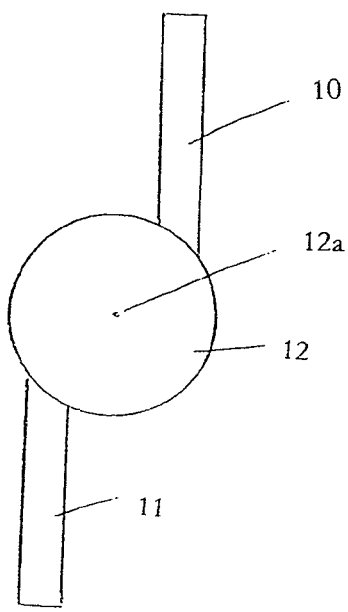
FIG. 12 shows a side view of the knee joint in schematic form showing the offset of the knee joint.
Figure 13:
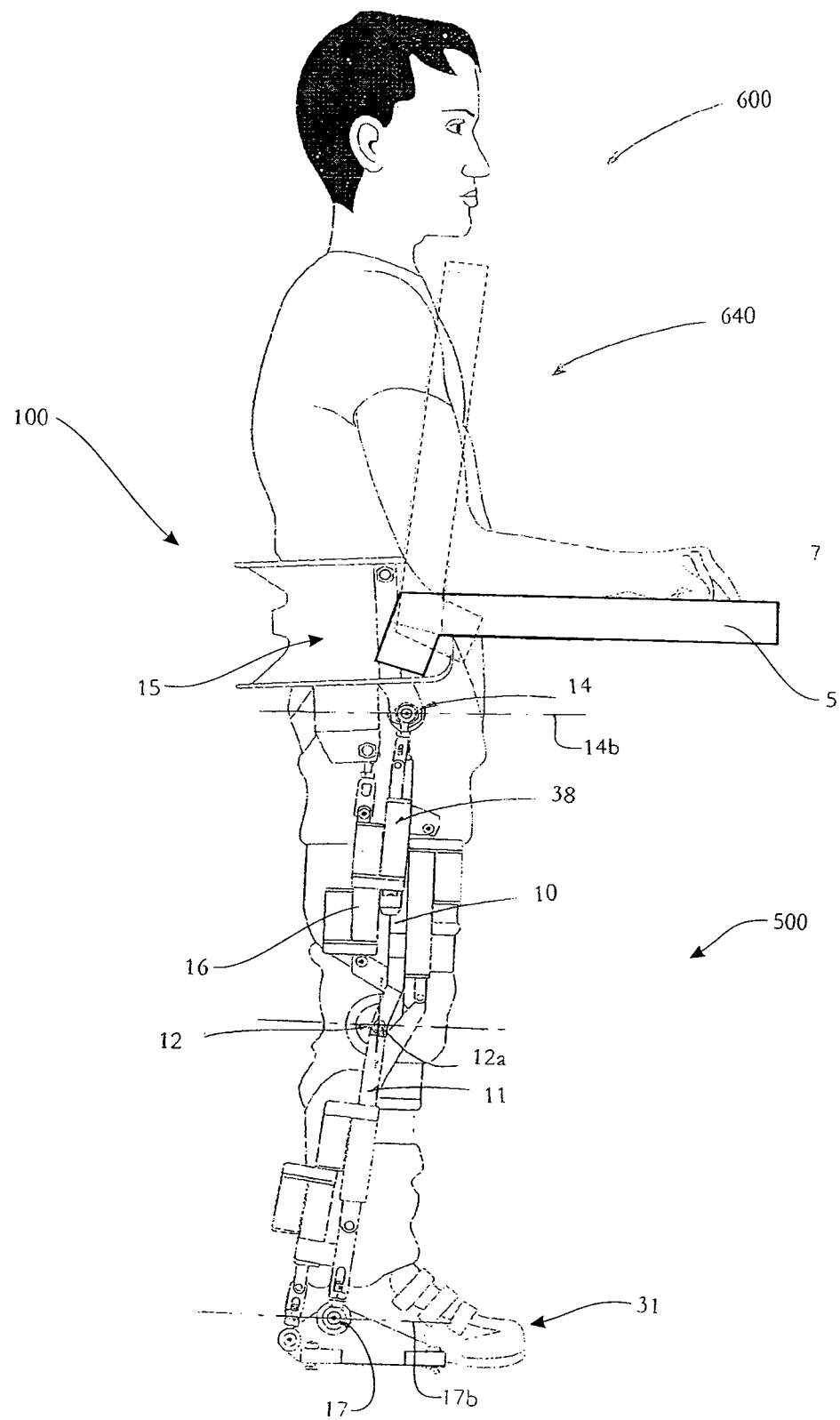
FIG. 13 is a side view of a person being supported by another embodiment of the WA including a secondary hip actuator.
Figure 14:
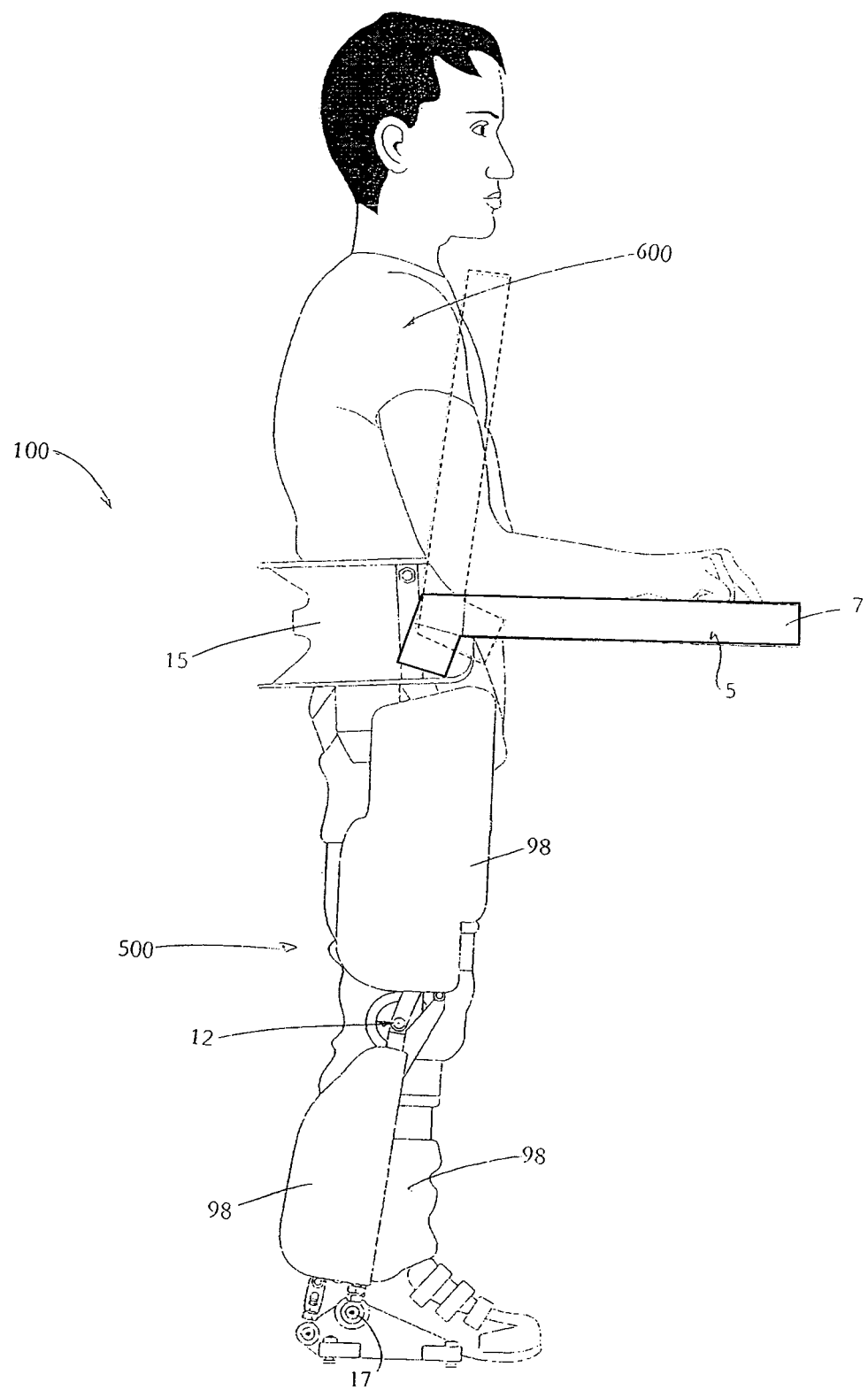
FIG. 14 shows a side view of a person supported by a WA with covers attached to it.
Figure 15:
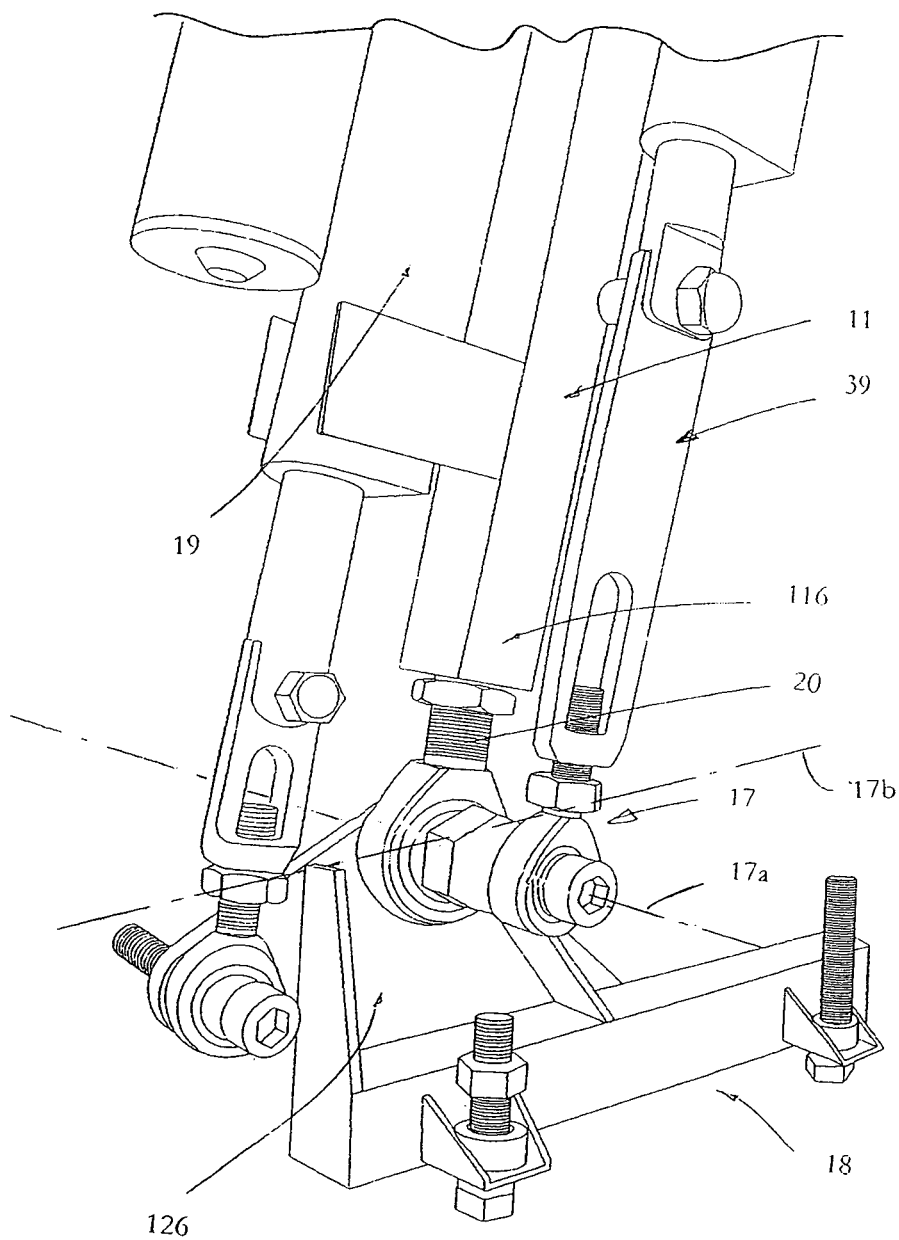
FIG. 15 shows a perspective cutaway rear view of the foot member and lower leg structural member of the exoskeleton.

With reference to FIG. 12, there is shown a view of the knee joint 12 from the side. As may be seen, in a preferred embodiment, the upper leg member 10 in its elongated direction is offset from the pivot axis 12a of the knee joint 12. The lower leg structural member 11 does project through the axis 12a. This correctly aligns the knee pivot joint with the user's knee joints and prevents knee damage to the user 600. The axis 12a is in a location behind (in a forward direction of travel of the user) the location at where the upper leg member 10 projects. This offset of the WA knee joint replicates and aligns to the form of the human skeleton, therefore avoiding any stress or damage to the user's knee joint.

Whilst in FIG. 2, only part of the exoskeleton is shown, with reference to FIG. 3, the full exoskeleton is shown wherein two leg structures 50a and 50b are shown. The leg structures 50 are held together by the hip frame 15. The hip frame 15 holds part of the hip joints 14 thereby setting a fixed spacing of the hip joints 14 relative each other. The hip frame 15 is preferably a rigid member that can sit about part of the waist of a user. Preferably the hip frame 15 extends substantially about the posterior of the hip region of a user 600. The hip frame 15 may also extend about part of the waist of the user.

Figure 4:
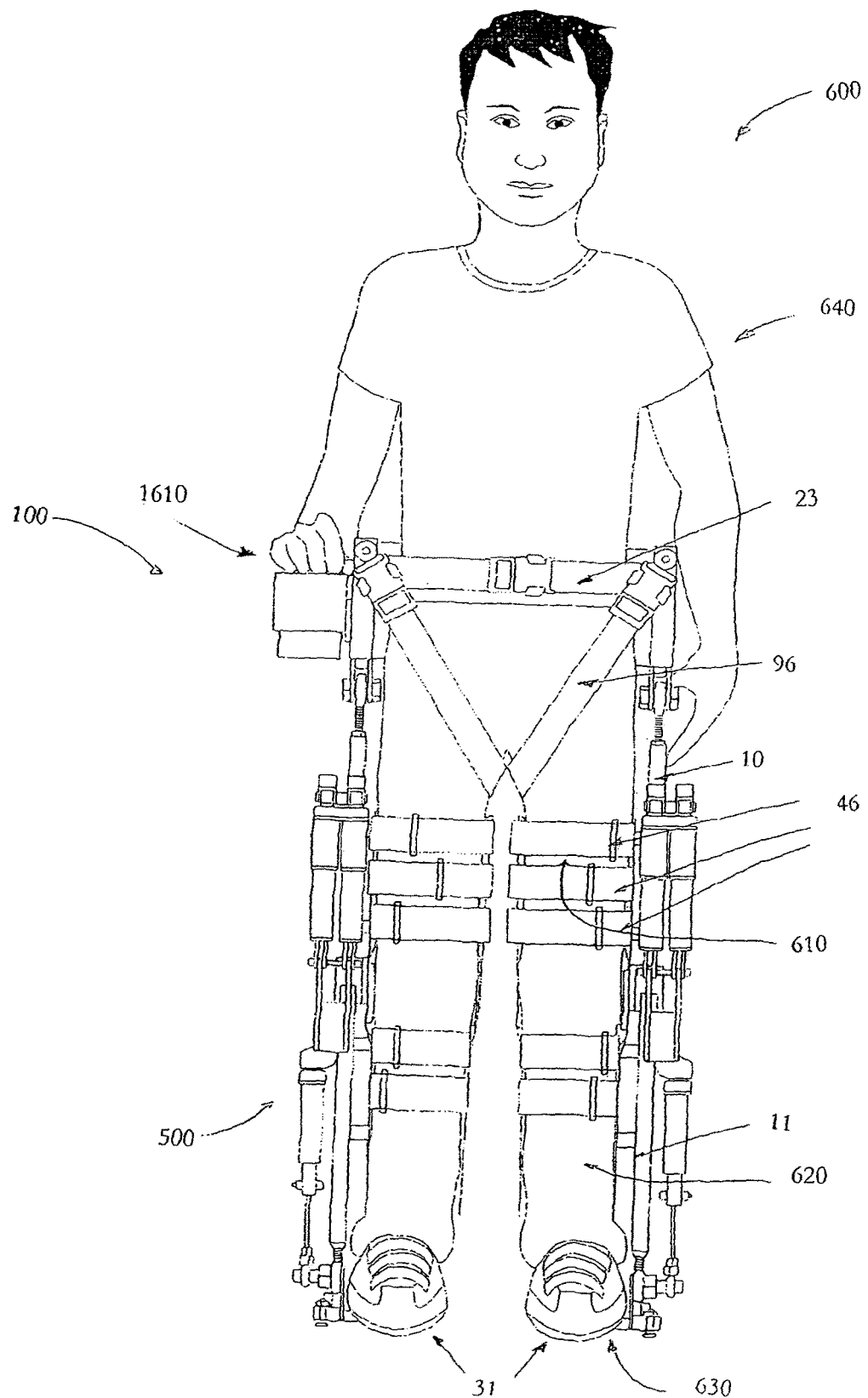
FIG. 4 is a front view of the WA of FIG. 1 supporting a user.

The user is supported at the hip frame by a pelvic harness 96 which may include adjustable straps or webbing which extend about the legs of a user and are fastened and released as appropriate by the user. Such webbing may be adjustable in length. It may include the likes of a hook and loop fastening system such as Velcro® for facilitating easy entry and exit from the WA by the user. With reference to FIG. 4 it can be seen that the harness can include webbing 23. A user 600 can be strapped to the hip frame 15 by webbing 23 around their waist to ensure that the user remains firmly held to the hip frame 15. Further, a packing arrangement 101 composed of a material such as wedge shaped foam or foamed plastic may be used to ensure a snug fit by the user in the hip frame 15. It is also envisaged that the packing arrangement 101 could be an inflatable thin walled pressure vessel (not shown)

Further support to the user is provided by orthotics as an alternative or in addition to the adjustable fasteners 46 described above. The orthotics are orthotic designed braces that help ensure the user 600 is not only supported but is also correctly aligned within the exoskeleton so as not to damage the user's 600 limbs or joints. They may include webbing or straps to hold the user in position relative to the formed portion of the orthotics. The webbing 23 may also facilitate an easy and adjustable fitting and release of the user from the WA 100.

The orthotic braces are preferably engaged and/or capable of being releasably engaged to the exoskeleton. With reference to FIG. 3, the orthotics may include an upper leg orthotic 26 and a lower leg orthotic 27. These may be directly joined to each other or indirectly joined to each other by the exoskeleton. For example with reference to FIG. 3, the upper leg orthotic 26 and lower leg orthotic 27 may be joined at the joints 28. The orthotics are engageable to the exoskeleton 500 via connectors 29.

The connectors 29 rigidly hold the orthotics to the exoskeleton. The connectors 29 may facilitate a releasable engagement of the orthotics to the exoskeleton 500. This can be beneficial to a user 600 who normally wears orthotics. This allows for such a person to more rapidly associate themselves with the exoskeleton 500. It also allows for such a person to associate with the exoskeleton 500 in a more comfortable manner because the orthotics 4 are already engaged to the person in an appropriate location. So, the user 600 may use the adjustable fasteners 46 supplied with the WA 100 or may use their own braces by the use of a supplied interface that the user's orthotic specialist can fit onto the users braces. It is necessary for users to be able to interface with the WA 100 bearing in mind that many users 600 have specific orthotic requirements and cannot wear generic braces.

Being able to release the orthotic brace from the WA 100 and wear the brace as a normal use brace allows users to transfer out of and into the device quickly without having to change braces.

The connectors 29 are of a shape and configuration so that a correct alignment of the upper and lower leg of the person is achieved once engaged to the exoskeleton. The connectors 29 may be of a dove tail configuration or snap lock configuration or other to facilitate a rapid engagement and disengagement of the orthotics with the exoskeleton.

The user 100 may engage with the exoskeleton, wearing their own shoes that can be placed on platforms 30 of each foot member 18. Alternatively the exoskeleton includes footwear such as a shoe 31 into which the user 600 can place their feet 630. The footwear 31 may remain permanently engaged with the exoskeleton 500 and a user can place their feet in the footwear. The shoes 31 preferably have a rigid frame on the outside edge with a precision keyway. The negative of said keyway is on the WA 100. These two parts slide one into the other causing an automatic locking pin to engage when correctly positioned. The rear portion of the fixing contains all of the electrical connections for the sensors contained within the shoe. Correct alignment of the shoe ensures a complete connection. The automatic pin can be released manually or electronically.

The linear actuators used are preferably low voltage DC actuators with position feedback through a sensor in the actuator. The low voltage aspect of the actuator is important in that it is safe for use and will do no harm to the user in the case of a fault. The feedback sensors are relevant in that they give the system an awareness of the position of the limbs at any time and can be used to drive the limbs to predetermined fixed positions in the pre-programmed sequences employed by the control system as will be explained later. Typically, an actuator would be caused to move by an electric motor (not shown) driving a worm gear (not shown), which in turn causes the actuator to extend or retract.

Figure 16:
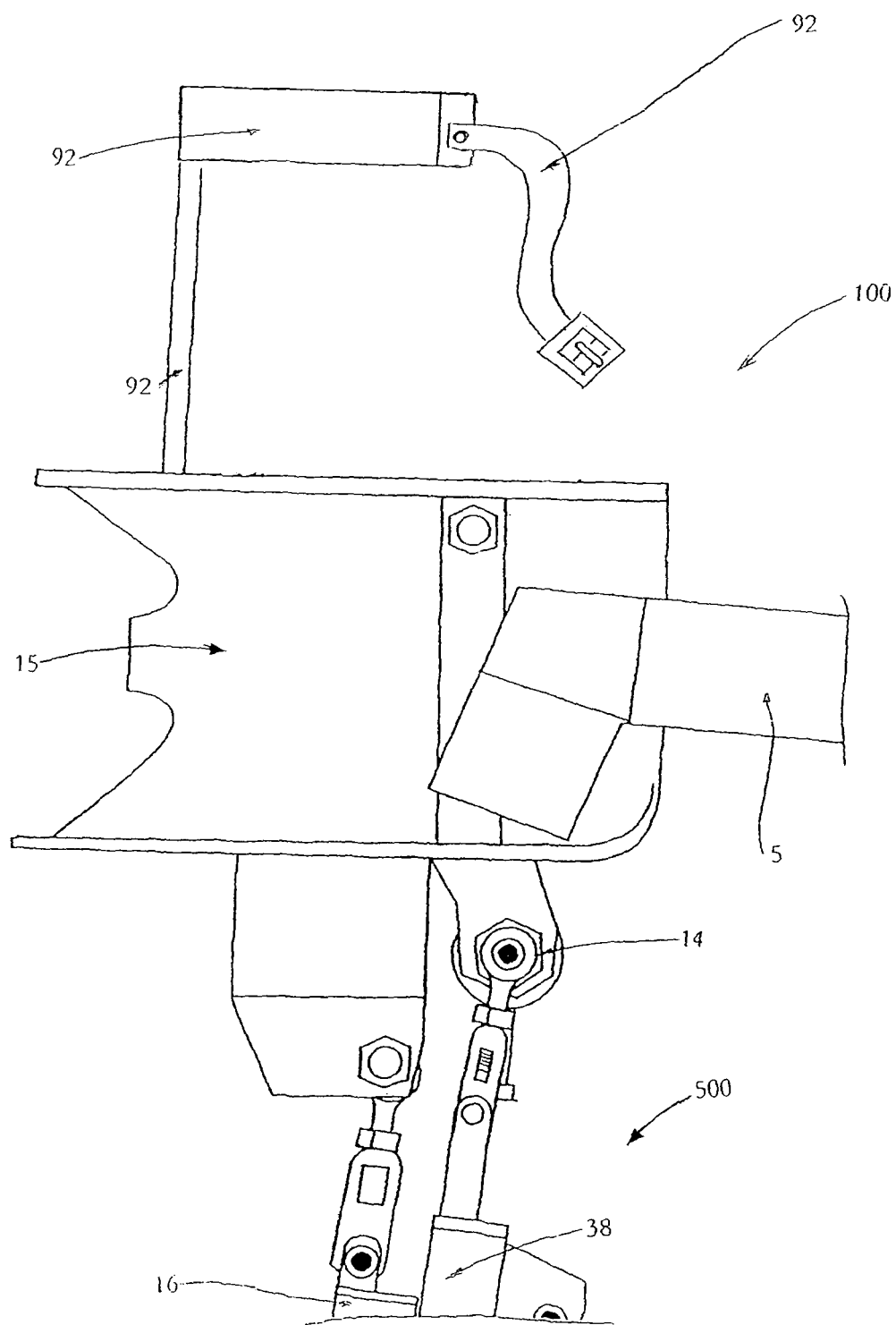
FIG. 16 shows a side view of an upper region of the exoskeleton including an upper body control extension for supporting upper body movement relative to the pelvic brace.
Figure 17:
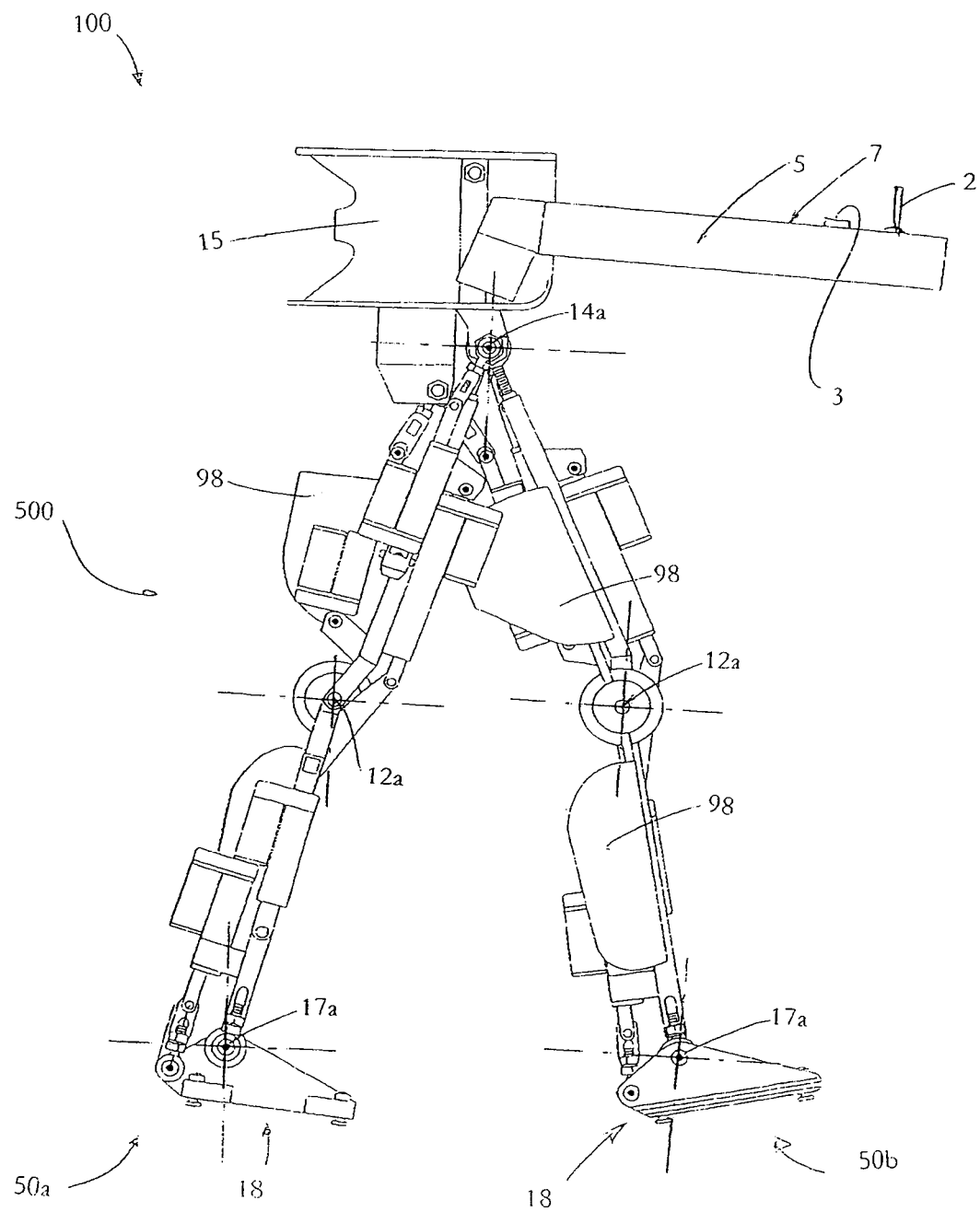
FIG. 17 shows a side view of a WA in a stepping forward position.
Figure 18:
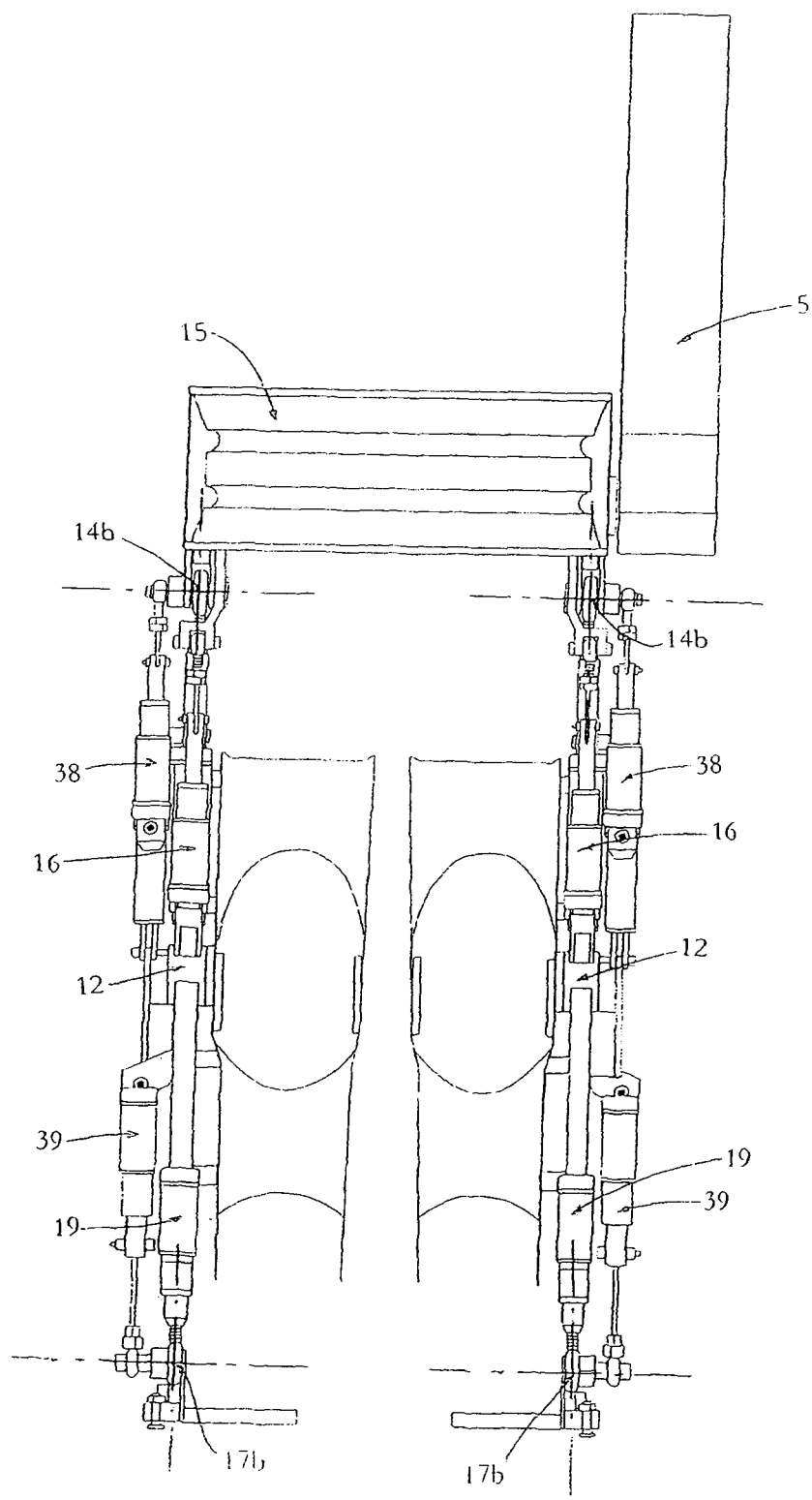
FIG. 18 shows a rear view of a WA including a secondary hip actuator.
Figure 19:
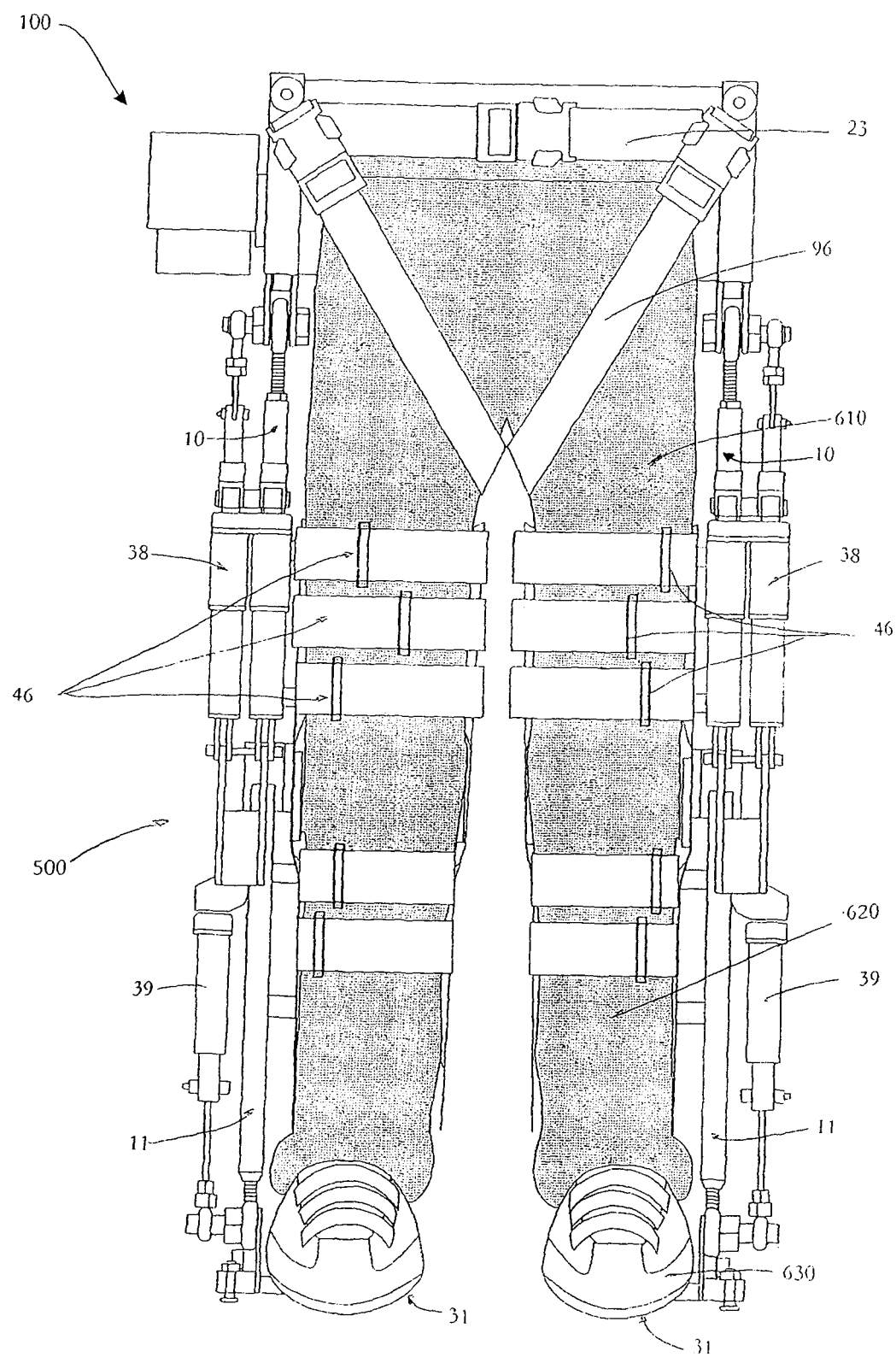
FIG. 19 shows a front view showing in more detail the bracing and support that is provided to secure the user by the exoskeleton.
Figure 20:
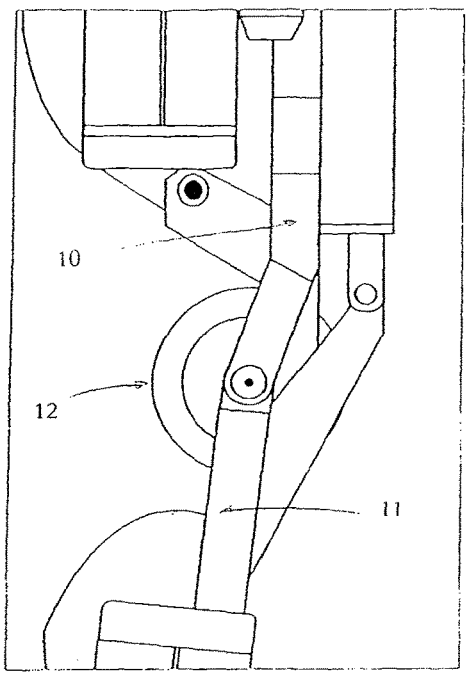
FIG. 20 shows a cutaway right side view of the knee region of the exoskeleton showing a knee pivot offset.
Figure 21:
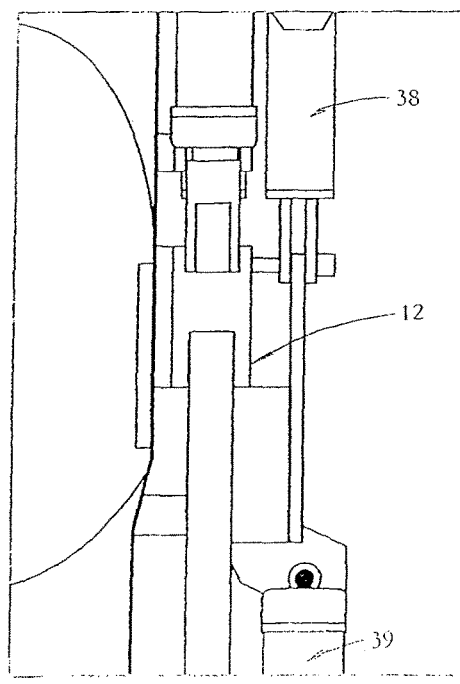
FIG. 21 shows a cutaway right rear view of the preferred knee pivot off set
Figure 22:
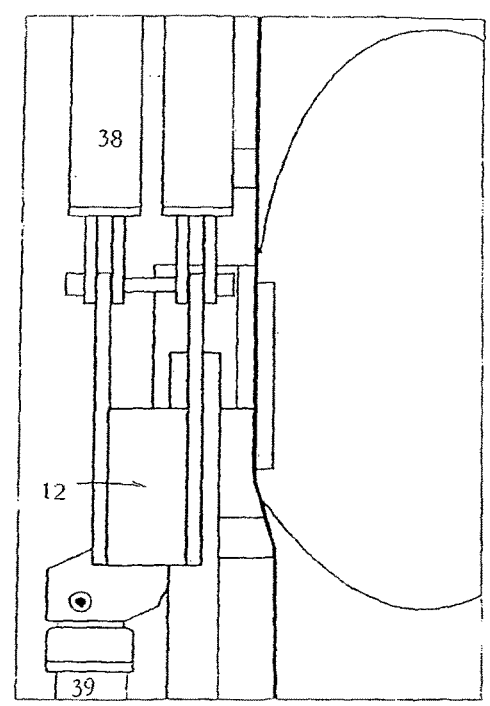
FIG. 22 shows a cutaway right front view of the knee pivot offset.
Figure 23:
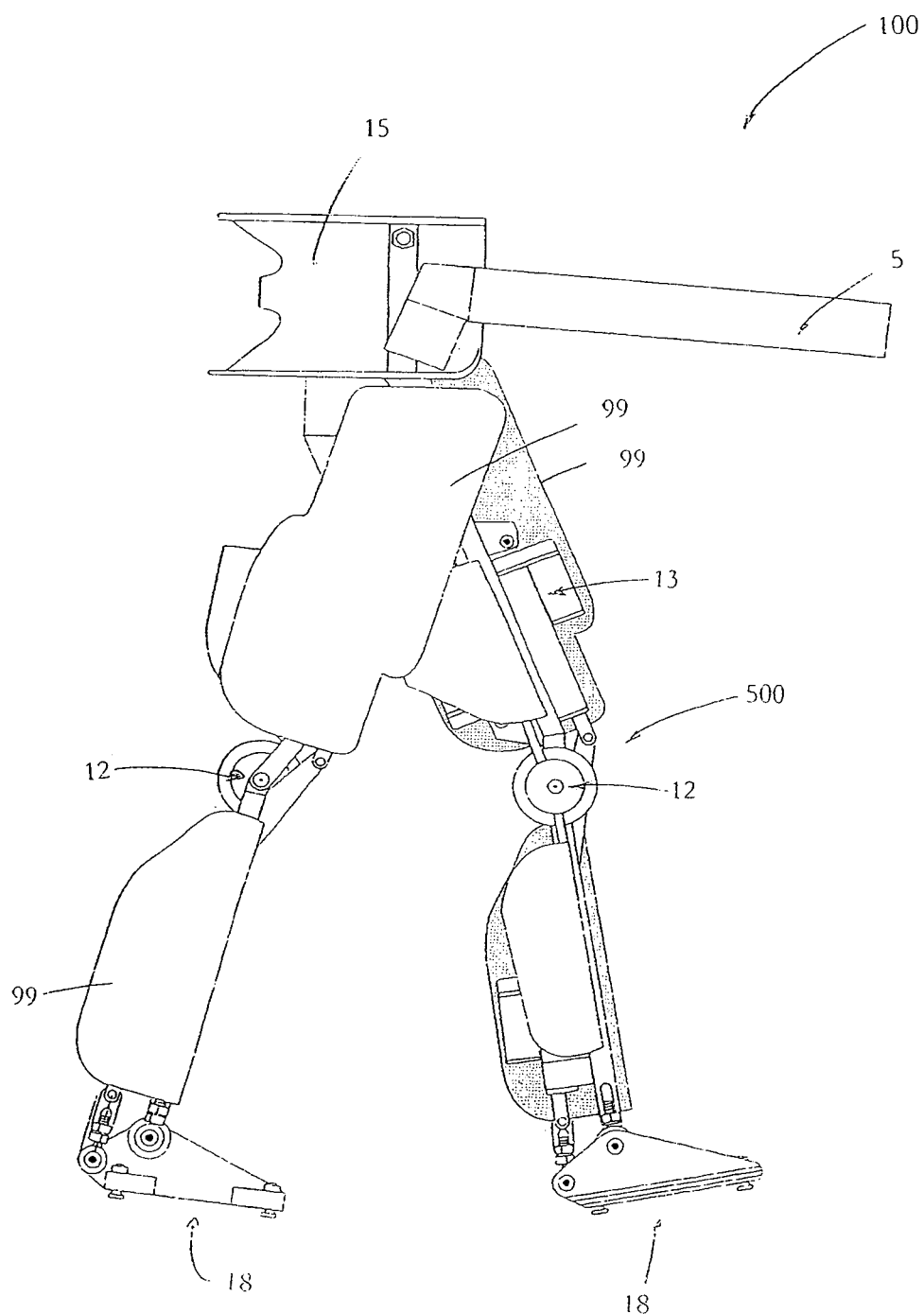
FIG. 23 shows a side view of a WA with covers on, FIG. 24 shows a rear view of a WA with covers on, FIG. 25 shows a front view of a WA with covers included and supporting the user.
Figure 24:
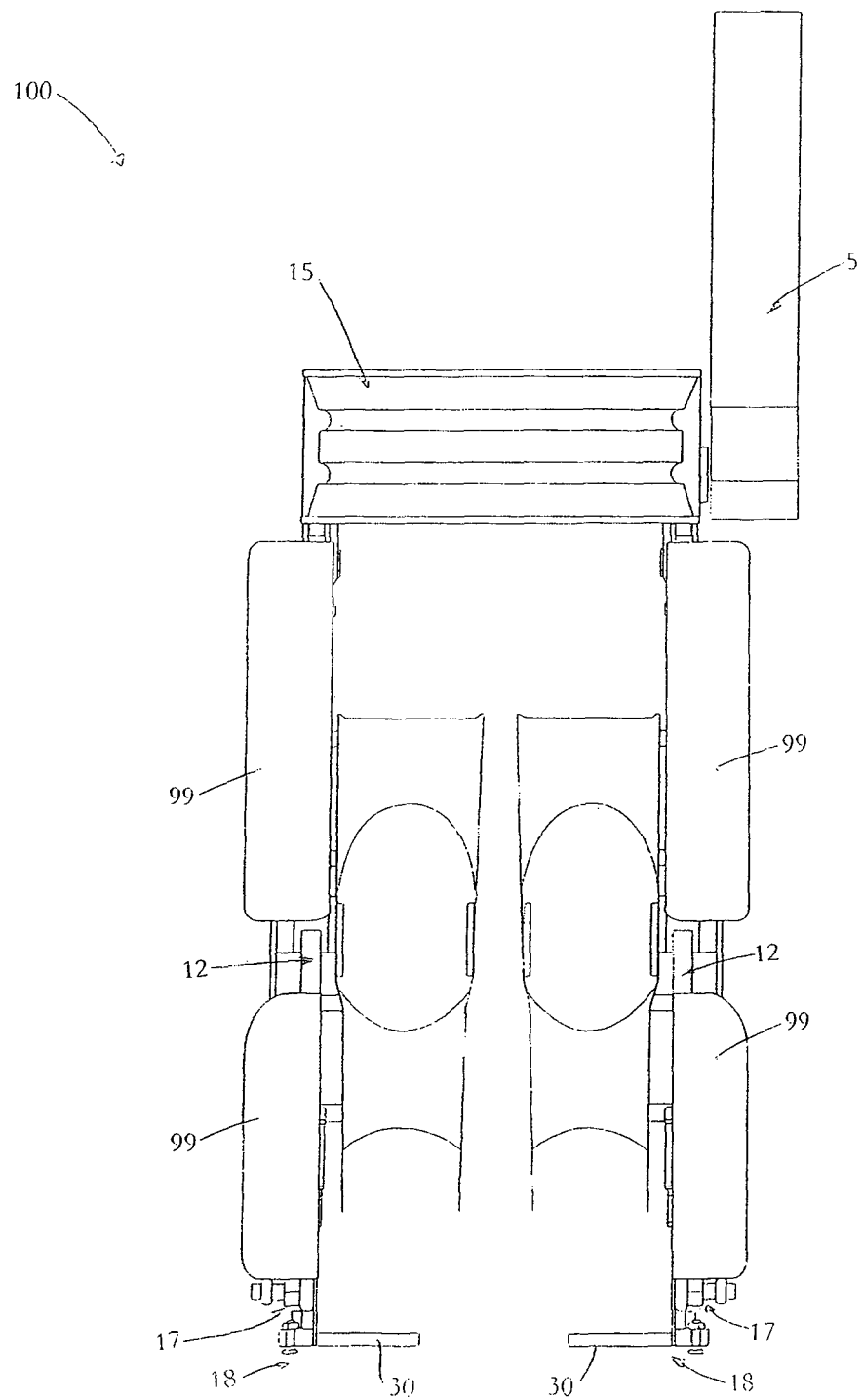
Figure 25:
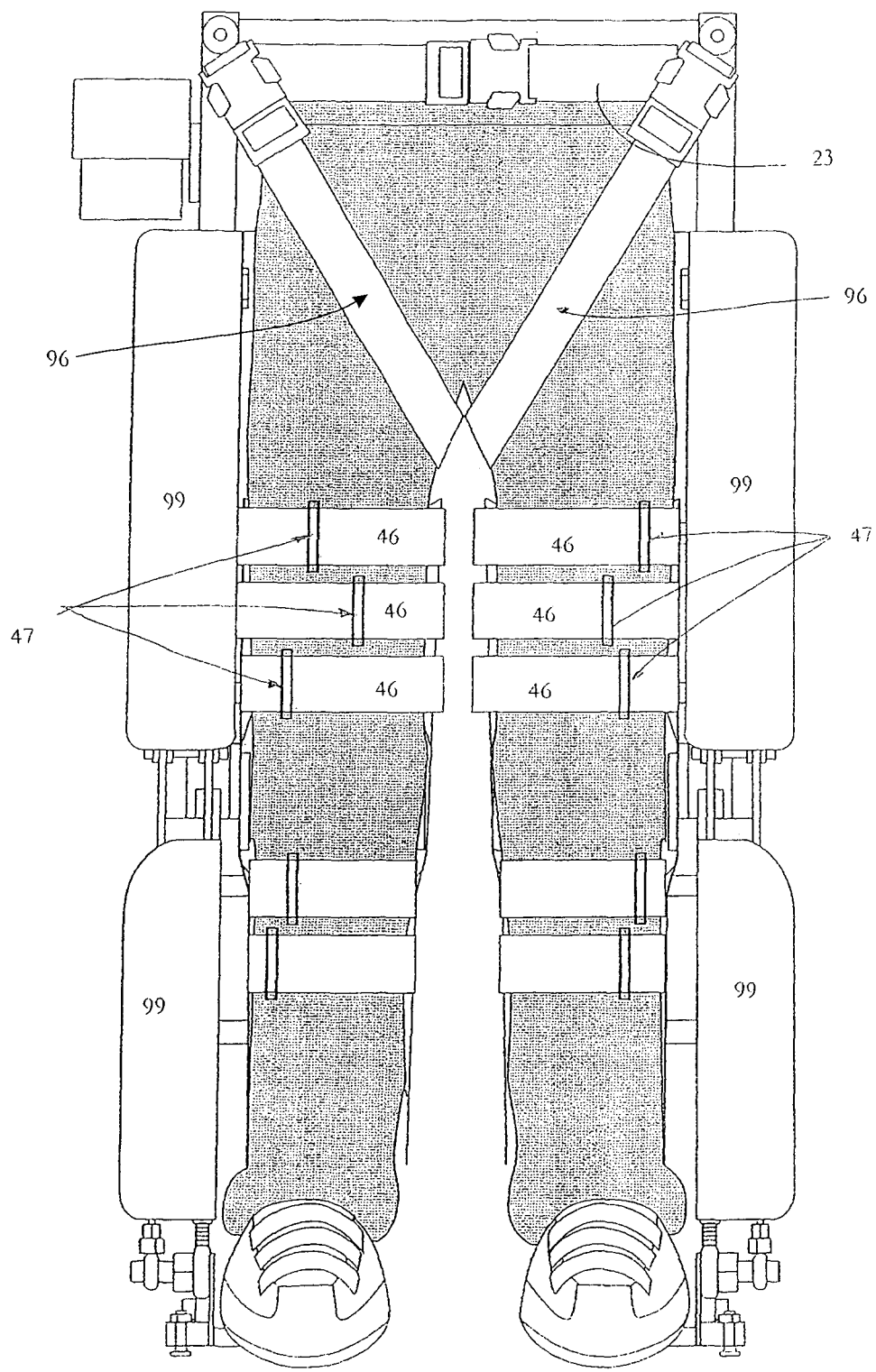
Figure 26:
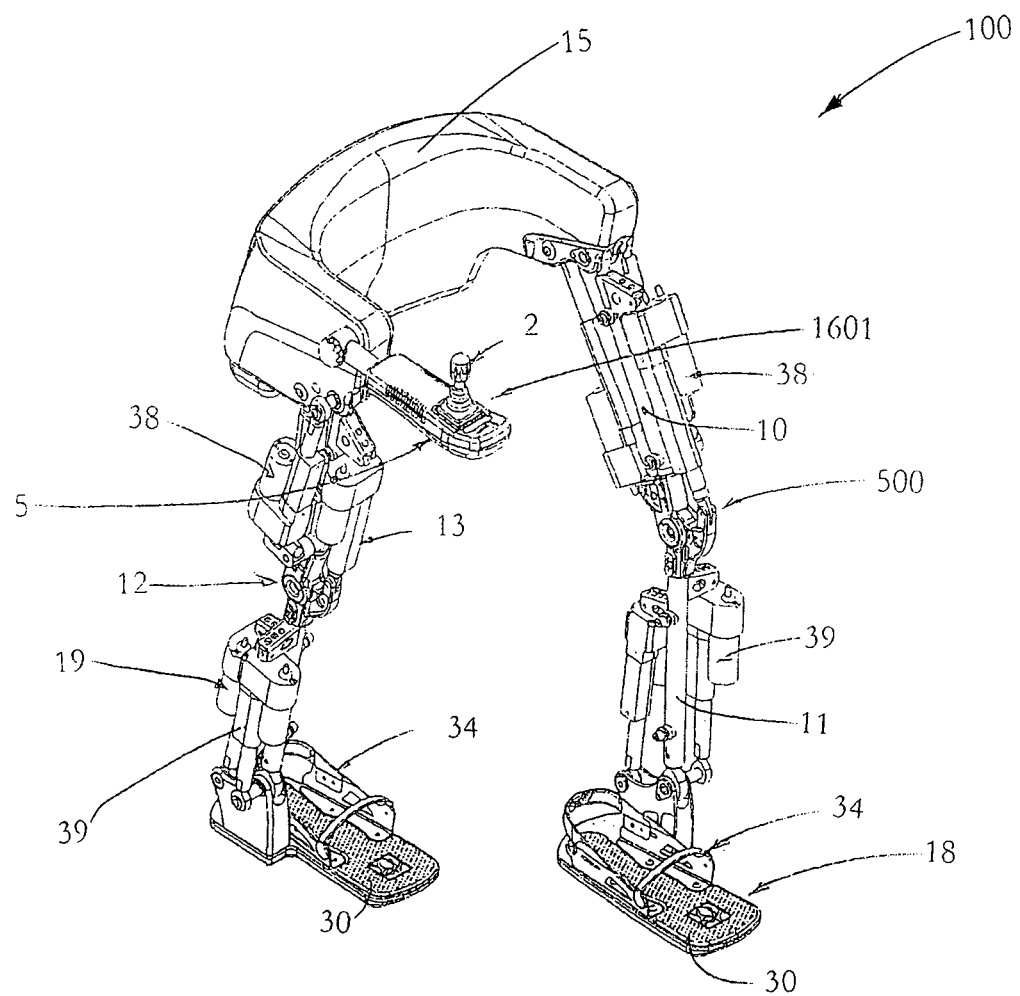
FIG. 26 shows a perspective front view of a third embodiment of the WA in a stepping position.
Figure 27:
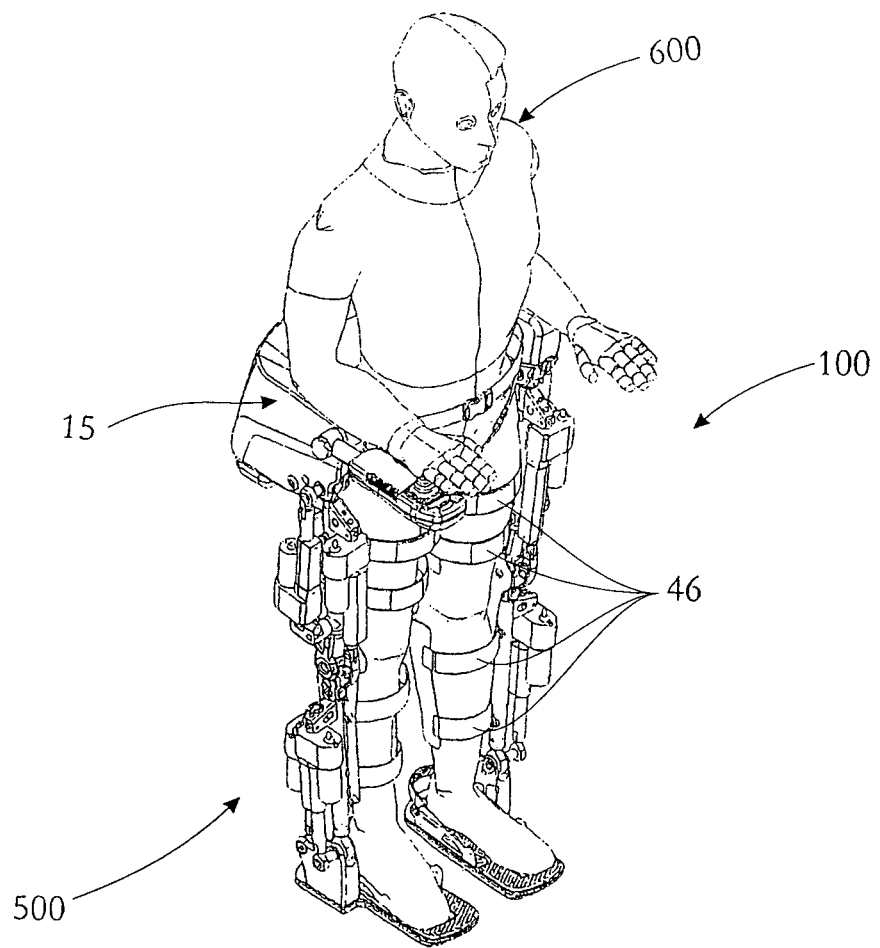
FIG. 27 shows a perspective front view of the third embodiment of the WA supporting a user in a standing position.
Figure 28:
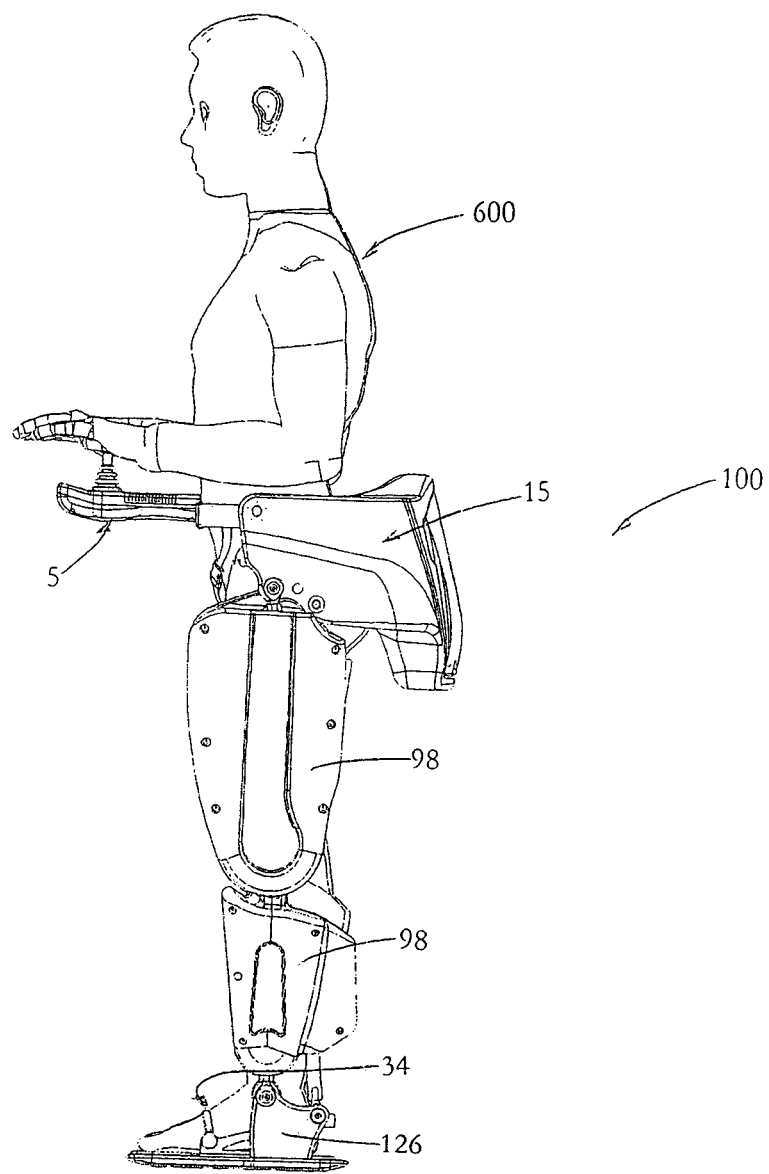
FIG. 28 shows a side view of the third embodiment of the WA supporting a user in a standing position.
Figure 29:
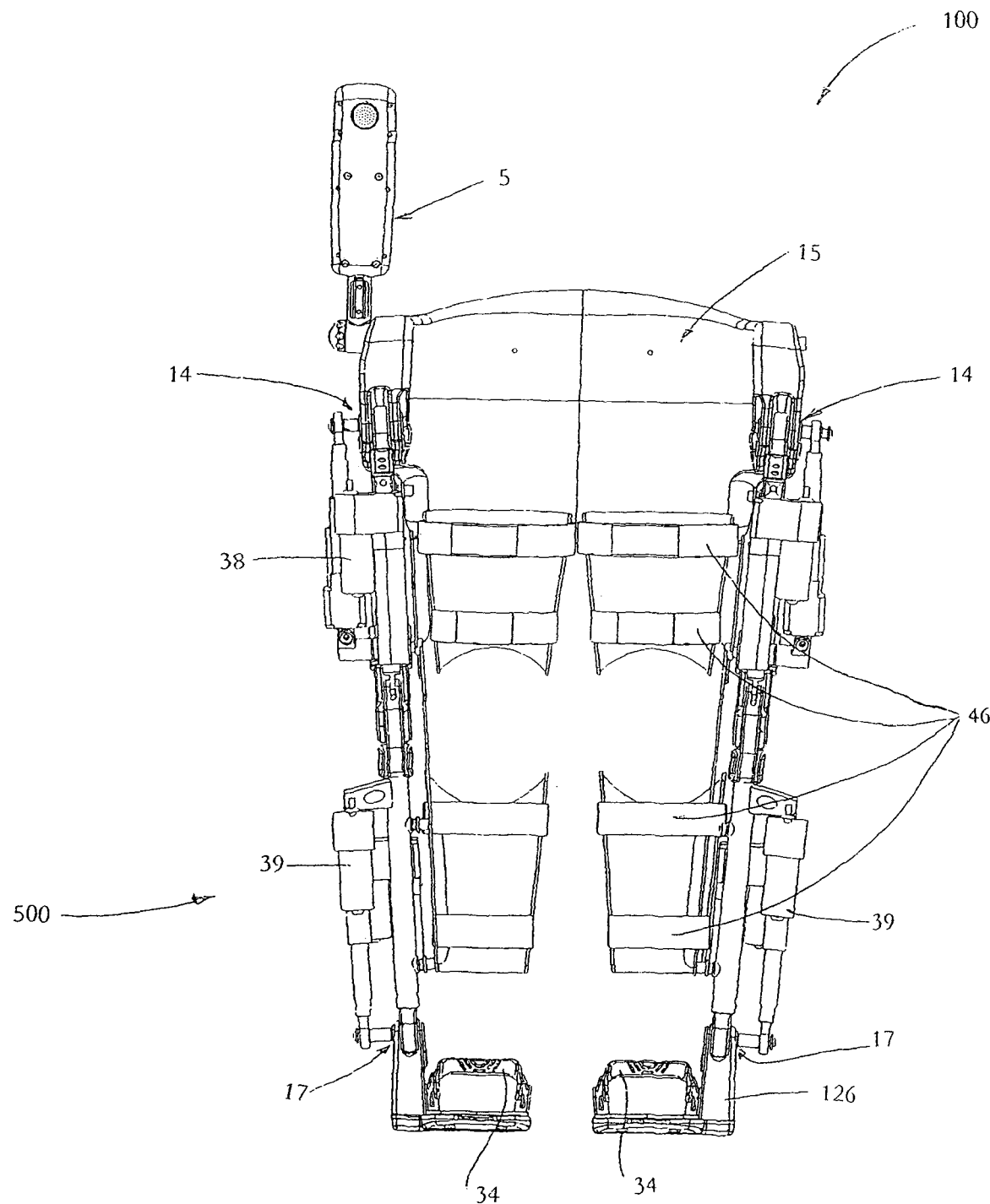
FIG. 29 shows a front view of the third embodiment of the WA.
Figure 30:
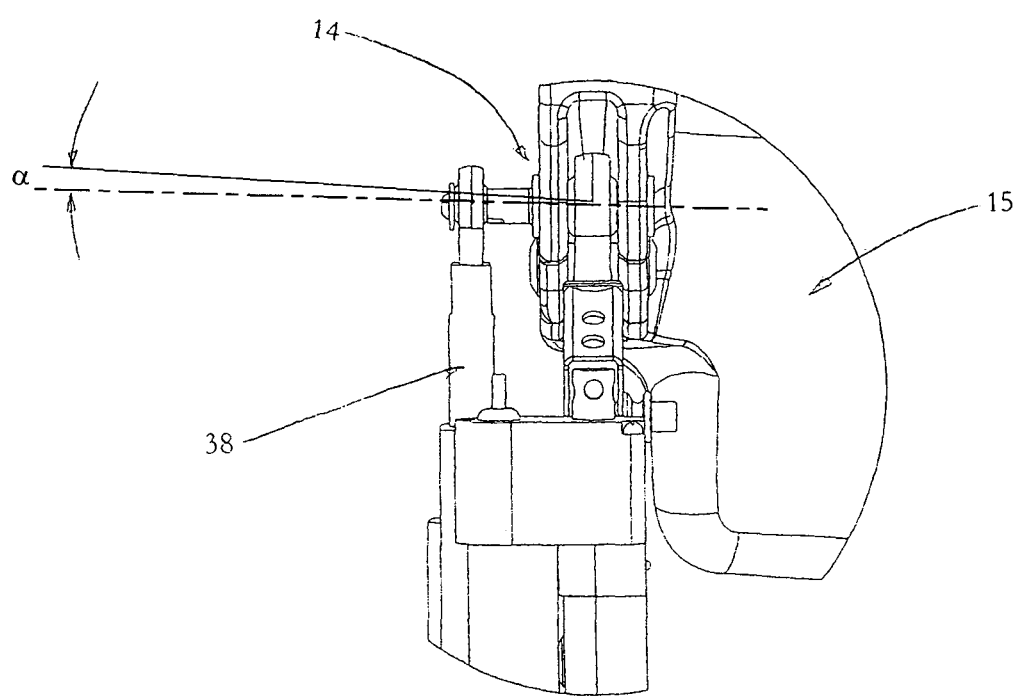
FIG. 30 shows a rear view of a region near the hip joint of FIG. 26.
Figure 31:
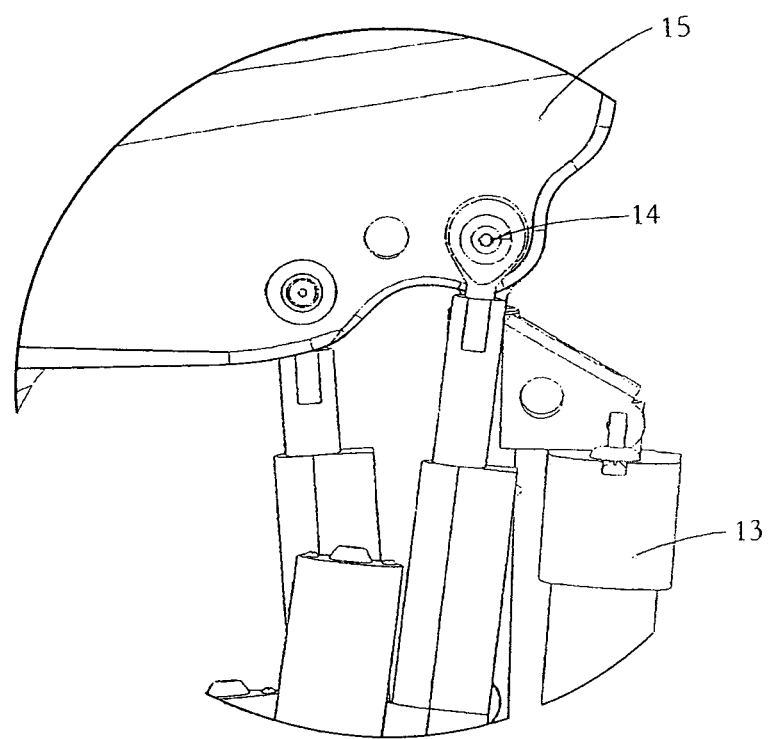
FIG. 31 shows a side view of a region near the hip joint of FIG. 26.
Figure 32:
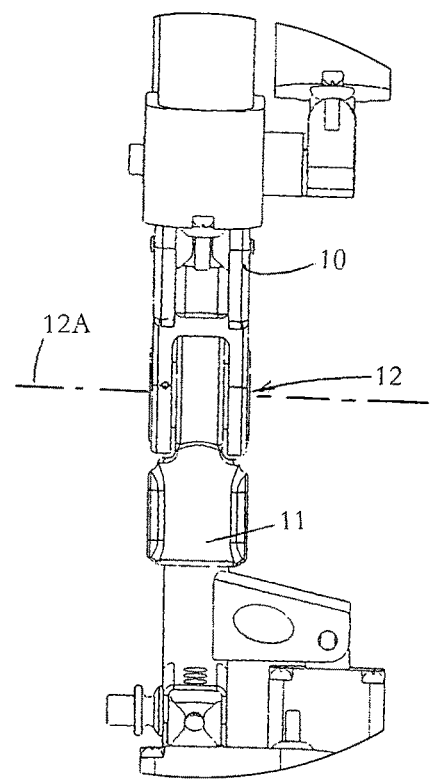
FIG. 32 shows a rear view of a region near the knee joint of FIG. 26.
Figure 33:
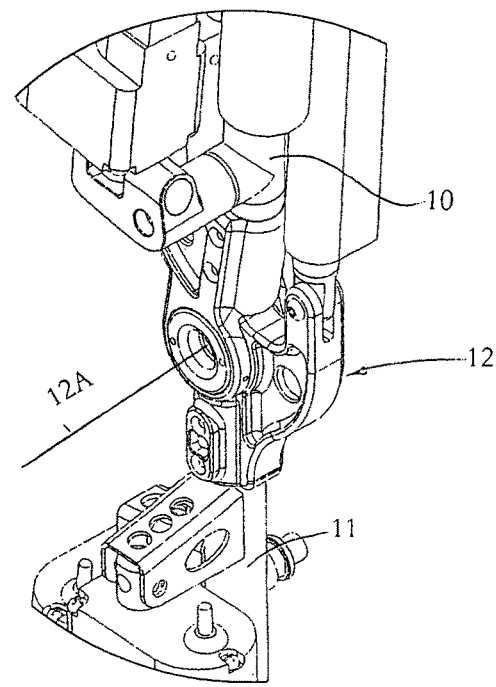
FIG. 33 shows a perspective front view of a knee joint of FIG. 26.
Figure 34:
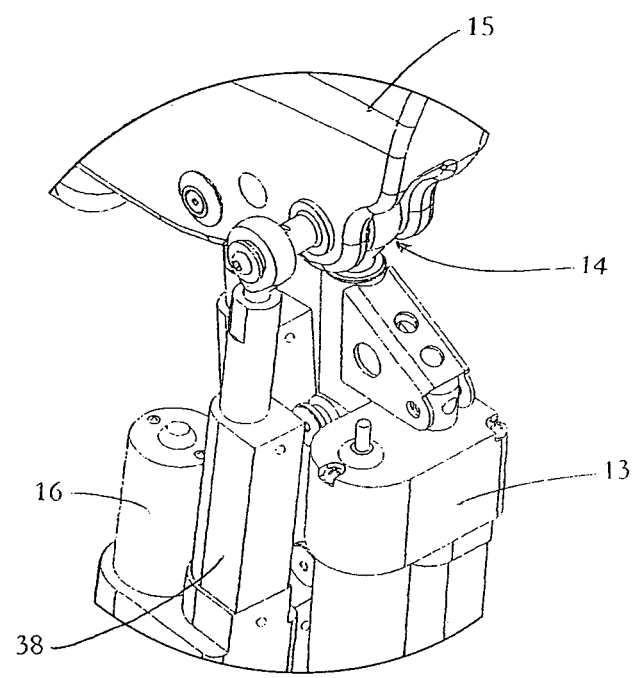
FIG. 34 shows a perspective front view of a region near the hip joint of FIG. 26.
Figure 35:
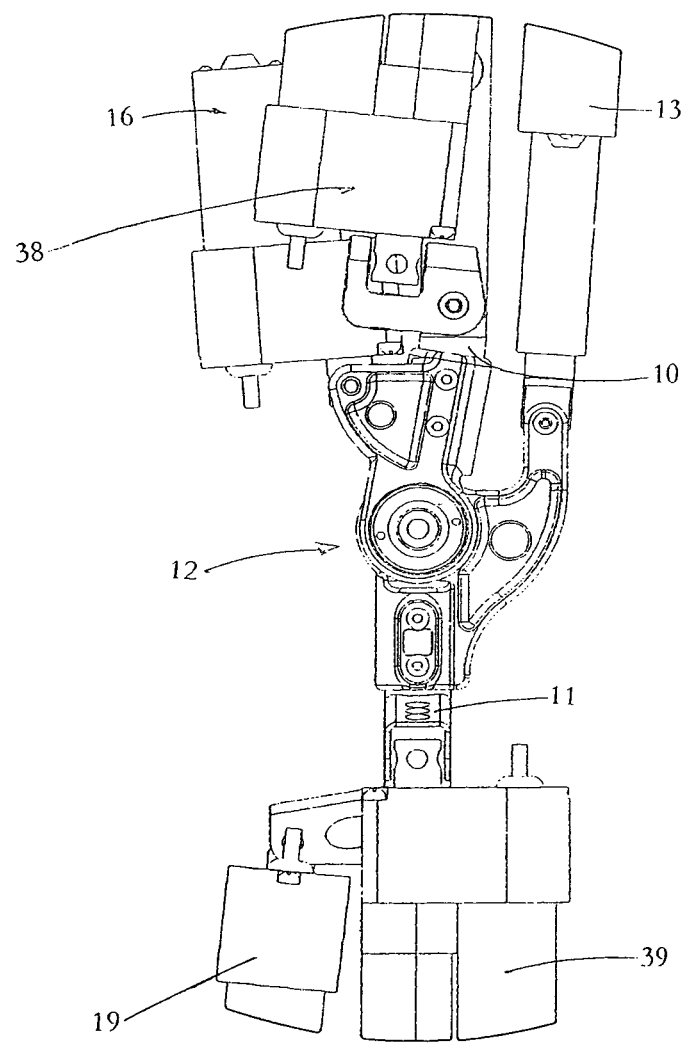
FIG. 35 shows a side view of a region near the knee joint of FIG. 26.
Figure 36:
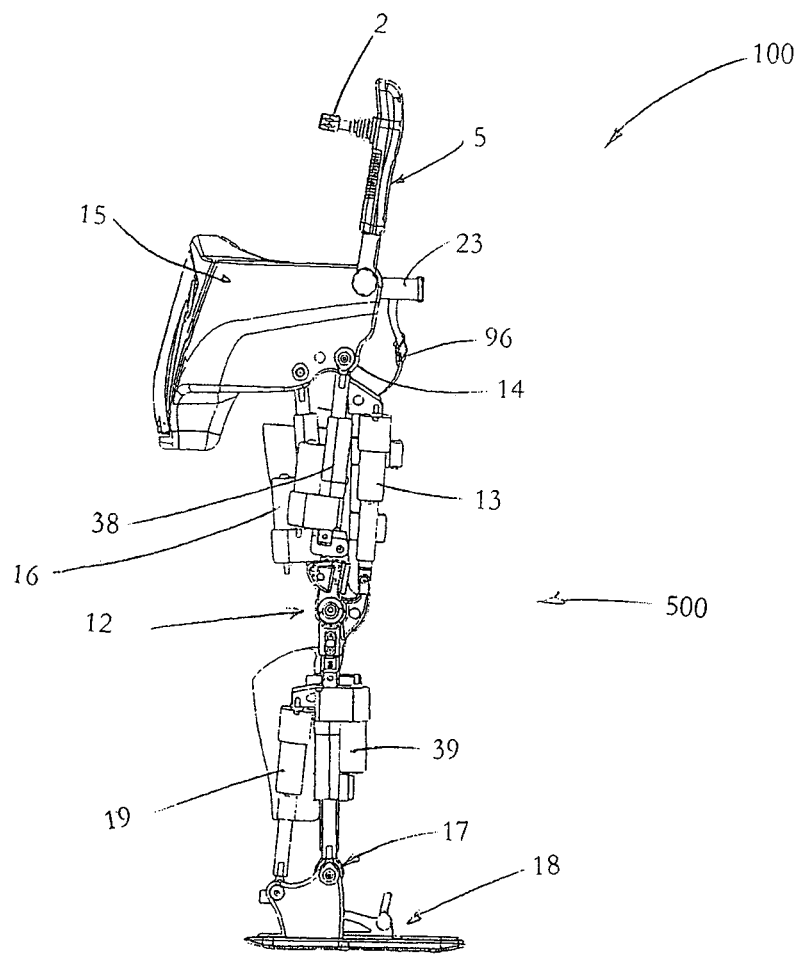
Figure 37:
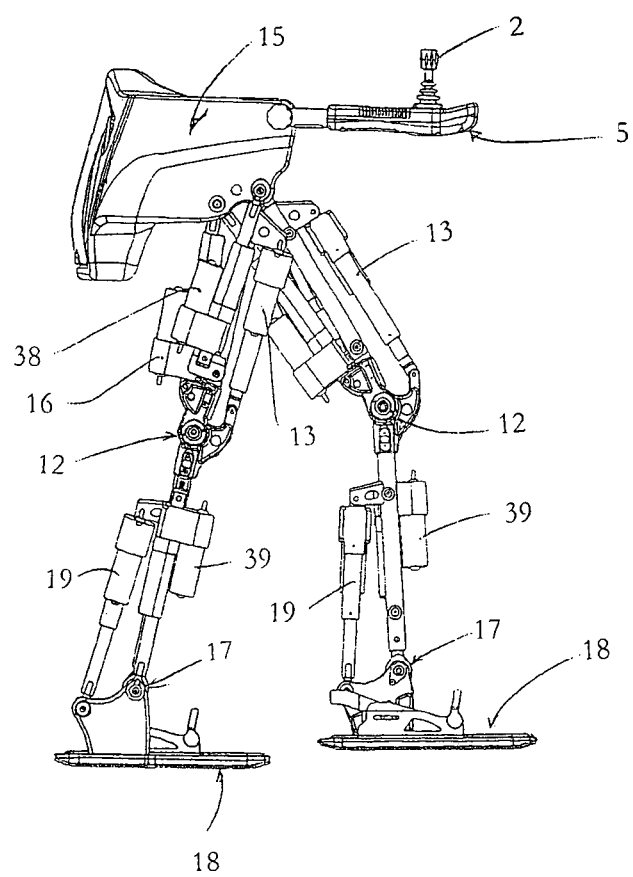
Figure 38:
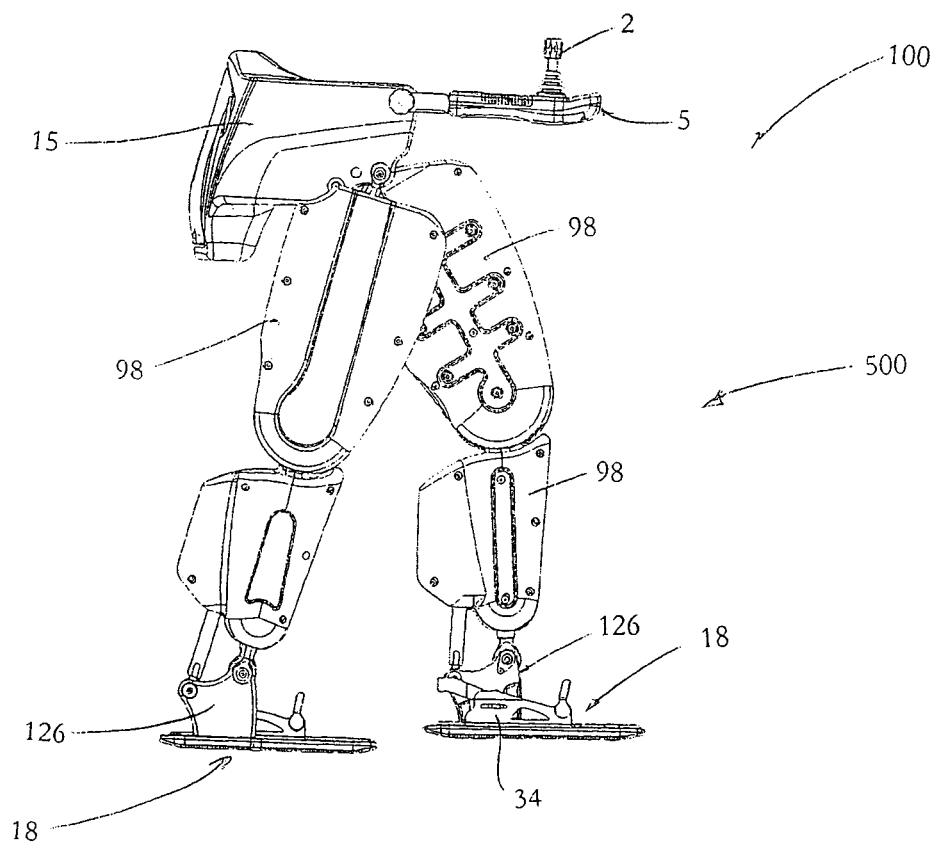

With reference to FIG. 16 there is shown an additional aspect of the WA of the present invention making the device suitable for users with lack of upper body strength and or function.

There may be provided one or more torso harnesses or upper body braces 92 that is attached to the hip frame 15. The upper body brace 92 can be provided for users 600 that have limited upper body control. This upper body brace 92 may include a frame or corset that is actuated to move the user's upper body 640 to help with their balance. In one embodiment (not shown), the torso harness 92 can be connected to the pelvic harness 96. Some or all of the components of the exoskeleton 500 may be fully or partially covered by covers 98 (as shown in FIGS. 14, 23, 25 and 38). These covers 98 are provided for safety, waterproofing, dust-proofing and aesthetic purposes and said covers 98 will be of sufficient strength and stability to allow the user 600 to transfer into and out of the WA by using the covers for support. In one embodiment, handles may be built into the covers 98, to facilitate transfer of the user 600 to and from the exoskeleton 500.

Figure 39:
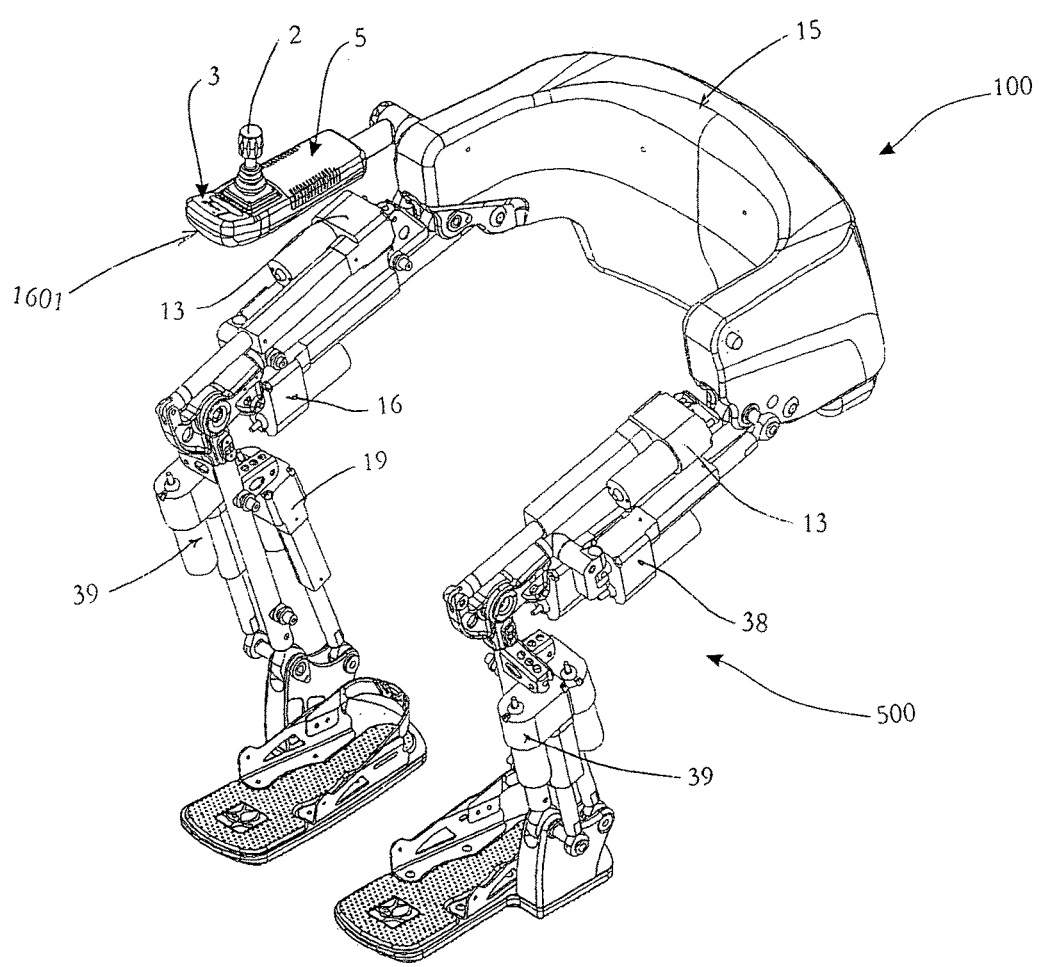
Figure 40:
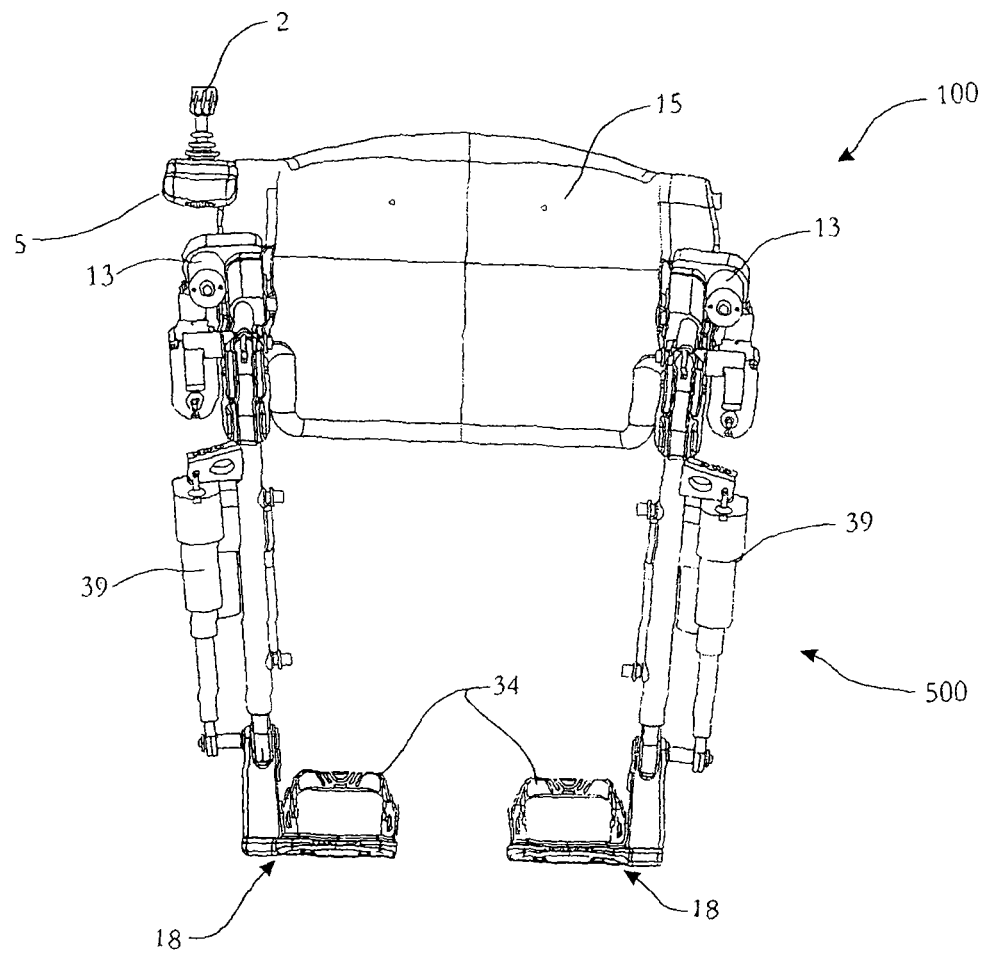
Figure 41:
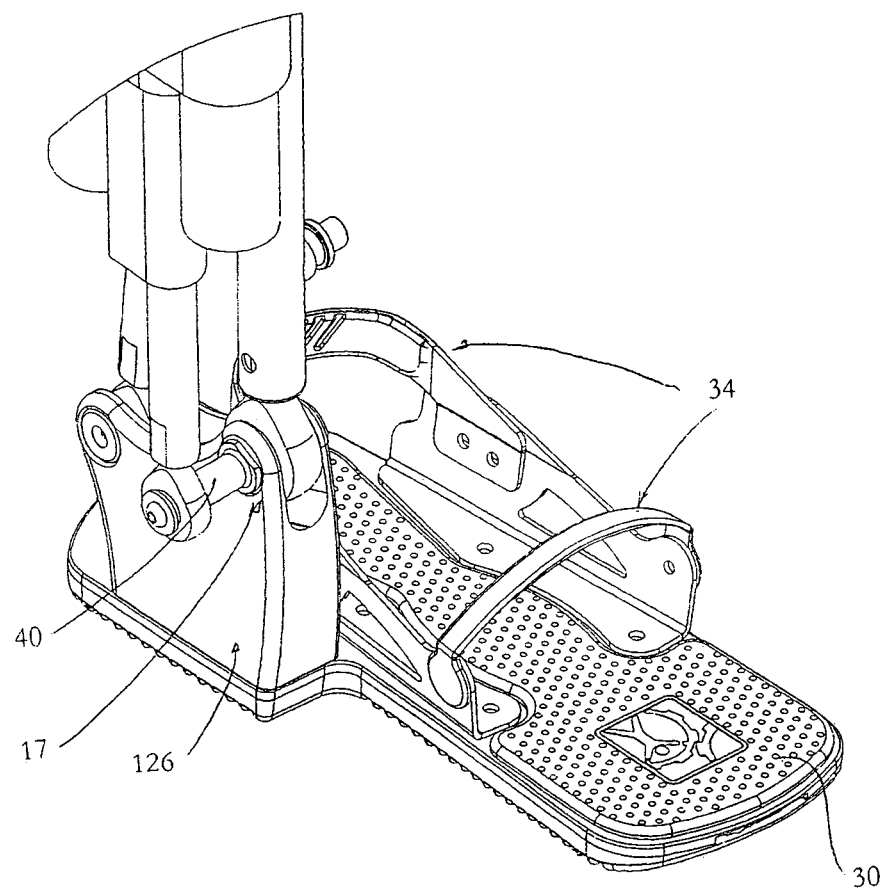
FIG. 41 shows a front perspective view of a region near the foot joint of a WA.
Figure 42:
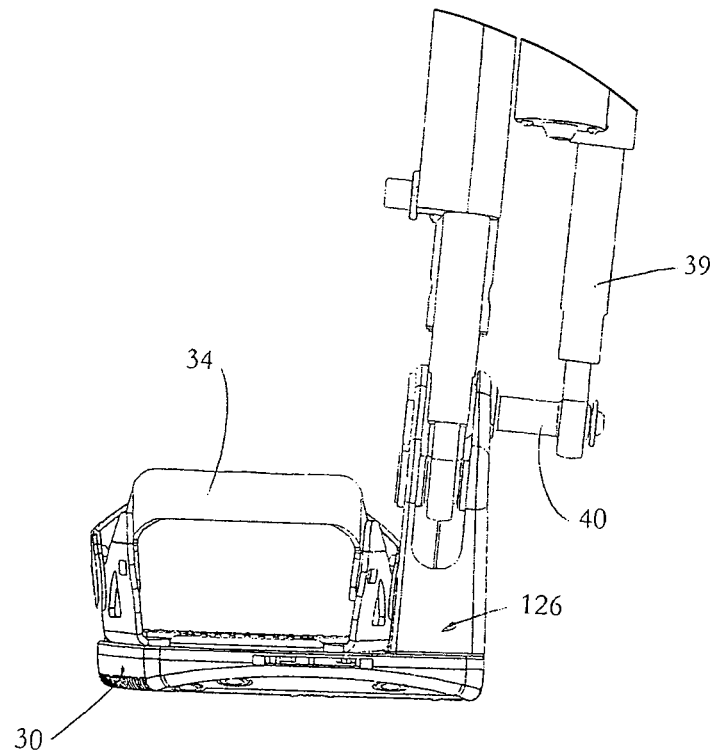
FIG. 42 shows a front view of a region near the foot joint of a WA.

In one embodiment, the exoskeleton 500 is configurable to a seated position (as shown in FIGS. 39 and 40). For example, when the exoskeleton 500 is in a seated position, the surfaces 99 of the covers (e.g. shown in FIG. 23, but not in the seated position) will extend substantially horizontally. The WA 100, located on a seat will then give the user a rigid surface to rely on for the purposes of their transfer into and out of the device. As such the covers 98 are preferably engaged to the exoskeleton in a rigid manner and in a manner that ensures they are stable relative thereto. The covers 98 may also (or instead) include functional shape features that can offer hand holds to the user for similar purposes.

With the use of orthotic support, a user is very limited or prevented from movement relative to the exoskeleton structure. A person is unable to rotate their leg relative to the exoskeleton structure and prevent it from longitudinally or laterally moving their leg relative to the exoskeleton structure.

Referring to FIG. 10, in one embodiment, each foot member 18 is provided with one or more contact sensors such as tactile sensors or pressure sensors (or both) on its sole. These sensors are configurable for providing information to the control system for facilitating the control of movement of the exoskeleton 500. They will typically do this by sensing a particular characteristic to be sensed and generating a signal indicative of that characteristic, and transmitting the signal to the control system for facilitating the control of movement of the exoskeleton 500. For example, the tactile or pressure sensors feed contact information to the terrain subsystem of the control system and the pressure sensors alternatively/additionally feed information to the balance subsystem of the control system, which will be explained in more detail later.

In the preferred form, the sole of each foot member is provided with four tactile sensors 66,67,68,69, each of which is located at or toward a respective corner region of the sole. For example, each foot member comprises a front left tactile sensor 66, front right tactile sensor 67, back left tactile sensor 68, and a back right tactile sensor 69. Each tactile sensor comprises at least one tactile or contact switch that is arranged to trigger when its respective corner of the sole contacts the ground surface. In the preferred form shown, each tactile sensor is formed collectively by three separate tactile switches wired in parallel. It will be appreciated that each tactile sensor may operate with only one tactile switch, but using multiple switches wired in parallel provides redundancy in case of switch faults or malfunctions. Similarly, each foot member is also provided with four pressure sensors, one in each corner region of the sole of the foot. In the preferred form, each pressure sensor is mounted behind a respective tactile sensor. These pressure sensors are arranged to detect the degree of pressure being applied by its respective corner region of the foot member 18 to the surface, or even the pressure variation applied to the ground across the bottom of the foot member 18. In the preferred embodiment, the tactile and pressure sensors on the foot member 18 are sealed by a waterproof cover (not shown).

In an alternative form only pressure sensors are provided (i.e. no tactile sensors) which provide both of the required contact signals (trigger upon contact with the ground surface) and pressure signals (degree of pressure at the respective region) to the control system and in particular to the terrain and balance subsystems of the control system respectively (as will be described in more detail further).

In the preferred form shown in FIG. 10, the sole of the foot member 18 also comprises one or more middle region contact sensors 71,72 that are arranged to trigger when they contact the ground or terrain underneath. The middle region contact sensors 71,72 comprise at least one tactile or pressure sensor, and are preferably formed by a series or row of three tactile or pressure sensors that are wired in parallel. The two middle region contact sensors 71,72 are preferably located substantially along the central longitudinal axis of the foot member. In the preferred form, one contact sensor 71 is provided in the back half of the sole relative to the central transverse axis AA, and the other contact sensor 72 is provided in the front half of the sole. In operation, the sensor outputs of the middle region contact sensors provided the terrain subsystem with additional resolution as to the contact distribution and alignment of the sole of the foot member with the terrain underneath. This additional contact information may be utilised by the terrain subsystem to assist in adjusting the exoskeleton movement sequences to conform to the terrain underneath, particularly at transitions between inclined terrain to flat terrain and flat terrain to declined terrain. In particular, the additional contract information provided by the middle region contact sensors is utilised by the terrain subsystem to help determine the extent to which the foot member is through a terrain transition, ie whether there is still more inclined terrain under the foot than flat terrain in an inclined-flat terrain transition for example, or whether there is more flat terrain under the foot such that it is almost through the transition. The same information can be obtained for a flat-declined terrain transition. It will be appreciated that the middle region contact sensors 71,72 are not essential to the control system, but do provide additional foot contact information and resolution for applications where terrain transitions are likely to be frequent.

The WA may also include seat sensors (not shown) for detecting forces applied by a user to the WA. It is envisaged that these could be in the form of a strain gauge (not shown) or the like. Two of these may exist at the rear of the WA 100, one in each "thigh" region.

It is envisaged that the WA control system (not shown) is configured to receive user input via a human interface device 1601 through which a human interface with the control system and may input information and receive information through sensory signals such as sound, light or vibration. Some examples of such a human interface device are a control pad (not shown), a keypad 3, a joystick 2, a touch screen/LCD screen or the like.

The control system includes a human interface device 1601. As described, various sensors, including sensors in the actuators are configurable to provide feedback signals which can be used by the control system for facilitating the control of the actuators.

In the preferred embodiment a control pad 4 will be used for human-machine interfacing. The control pad will be pivotable on a swing arm 5. It is envisaged that in one embodiment, the control pad 7 contains a membrane keypad (3), light emitting diode (LED) lights (not shown), a joystick 2 and a battery meter (not shown). Other suitable human machine interfacing controls may be used. For example a touch screen (not shown) may replace the control pad.

The keypad 3 of the preferred embodiment may further include an audible buzzer to indicate warnings and the selection of inputs and/or functions of the control system. It is envisaged that the LEDs can be used for a wide variety of functions, including fault indication, to indicate charging of the power supply, or to indicate that the emergency power supply (not shown) is being used. The LEDs can also be used as a battery meter to provide an indication of the available power in the main battery pack, ranging from all LEDs lit up meaning the battery is fully charged to no LEDs lit up meaning the battery needs charging.

In an alternative embodiment an LCD screen is provided to replace the LED indicators and display appropriate device status information such as the battery meter and other abovementioned indications.

The joystick 2 will be used as a user input means to input control instructions to the control system.

The WA is powered by on-board battery packs (not shown). In the preferred embodiment, the battery packs are located at the back of the hip frame. Alternatively they may be located at the 'kidneys' in the hip frame and at the front of the 'shins' in the leg covers 98. The battery system is a low voltage DC system and the battery packs are rechargeable from domestic power supply or vehicle power supplies. At least the actuators require power from the battery packs in order to allow them to actuate. The battery packs are removable for quick replacement with another battery pack of similar capacity or extended capacity. The battery packs can be charged on-board the WA or externally in the specifically designed charger.

Typically only a section of the battery packs will be used and in the event of these being depleted an audible alarm will sound as well as a visual battery charge indicator on the control panel will alert the user of the low battery power situation, the WA will then be able to automatically switch the power over to the reserve battery portion. Alternately, and in another preferred embodiment, the control panel will merely alert the user of a low power situation, and no reserve battery packs will be provided to conserve weight. It is envisaged that the WA 100 will assist in restoring basic mobility to a disabled user.

The WA is self contained with on board power and control systems and can be recharged using an in car charger or domestic power supply.

Control System of WA

A preferred form of the control system of the WA will now be described with reference to FIGS. 45a-73. By way of example, the control system will be explained with reference to the preferred embodiments of the exoskeleton that were described with reference to FIGS. 1-44. However, it will be appreciated that the control system configuration, methods and techniques, and in particular the terrain and balance subsystems, could be adapted and applied to other mobility aid and exoskeleton systems that have similar control functionality and stability requirements.

It will be appreciated that the control system may be implemented on any suitable hardware system, platform or architecture. The hardware system is provided on-board the WA and preferably comprises at least a processor for running the control system algorithms, memory for storing control system algorithms and data, and interface circuitry for communicating with and operating other WA components, such as receiving sensor signals and operating exoskeleton actuators. It will be appreciated that the processor may be any form of programmable hardware device, whether a CPU, Digital Signal Processor, Field-Programmable Gate Array, Microcontroller, Application-Specific Integrated Circuit, or the like.

The control system controls the behaviour and movement of the actuators of the exoskeleton based on user input via the human device interface and sensor inputs which detect WA balancing and environmental factors such as terrain change. When powered, the WA control system remains in an idle state maintaining its current position and awaiting user input via the control pad. The user input is converted to a set of command values that trigger a pre-programmed sequence of movements of the actuators via an actuator controller such as a set of motor controllers. The preferred form control system stores a series of pre-programmed sequences, each sequence being configured to effect a different movement, such as, but not exclusively, walking, sitting, and standing. Each pre-programmed sequence may be interrupted and adjusted by environmental variables from separate balance and terrain sensing sub-systems, which are arranged to alter the pre-programmed sequence to adjust to its current environment.

The pre-programmed sequence is driven to an event or sequence of events/instructions which is determined as being completed by the physical positions of the actuators and or appropriate signals from the environmental sensors. By having pre-programmed time and position sequences and adjusting for the environment, computational time and power is saved.

Figure 73:
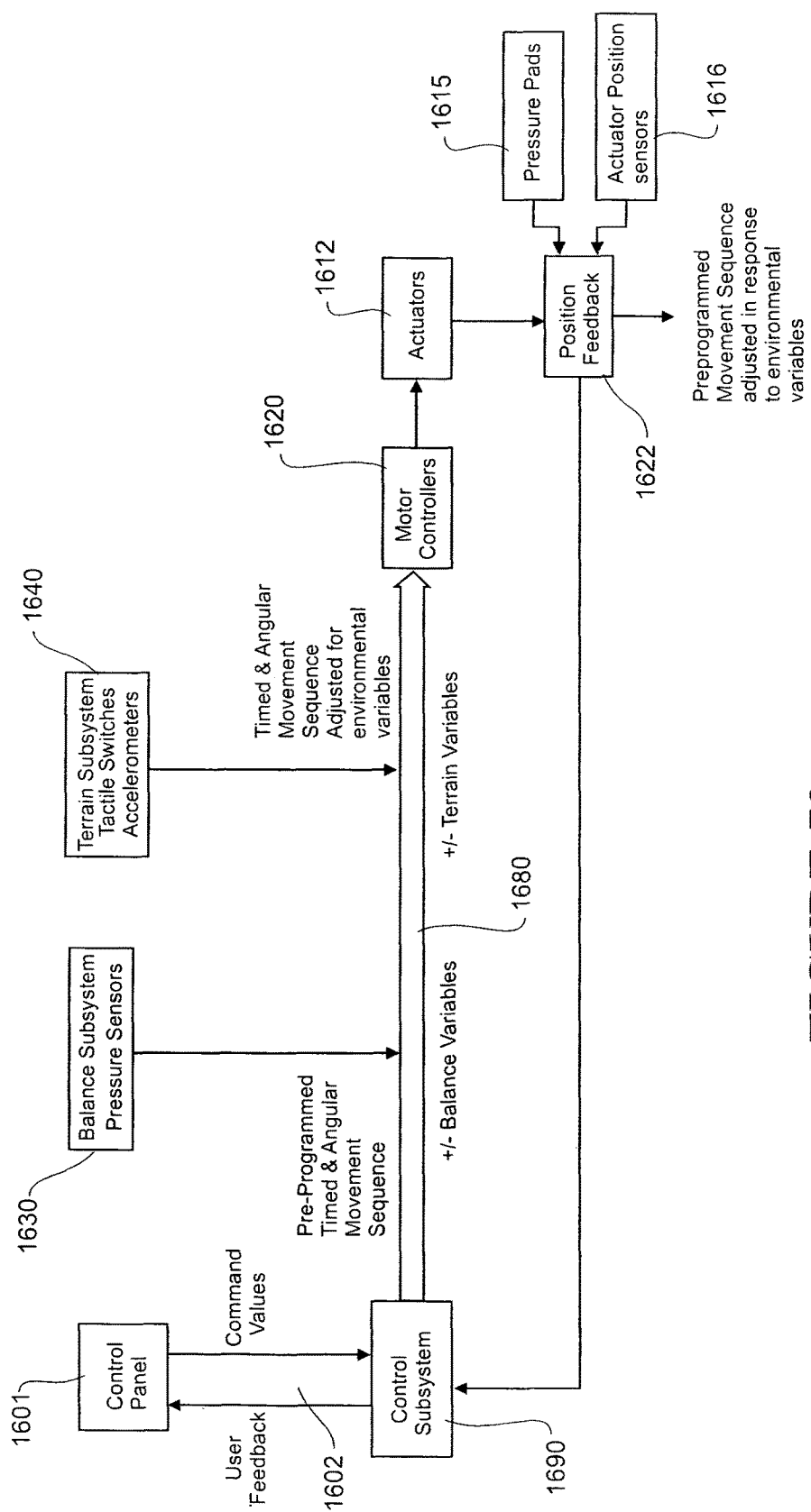
FIG. 73 shows an overview schematic diagram of the control system in accordance with a preferred form of WA.

With reference to FIG. 73, the preferred form control system comprises a human machine interface 1601, a terrain sensing subsystem 1640, a balance subsystem 1630, and a motor control subsystem 1620. The motor control subsystem (i.e. the actuator controller) is connected to the actuators 1612. Various sensors 1610, 1611, including sensors in the actuators 1612 provide feedback, such as the position of the actuators.

User input via the control panel 1601 is converted into a pre-programmed command by the control system 1690. The pre-programmed commands instruct the motor controllers 1620 to move the actuators 1612. Actuator sensors 1616 provide feedback to the control system to ensure correct movement of the actuators. The pre-programmed commands may be altered by the balance subsystem 1630 and/or the terrain subsystem 1640 depending on sensor inputs. Each sub-system operates separately from the other subsystems but communication between the sub-systems can be made via a network or bus for example.

The various subsystems and examples of pre-programmed commands will be described below in more detail.

Human Machine Interface

In the preferred embodiment a control pad will be used for human machine interfacing, it contains twelve membrane keypad buttons, three LEDs, a joystick and a battery meter. Other suitable human machine interfacing controls may be used. For example a touch screen may replace the control pad. In another alternative an LCD screen may replace the LED's and battery meter and display other suitable status information related to the device.

The keypad of the preferred embodiment contains an 'ON/OFF' button which will be used to turn the WA on and off, a 'Sit' button which will be used to make the WA sit down, a 'Stand' button which will be used to make the WA stand up and an 'Emergency battery supply' which will allow the emergency batteries to supply power to the WA once the main power supply has run out. There will be a cancel button to cancel the selected function. There will be a 'raise feet' and lower feet function for use in the seated position. There will be an audible buzzer to indicate warnings and the selection of certain functions.

The keypad contain three LEDs; one of the LEDs will blink at a constant rate when there is a fault in the WA, one of the LEDs will light up when the device is being charged and one LED will light up when the emergency power supply is being used.

The battery meter will be an array of LEDs and will provide an indication of the available power in the main battery pack, ranging from all LEDs lit up meaning the battery is fully charged to no LEDs lit up meaning the battery needs charging.

As mentioned for the alternative embodiment above, the LEDs could be replaced with an LCD screen that displays the information provided by the LEDs and in a similar or alternative manner.

The joystick will be used to control the walking motion of the WA. Selection and quick release of the joystick in the forwards or backwards direction will cause the WA to static step forwards or backwards respectively, while holding the joystick forwards or backwards for a longer period of time will cause the WA to do a dynamic step forwards or backwards respectively. Pushing the joystick to the left or right will cause the WA to step to the left or right respectively. Pushing the joystick diagonally forwards or backward and simultaneously left or right will cause the WA to turn in the corresponding direction.

Pre-programmed Commands/Sequences

The WA is controlled by the user through a human machine interface. As previously described the human machine interface of the preferred embodiment is a keypad. Performing an action on the keypad triggers a pre-programmed sequence of events. These sequences are timed, angular series of motion that constantly maintain the user in a balanced state, if this balanced state is upset be external environmental forces or even by the user movement the device subsystems interrupt and update the pre-programmed sequences with input variables to adjust for the environmental factors.

The pre-programmed sequences therefore assume a flat terrain, ie which is not sloped in either the longitudinal or transverse directions relative to the movement direction. Each pre-programmed movement sequence is associated with a number of sequential instructions required to perform the desired movement. The sequential instructions discretely mimic to some extent the movement steps required by the human joints to perform a particular movement sequence. Every instruction is associated with a certain set of relative actuator movements that perform the desired instruction. Therefore, the control system must store for every pre-programmed sequence, the instructions associated with that sequence and the actuator movements required for every instruction.

FIGS. 45a-49b provide examples of pre-programmed movement sequences, the instructions associated with these sequences, and the relative actuator movements required to perform those particular instructions. In the following examples, a model 700 of the exoskeleton 500 of FIGS. 1-44 is shown in a schematic form for clarity. The arrows shown correspond to movements of the actuators relative to the previous instruction (or movement from an upstanding controlled position in the case of the first instruction).

As discussed for the exoskeleton 500 of FIGS. 1-44, the joint angles of the exoskeleton are changed by varying the lengths of the actuators associated with the particular joint. Actuators 701-710 are therefore represented by arrows to show whether the actuators are lengthened or shortened during a particular instruction (which in turn varies the associated joint to perform the desired movement). Actuators 701-710 each correspond to one of actuators 19,39,13, 16 and 38 of exoskeleton 500 (associated with joints 17, 12 and 14) as shown in the table 1 below.

TABLE 1

| Model 700 Actuator | Corresponding Exoskeleton 500 Actuator |
| --- | --- |
| Actuator 701 | Main left foot actuator 19 |
| Actuator 702 | Main right foot actuator 19 |
| Actuator 703 | Secondary left foot actuator 39 |
| Actuator 704 | Secondary right foot actuator 39 |
| Actuator 705 | Left knee actuator 13 |
| Actuator 706 | Right knee actuator 13 |
| Actuator 707 | Main left hip actuator 16 |
| Actuator 708 | Main right hip actuator 16 |
| Actuator 709 | Secondary left hip actuator 38 |
| Actuator 710 | Secondary right hip actuator 38 |

For the example movement sequences of FIGS. 45-49 below, reference will be made to actuators 701-710 and in particular to their change in length as represented by the associated arrows of the drawings.

Walking—Static Step

A static step movement sequence is shown in FIGS. 45(*a*)-(*j*). A static step requires one step to be taken by each leg and results in the exoskeleton 700 standing in a controlled position (not leaning to the left or to the right) with both legs in line with (adjacent) one another. Before taking a step, the WA may check that it is in the standing position. The WA's and users combined centre of mass is firstly shifted to the side directly above one foot. The system will ensure the centre of mass is directly above the foot. The other leg is elevated and moved forward and then placed down on the ground in a position ahead of the first foot. The WA's and users combined centre of mass is next shifted to the side directly above the forward foot and then the other foot is raised and moved forward to a position in line with the first foot and is lowered to the ground in this position.

The particular example shown in FIG. 45 shows the right leg leading the static step. It will be appreciated that a similar programmed sequence for a leading left leg movement can also be stored by the system by simply changing the order of some of the instructions. Furthermore, the example shown is for a forward step and it will be appreciated that a backwards step could also be pre-programmed by varying the instructions accordingly as will be inherently apparent to a person skilled in the art.

The following instructions are therefore stored for the static step programmed sequence (forward step with right leg leading) of FIG. 45:

i) lean the exoskeleton 700 to the left (FIG. 45(*a*)),
ii) tilt the pelvis to the left (FIG. 45(*b*)),
iii) raise the right leg and move it forwards (FIG. 45(*c*)),
iv) lower the right leg down onto the ground surface (FIG. 45(*d*)) so that the right leg is ahead of the left leg,
v) transfer the weight of the exoskeleton 700 (with the user in it) to the right to position the exoskeleton 700 is in a controlled position (FIG. 45(*e*)),
vi) continue to transfer the weight to the right to position the exoskeleton 700 is in a right position (FIG. 45(*f*),
vii) tilt the pelvis of the exoskeleton 700 to the right (FIG. 45(*g*)),
viii) raise the left leg and move it forwards (FIG. 45(*h*)),
ix) lower the left leg down onto the ground surface (FIG. 45(*i*)) so that the left leg is adjacent the right leg, and
x) transfer the weight of the exoskeleton 700 (with the user in it) to the left to position the exoskeleton 700 in a controlled position (FIG. 45(*j*)).

The system onboard memory would therefore store relative actuator movements for each of the above instructions against each movement sequence. Only those actuators that change length are shown in FIGS. 45(a)-(j). A double ended arrow represents an increase in length/expansion of the associated actuator, and two arrows facing one another represent a shortening in length/compaction of the associated actuator. For example to effect a left lean instruction (i) for the static step movement sequence, actuators 701-710 need to move relative to their controlled position/standing state (i.e. the state reached after the instruction shown in FIG. 45(j) for example) by:

lengthening actuators 701, 702, 704, 706 and 709,
shortening actuators 703, 705, 707, 708 and 710.

Similarly the rest of the instructions (ii)-(x) above of the static step sequence require actuator movements (relative to the resulting lengths of the actuators from the previous instruction) as shown in FIGS. 45(b)-(j).

By way of example only, table 2 below shows relative changes in lengths of the ten actuators 701-710 during the static step movement sequence of FIG. 45. Variables indicative of these length changes will be stored against each instruction and sent to the motor control system with each sequential instruction call when a static step movement sequence is initiated, by the user via the user interface for example.

A negative value in Table 2 indicates a shortening of an actuator relative to its length at the end of a previous instruction, and a positive value indicates a lengthening of the actuator (also relative to its length at the end of a previous instruction).

down on the ground in a position ahead of the first foot. The WA's and the user's combined centre of mass is next shifted to the side directly above the forward foot and then the other foot is raised and moved forward to a position ahead of the first foot and is lowered to the ground in this position. This sequence is repeated while the user holds the joystick in the appropriate command position, when the joystick is released, the next footfall is made in line with (adjacent) the forward foot bringing the user to a halted standing position with both feet in line.

The left dynamic step as shown in FIGS. 46(a)-(e) comprises the following set of sequential instructions:
(i) Transfer the weight of the exoskeleton 700 (with the user in it) to the left to position the exoskeleton 700 in a left lean position (FIG. 46(a)),
(ii) Tilt the pelvis of the exoskeleton 700 to the left (FIG. 46(b)),
(iii) raise the right leg and move it forwards (FIG. 46(c)),
(iv) lower the right leg down onto the ground surface (FIG. 46(d)) so that the right leg is ahead of the left leg,
(v) transfer the weight of the exoskeleton 700 (with the user in it) to the right to position the exoskeleton 700 is in a controlled position (FIG. 46(e)), FIGS. 46(a)-(e) show the relative actuator movements required for effecting the above left dynamic instructions (i)-(v) respectively.

The right dynamic step as shown in FIGS. 47(a)-(e) comprises the following set of sequential instructions:
(i) transfer the weight to the right to position the exoskeleton 700 is in a right position (FIG. 47(a)),

TABLE 2

Relative Actuator Movements Starting from Standing (mm)

| Actuator | | 701/L Ankle | 702/R Ankle | 703/L Side Ankle | 704/R Side Ankle | 705/L Knee | 706/R Knee | 707/L Hip | 708/R Hip | 709/L Side Hip | 7010/R Side Hip |
|---|---|---|---|---|---|---|---|---|---|---|---|
| | | | | Starting at the standing controlled position | | | | | | | |
| 45(a) | Left Lean | 3 | 8 | −10 | 8 | −4 | 12 | 0 | 7 | 7 | −8 |
| 45(b) | Pelvic Tilt to Left | 2 | 4 | 0 | −2 | −2 | 22 | 0 | 16 | −10 | 8 |
| 45(c) | Right Leg Forward | 0 | 0 | 0 | 0 | 0 | −10 | 0 | 4 | 0 | 0 |
| 45(d) | Right Leg Down | 0 | −18 | 0 | 0 | 0 | −17 | 0 | −12 | 8 | −8 |
| 45(e) | Weight Transfer to the right and forward (ending in a control position) | 6 | −4 | 10 | −7 | 5 | −9 | −5 | −5 | −5 | 8 |
| 45(f) | Weight Transfer to the right and forward (ending in a right lean position) | 7 | 11 | 10 | −7 | 3 | −2 | −5 | −9 | −8 | 8 |
| 45(g) | Pelvic Tilt to Right | 3 | 0 | 0 | −3 | 0 | 0 | 5 | 0 | 11 | −8 |
| 45(h) | Left Leg Forward | −10 | 0 | 0 | 0 | 13 | 0 | 15 | 0 | 0 | 0 |
| 45(i) | Left Leg Down | −14 | 16 | 0 | 0 | −20 | 31 | −12 | 14 | −3 | 0 |
| 45(j) | Straitening | 3 | −17 | −10 | 11 | 5 | −27 | 2 | −15 | 0 | 0 |

Walking—Dynamic Step

A left dynamic step movement sequence is shown in FIGS. 46(a)-(e) and a right dynamic step movement sequence is shown in FIGS. 47(a)-(e). The dynamic step sequence is used when a user wants to continuously walk rather than take a single step (the user may command this sequence by holding a joystick of the user interface in a forward position for example). The control system executes a dynamic step sequence by alternating between left and right dynamic steps.

Before taking a step, the WA may check that it is in the standing position. The WA's and the user's combined centre of mass is firstly shifted to the side directly above one foot. The other leg is elevated and moved forward and then placed (ii) tilt the pelvis of the exoskeleton 700 to the right (FIG. 47(b)),
(iii) raise the left leg and move it forwards (FIG. 47(c)),
(iv) lower the left leg down onto the ground surface (FIG. 47(d)) so that the left leg is adjacent the right leg, and
(v) transfer the weight of the exoskeleton 700 (with the user in it) to the left to position the exoskeleton 700 in a controlled position (FIG. 47(d)).

FIGS. 47(a)-(e) show the relative actuator movements required for effecting the above right dynamic instructions (i)-(v) respectively.

Table 3 on the next page shows an example of relative actuator length changes for one dynamic step sequence (a left dynamic step followed by a right dynamic step).

TABLE 3

Relative Actuator Movements Starting from Right Control Position (mm)

| Number on Movement Sequence | | 701/L Ankle | 702/R Ankle | 703/L Side Ankle | 704/R Side Ankle | 705/L Knee | 706/R Knee | 707/L Hip | 708/R Hip | 709/L Side Hip | 710/R Side Hip |
|---|---|---|---|---|---|---|---|---|---|---|---|
| | | | | Starting at Right Control Position | | | | | | | |
| 46(a) | Weight Transfer to the left and forward (ending in a left lean position) | 11 | 6 | −6 | 9 | −2 | 3 | −9 | −5 | 8 | −8 |
| 46(b) | Pelvic Tilt to Left | 0 | −4 | −4 | −2 | 0 | 32 | 0 | 30 | −11 | 10 |
| 46(c) | Right Leg Forward | 0 | 0 | 0 | 0 | 0 | 0 | 0 | 3 | 0 | 0 |
| 46(d) | Right Leg Down | 2 | −19 | 0 | 0 | 4 | −27 | −3 | −12 | 8 | −8 |
| 46(e) | Weight Transfer to the right and forward (ending in a control position) | 8 | −4 | 10 | −7 | 0 | −10 | 0 | −5 | −5 | 6 |
| 47(a) | Weight Transfer to the right and forward (ending in a right lean position) | 6 | 11 | 9 | −7 | 3 | −2 | −5 | −9 | −8 | 8 |
| 47(b) | Pelvic Tilt to Right | 0 | 1 | 0 | −3 | 0 | 0 | 0 | 0 | 11 | −11 |
| 47(c) | Left Leg Forward | −7 | −2 | 0 | 0 | 13 | 0 | 20 | 0 | −3 | 1 |
| 47(d) | Left Leg Down | −11 | 17 | −2 | 0 | −20 | 32 | −12 | 15 | 0 | 0 |
| 47(e) | Weight Transfer to the left and forward (ending in a left control position) | −9 | −6 | −7 | 10 | 2 | −28 | 9 | −17 | 0 | 2 |

Sitting

Before the sit sequence is activated the WA may check that it is in a standing position. When the user activates the sit sequence seat sensors may be activated. Actuators slowly lower the WA while keeping the WA's and users combined centre of mass directly above the feet to ensure stability. The WA is then slowly lowered until the rear cover/seat sensors make contact with the surface of the seat.

Figure 48A:
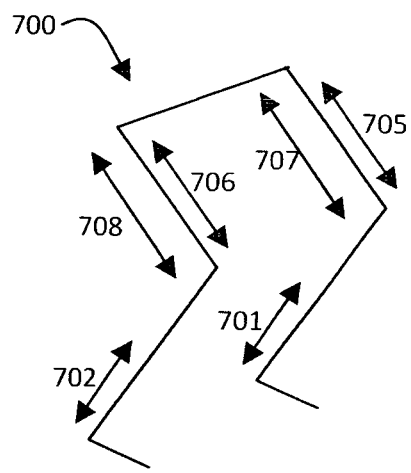
FIGS. 48*a* and 48*b* show the model of the exoskeleton undergoing a sitting movement sequence in accordance with a preferred form of the control system of the WA.
Figure 48B:
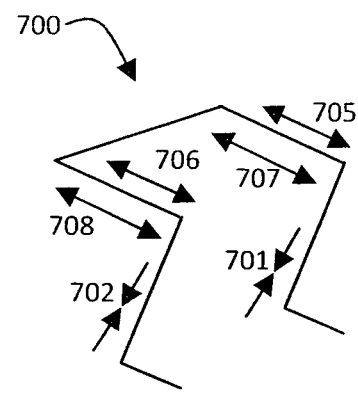

FIGS. 48(a) and 48(b) show the instructions associated with a sit command. These are:
 (i) Lowering of the centre of mass forward (FIG. 48(a)), and
 (ii) Shifting the centre of mass on the seat (ending in the sitting position of FIG. 48(b)).

Table 4 below shows the relative actuator movements (starting from a standing position) required for carrying out the sit sequence defined by instruction (i) and (ii) above.

Standing

Before the stand sequence is activated the WA may check that it is in a seated position. When the user activates the stand sequence the seat sensors may be activated. Actuators will be used to raise the user's thighs until the rear cover sensors are no longer in contact with the surface of the seat. Actuators will then be used to shift the WA's and the user's combined centre of mass directly above the user's feet. The WA will then straighten out into a standing position while keeping the WA's and the user's combined centre of mass directly above the users feet at all times to ensure the WA is stable.

Figure 49A:
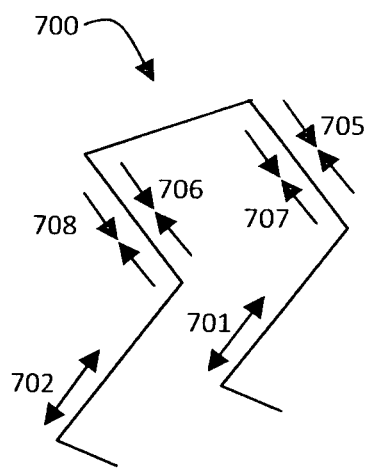
FIGS. 49*a* and 49*b* show the model of the exoskeleton undergoing a standing movement sequence in accordance with a preferred form of the control system of the WA.
Figure 49B:
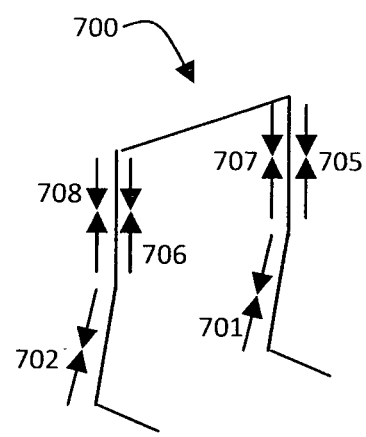

FIGS. 49(a) and 49(b) show the instructions associated with a stand command. These are:
 (iii) Shifting the centre of mass off the seat (FIG. 49(a)), and
 (iv) Raising the centre of mass forward (ending in the standing position of FIG. 49(b)).

Table 5 below shows the relative actuator movements (starting from a sitting position) required for carrying out the sit sequence defined by instruction (i) and (ii) above.

TABLE 4

Relative Actuator Movements Starting from Standing (mm)

| Number on Movement Sequence | | 1/L Ankle | 2/R Ankle | 3/L Side Ankle | 4/R Side Ankle | 5/L Knee | 6/R Knee | 7/L Hip | 8/R Hip | 9/L Side Hip | 10/R Side Hip |
|---|---|---|---|---|---|---|---|---|---|---|---|
| | | | | Starting from the Standing Position | | | | | | | |
| 48(a) | Lowering the Centre of Mass Forward | 6 | 6 | 0 | 0 | 7 | 7 | 6 | 6 | 0 | 0 |
| 48(b) | Shifting the Centre of Mass on to the Seat (ending in the sitting position) | 12 | 12 | 0 | 0 | 86 | 86 | 75 | 75 | 0 | 0 |

TABLE 5

Relative Actuator Movements Starting from Sitting (mm)

| Number on Movement Sequence | | 1/L Ankle | 2/R Ankle | 3/L Side Ankle | 4/R Side Ankle | 5/L Knee | 6/R Knee | 7/L Hip | 8/R Hip | 9/L Side Hip | 10/R Side Hip |
|---|---|---|---|---|---|---|---|---|---|---|---|
| | | | | Starting from the Sitting Position | | | | | | | |
| 49(a) | Shifting the Centre of Mass off the Seat | 0 | 0 | 0 | 0 | −5 | −5 | −4 | −4 | 0 | 0 |
| 49(b) | Raising the Centre of Mass Forward (ending in the standing position) | −19 | −19 | 0 | 0 | −88 | −88 | −77 | −77 | 0 | 0 |

Tables 2-5 above show examples of relative actuator lengths required for carrying out the specific instructions of the abovementioned movement sequences. Data such as values/variables indicative of these lengths will be stored against each associated instruction for each of the movement sequences to pre-program the control system of the WA. Upon calling a particular movement sequence, the values/variables associated with the first instruction of the sequence will be sent to the motor control system which will perform the required instruction by varying the length of actuators 701-710 accordingly. Upon completion of the first instruction, the variables/values associated with actuator lengths for the second instruction are sent to the motor control system which will again perform the required instruction accordingly. This process is repeated for all the instructions in the sequence. On top of the values/variable associated with the instruction, the WA stores time data indicative of the time allocated to each instruction before the next one issues.

It will be apparent that the actuator lengths provided in the tables above are only exemplary and can be varied depending on the particular dimensions and application of the WA. Furthermore, it will be appreciated that the concept of pre-programmed sequences could be applied on a number of other movement sequences such as shuffle and step-up/step-down (for stairs) and such other sequences are not intended to be excluded from the scope of this invention. Instructions and associated actuator movements for discretely mimicking the natural steps of the human body for these other sequences can be determined offline and programmed into the WA to increase the versatility of the exoskeleton.

Terrain and Balance Sub-systems

The preferred form control system comprises two sub-systems, namely the terrain sub-system and the balance sub-system. The terrain sub-system modifies the pre-programmed sequences to stabilise the WA when it is moving, for example walking, on uneven or sloped terrain. The balance sub-system modifies actuator positions in real-time to ensure that the centre of pressure of the WA is within the support polygon during a walk sequence. The architectures of a preferred form of terrain and balance sub-systems will now each be described separately, but it will be appreciated that they operate concurrently in the preferred form control system.

Terrain Sub-system

As described with reference to FIG. 10, the preferred form exoskeleton employs four contact sensors, such as tactile sensors (momentary on switches), at the bottom of each foot member of the WA to examine the terrain under the WA. The tactile sensors trigger when a set point on the device contacts the surface of the ground. In the preferred form, there are four tactile sensors associated with each foot; one at the front left portion, one at the back left portion, one at the front right portion and one at the back right portion of the foot, ie one tactile sensor in each corner region of the sole of the foot. These four sensors provide an indication of the slope of the surface under the foot, relative to the foot's orientation. The corner regions form two pairs of substantially aligned corner regions in a transverse direction and two pairs of substantially aligned corner regions in a longitudinal direction. Data indicative of the change in terrain slope is received when a trigger signal is received from the sensor or sensors of only some of the corner regions upon contact of the underside of the landing foot member with the terrain. For example, if all four sensors trigger upon placement of the foot on the surface, then the foot's orientation is at the same slope as the surface (ie the foot's orientation is aligned with the transverse and longitudinal components of the terrain slope) and the WA does not need to be adjusted for the terrain. If however only the two front sensors are triggered when the leg is lowered onto the surface, then the slope of the surface is greater than the angle of orientation of the foot in the longitudinal direction, and the foot would need to be adjusted for the terrain. It will be appreciated that in alternative embodiments more than one sensor can be used at each portion of the foot if desired by the particular application.

As discussed with reference to FIG. 10, the preferred form foot members 18 may also comprises two middle region contact sensors. These sensors provide information regarding the state of contact of the middle or central front and back regions of each foot member with the ground underneath. The additional contact information provided by the middle region contact sensors provides increased resolution to the terrain subsystem as to the alignment of the foot member with the terrain underneath. Such information enables the terrain subsystem to calculate the extent to which a foot member is through a terrain transition, for example inclined-flat or flat-declined. For example, depending on which middle region contact sensors are triggered, the terrain subsystem can determine whether the foot member is at the start, middle or end of a terrain transition. This information can be used by the terrain subsystem to adjust the movement sequences to more efficiently handle a terrain transition, and may be employed in some forms of the control system.

In an alternative embodiment the contact sensors may be pressure sensors arranged in a similar configuration to that described for the tactile sensors above. The pressure sensors are capable of providing an output indicative of contact between the sole (underside) of the foot and the surface of the ground. In the following description of the terrain sub-system reference will be made to tactile sensors or momentary on switches however it will be appreciated that the alternative pressure sensor form could be employed instead without altering the method of operation of the control subsystem.

Figure 50:
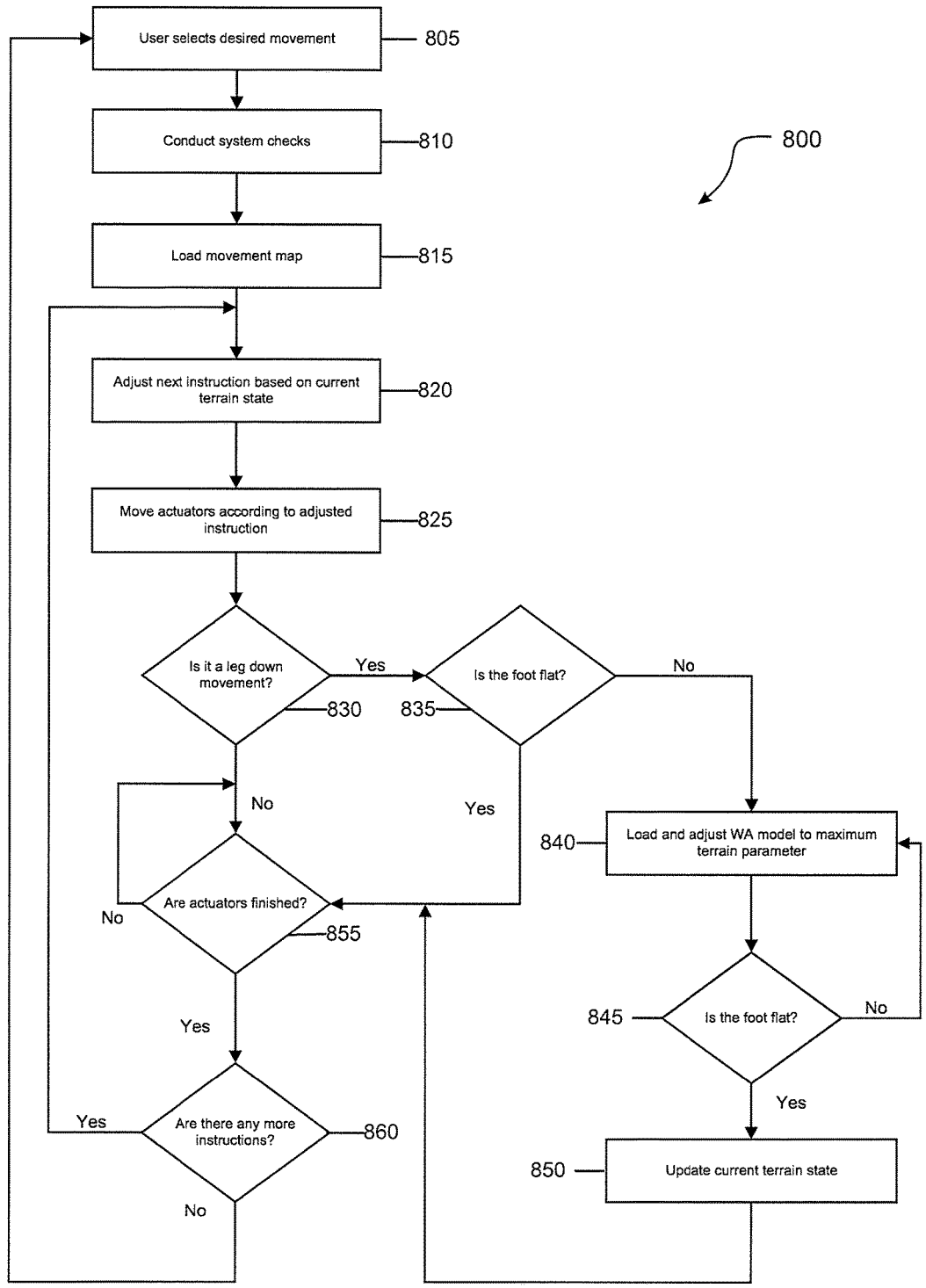
FIG. 50 shows a flow diagram of the sequence of operations performed by a terrain sub-system in accordance with a preferred form of the control system of the WA.

FIG. 50 outlines the program flow 800 associated with the terrain sub-system of the preferred form control system.

During normal operation of the WA, a user has the option of selecting a particular movement sequence via the user interface described above. Once the user selects the desired movement at step 805 a series of system checks may be performed by the WA system (or alternatively a temporary handover to a fault detection sub-system or similar to perform these checks may occur). The system checks of step 810 may include, but are not limited to, any one or more of the following:

Check system fault conditions.

Check if battery level is sufficient to complete the command.

Check the current position of the WA and in particular the actuators.

Check the validity of the current physical condition.

Check the validity of the sensor outputs required for the current desired movement sequence.

Other system checks may be performed depending on the complexity of the system to which they are employed or depending on the particular movement sequence selected by the user.

If there are no faults and the system is satisfied that the particular movement sequence selected can be conducted appropriately without major risk of failure, the pre-programmed data containing the corresponding movement map or sequence of instructions (e.g. sit, stand, walk and shuffle as described above) is loaded 815 from memory into the motor control sub-system. Before the series of instructions are sent to the motor controllers (or directly to the actuators if a motor control system is not employed), they are adjusted based on the current terrain state (step 820). The pre-programmed movement sequence data assumes flat terrain. The terrain sub-system updates and stores the current terrain state to update the movement sequence data and adjust it to comply with the current terrain.

The current terrain state is stored as offset data relative to a flat terrain position in degrees. The orientation of the current terrain relative to the flat terrain may be represented by an offset angle in the longitudinal direction (along the direction of movement of the exoskeleton) and an offset angle in the transversal direction (at approximately right angles to the direction of movement of the exoskeleton). Before the initial or next instruction gets issued to the motor control system, the currently stored offset terrain data is converted from degrees to corresponding actuator lengths. The conversion is done using an actuator length to degree relationship stored within the terrain subsystem. In the preferred form of the exoskeleton, actuators 703, 704, 709 and 710 (from FIGS. 45-49) are modified with the transverse terrain state (transversal offset angle) and actuators 701 and 702 are modified with the longitudinal terrain state (longitudinal offset angle). Actuators 705, 706, 707 and 708 will remain unchanged. If the current terrain is flat the offset data will be set to zero or a flag will be set to indicate no update required. Once the instruction values have been adjusted (or the no update required flag is returned if that is the case) they are sent to the motor controllers or directly to the actuators which perform the updated instruction 825. Instruction data that is sent to the actuators generally contains the desired location (or change in actuator length) for the ten actuators and the desired time period for performing the instruction.

Pre-programmed sequence data contains a series of instructions for an entire movement sequence. Also included with each instruction in addition to time and desired actuator locations are fixed foot and leg down flags (or landing foot instruction flags). The fixed foot flag indicates whether the left or right foot or both are fixed on the ground and it is used for the WA model calculations as will be described in more detail later. The leg down flag (or landing foot instruction) signals if the instruction is one where the leg is coming down. When the leg down flag is true (step 830) the terrain sub-system is activated.

When one or more of the tactile sensors of the non-fixed foot (determined by the fixed foot flag) trigger, the terrain sub-system halts all the actuators on the WA. If the non-fixed foot is flat, i.e. all four tactile sensors at every corner are simultaneously triggered such that the foot is aligne'd with the terrain underneath in both the longitudinal and transverse directions, then there is no need to update the terrain status and the WA will exit the terrain sub-system and continue to move the actuators and complete the instruction. If however the foot is not flat 835 (i.e. all four tactile sensors do not simultaneously trigger indicating that the foot is not fully aligned with the terrain underneath), the actuator movements are halted and the current positions of all the actuators are stored and passed to a WA mathematical model.

The terrain slope consists of a longitudinal component and a transverse component, and data received from the tactile sensors indicative of a change in terrain slope will indicate either a change in the longitudinal component of the terrain slope or a change in the transverse component of the terrain slope or both. Receiving a trigger signal from at least one contact sensor associated with only one of the two pairs of transversely aligned corner regions indicates a change in the longitudinal component of the terrain slope. Similarly receiving a trigger signal is from at least one contact sensor associated with only one of the two pairs of longitudinally aligned corner regions indicates a change in the transverse component of the terrain slope. The foot is pivoted towards the maximum allowable angle about an axis traversing through the pair of aligned corner regions from which a trigger signal is received to align the foot with the component of the slope that has changed. The maximum allowable slope angle is either a maximum allowable angle between the slope and a longitudinally extending and substantially horizontal line, or a maximum allowable transverse angle between the slope and a transversely extending and substantially horizontal line depending on which component of the slope has changed. Pivotal movement of the foot then terminates upon receiving a trigger signal from at least one sensor associated with an opposing pair of aligned corner regions to the pair through which the pivot axis traverses. This indicates alignment of the foot member with the slope of the terrain.

The WA mathematical model (840) will be used to control the actuators to adjust the non-fixed foot towards the maximum allowable terrain slope (either in the transverse or longitudinal direction or both) until all four tactile sensors trigger (i.e. until the foot is flat 845). The new actuator lengths (when the foot is flat against the terrain) are then converted to angles, with the angle of the foot signifying the angle of the current slope. The current terrain state can therefore be updated 850 with the new slope values.

In a preferred embodiment, in addition to the slope values calculated from the foot angle, accelerometer tilt readings may also be read from the foot in the longitudinal and transversal directions, and averaged with the longitudinal and transverse slope calculations to more accurately update the terrain status.

Once the terrain state is updated, the WA waits for the actuators to finish performing the current instruction 855 and then conducts the next instruction 860 (if there is one). For the next instruction, the new updated terrain state data is used to adjust 820 the instruction's pre-programmed actuator length data.

A preferred form of the WA mathematical model will now be described in more detail with reference to the flow chart of FIG. 51 and the exemplary scenario of FIGS. 52-63.

WA Mathematical Model

Figure 51:
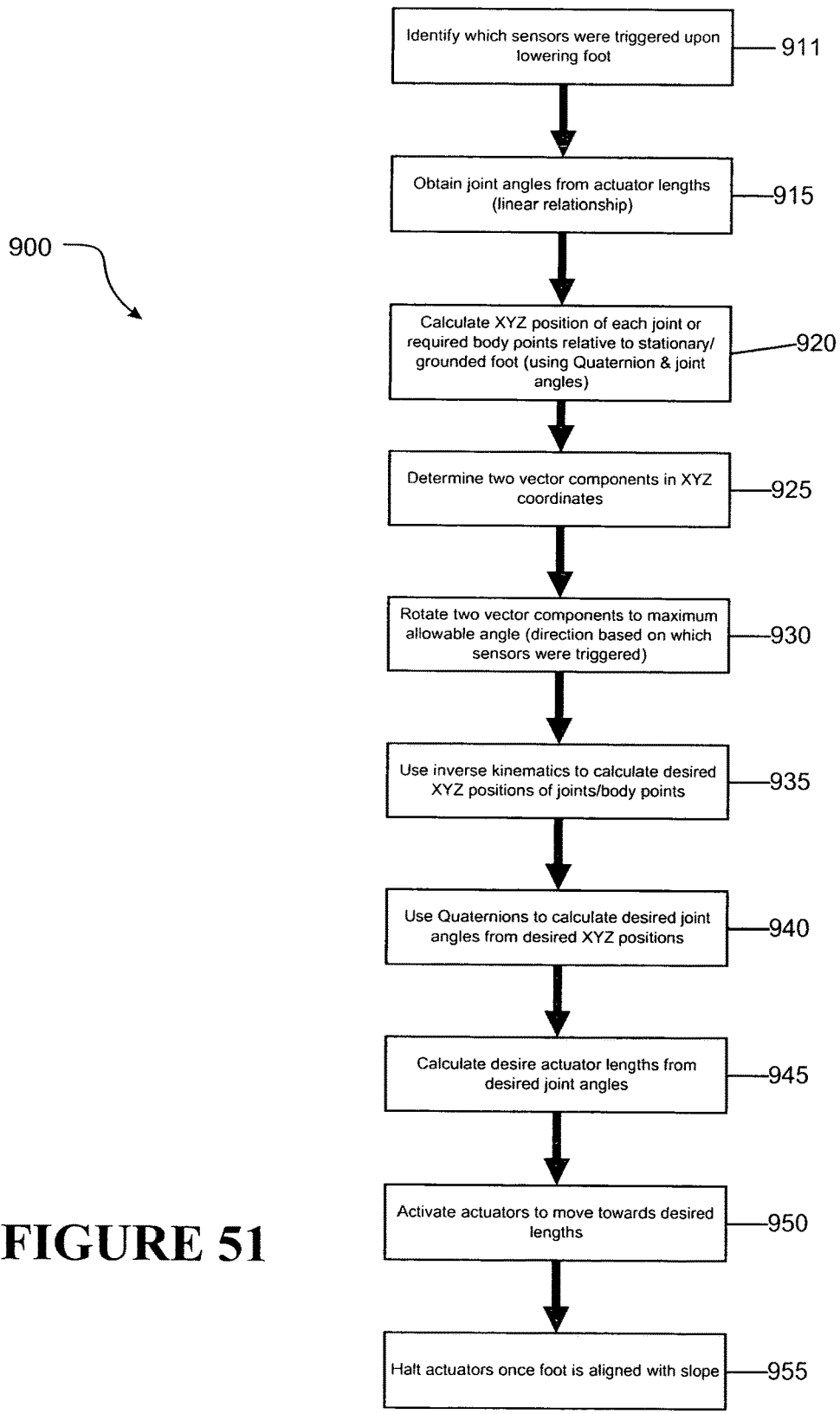
FIG. 51 shows a flow diagram of the sequence of operations performed by a mathematical model employed by the terrain sub-system of FIG. 50.

FIG. 51 shows a flow chart 900 of the preferred method for adjusting the foot to the terrain. After the actuators have halted (as described above in step 835) the terrain subsystem identifies which of the four sensors were triggered (step 911). This provides an indication of the direction or directions required to rotate the foot such that it is aligned with the slope of the terrain. For example, if only the two front sensors were triggered then the foot needs to rotate about the front of the foot in a clockwise direction. Similarly if the two left side sensors were triggered then the foot needs to be rotated about its left side in a clockwise direction. The extent to which the foot rotates is determined by simply ceasing rotation upon receiving a signal from all four sensors, i.e. the foot is rotated until all four sensors are triggered which indicates a flat foot that is now aligned with the slope of the terrain. It will be appreciated that the foot may need to be rotated in the longitudinal direction, transverse direction, or both, depending on the change in terrain slope.

To rotate the foot appropriately, the WA mathematical model needs to first obtain the angles of ten joints in the exoskeleton (step 915). FIGS. 52*a* and 52*b* show a model of the exoskeleton 500 of FIGS. 1-40 and the ten joint angles 901-910 that need to be calculated. FIG. 52*a* shows the exoskeleton from the side and the angles the joints make in the longitudinal direction. FIG. 52*b* shows the exoskeleton from behind and the angles the joints make in the transverse direction. Table 6 below shows the relationship between joint angles 901-910 of FIGS. 52*a* and 52*b* and the corresponding joints of exoskeleton 500 (of FIGS. 1-40) and the axis to which they rotate about to make that angle.

TABLE 6

| Joint Angle | Corresponding Joint and Axis of rotation |
| --- | --- |
| 901 | 17 rotating about axis 17A (left foot—see FIG. 5) |
| 902 | 17 rotating about axis 17A (right foot—see FIG. 5) |
| 903 | 17 rotating about axis 17B (left foot—see FIG. 6) |
| 904 | 17 rotating about axis 17B (right foot—see FIG. 6) |
| 905 | 12 rotating about axis 12A (left leg—see FIG. 2) |
| 906 | 12 rotating about axis 12A (right leg—see FIG. 2) |
| 907 | 14 rotating about axis 14A (left hip—see FIG. 7) |
| 908 | 14 rotating about axis 14A (right hip—see FIG. 7) |
| 909 | 14 rotating about axis 14B (left hip—see FIG. 8) |
| 910 | 14 rotating about axis 14B (right hip—see FIG. 8) |

Joint angles 901-910 can be calculated from the lengths of actuators 701-710 using a simple linear relationship. Table 7 below gives an example of such a relationship however it will be appreciated that the values used are dependent on the exoskeleton system components (i.e. the type and dimensions of the joints and actuators).

TABLE 7

| Joint | Rate of change of Angle (Actuator Extension (mm) per degree of joint angle) |
| --- | --- |
| 901 and 902 | 1.1664 (Actuators 701 and 702) |
| 903 and 904 | 0.902 (Actuators 703 and 704) |

TABLE 7-continued

| Joint | Rate of change of Angle (Actuator Extension (mm) per degree of joint angle) |
| --- | --- |
| 905 and 906 | 1.146 (Actuators 705 and 706) |
| 907 and 908 | 1.0581 (Actuators 707 and 708) |
| 909 and 910 | 0.8623 (Actuators 709 and 710) |

After the WA mathematical model calculates the joint angles from the actuator lengths, global X, Y and Z coordinates are calculated in an iterative manner for certain body points of the exoskeleton (step 930). FIGS. 53*a* and 53*b* show the same model as in FIGS. 52*a* and 52*b* with body points 971-981 labelled. In this particular example the XYZ coordinates of body points 977-981 are desired to represent the current position of the non-fixed foot when the actuators have halted. The XYZ positions of body points 972-981 are calculated relative to the fixed foot body point 971. The method of calculation is iterative and it consecutively calculates the XYZ coordinates of body points 972-981 relative to the foot which is fixed (on the ground), body point 971.

The method of calculating the 'global' X, Y and Z co-ordinates is achieved using Quaternion's. The calculation begins with XYZ(1), which is located at the ankle joint of the leg and has the 'Fixed Foot Flag' turned on; this is first body point 971 in FIG. 53*a*. XYZ(1) is initialized to a reference zeroed coordinate of the global X,Y,Z coordinate system, namely X=0, Y=0 and Z=0. In Vector form, this is:

$$\begin{bmatrix} X(1) \\ Y(1) \\ Z(1) \end{bmatrix} = \begin{bmatrix} 0 \\ 0 \\ 0 \end{bmatrix}$$

Body point 972 underwent two rotations to arrive at its current position, a rotation of angle 901 (produced by actuator 701) and a rotation of angle 903 (produced by actuator 703). Angles 901 and 903 can be seen in FIGS. 52*a* and 52*b*.

The location of the nth body point (where body point 971 is the first body point, body point 972 is the second etc. . . . ) after being rotated at an angle $\theta_i$ is given by:

$$\begin{bmatrix} X(n) \\ Y(n) \\ Z(n) \end{bmatrix} = \begin{bmatrix} X(n-1) \\ Y(n-1) \\ Z(n-1) \end{bmatrix} + \begin{bmatrix} w^2 + X^2 - Y^2 - Z^2 & 2*X*Y - 2*W*Z & 2*X*Z - 2*W*Y \\ 2*X*Y + 2*W*Z & w^2 - X^2 + Y^2 - Z^2 & 2*Y*Z - 2*W*X \\ 2*X*Z - 2*W*Y & 2*Y*Z - 2*W*X & w^2 - X^2 - Y^2 + Z^2 \end{bmatrix} * \begin{bmatrix} X(n) - X(n-1) \\ Y(n) - Y(n-1) \\ Z(n) - Z(n-1) \end{bmatrix}$$ (equation 1.1)

Where: n=represents the nth body point
i=joint angle number
W=cos($\theta_i$/2)

$X = i * \sin(\theta_i/2)$ $Y = j * \sin(\theta_i/2)$ $Z = k * \sin(\theta_i/2)$ i=unit vector in the X direction j=unit vector in the Y direction k=unit vector in the Z direction Equation 1.1 is applied twice for the second body point 972, once using i=901 and once using i=903, for joint angles 901 and 903 respectively. n is incremented after calculating the new XYZ position of body point 972. This process terminates once the last body point (body point 980) is reached. Body point 981 can then be calculated relative to body point 979 using angles 904 and 902.

Once the location of all body points (971-981) has been calculated in the X, Y and Z co-ordinate frame, the XYZ co-ordinates of the foot which made contact with the terrain slope (body points 976, 977, 978, 979,980 and 981 in FIG. 53), are manipulated to achieve the maximum allowable terrain slope. The maximum allowable terrain upon which the exoskeleton can move is preset according to the exoskeleton parameters and capabilities. In the preferred form, the maximum allowable terrain is composed of two parameters, one that states the maximum angle allowable in the longitudinal direction, the other states the maximum angle allowable in the transversal direction. The following will provide a description of how the maximum allowable terrain can be achieved by way of example only. It will be appreciated however that this technique can be appropriately applied by the control system to the situation at hand, and the values of the variables discussed are provided by way of example.

Achieving Maximum Longitudinal Angle:

A change in longitudinal slope is detected when either the back switch(es) or front switch(es) are activated, but not both. Theoretically, the sequence of events required to achieve the maximum longitudinal angle for both scenarios is the same.

Figure 54:
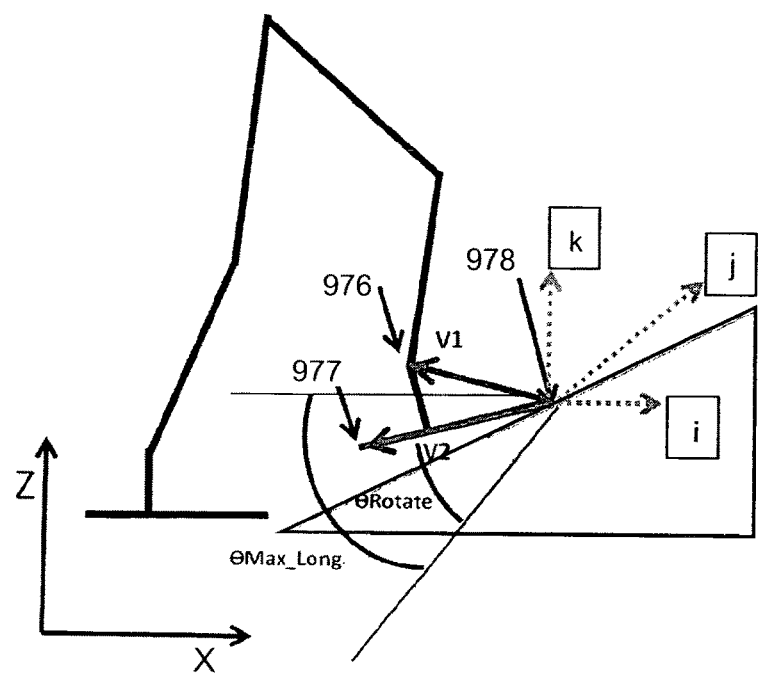
FIGS. 54-58 show an example of the process associated with adjusting a foot of the exoskeleton to a change in terrain slope in the longitudinal direction with reference to the exoskeleton model.

FIG. 54 shows an example where (one or both of) the front switches are activated but not the back due to a difference in angle between the landing foot and the longitudinal slope of the terrain. As mentioned above, when the tactile switch(es) are activated the actuators halt. The XYZ coordinates of body points 976, 977, and 978 are used by the terrain subsystem to define two vectors, V1 and V2 as shown in FIG. 54 (step 935 of FIG. 51). V1 and V2 have their origins at the point of the foot which contacts the terrain surface. In the case of FIG. 54, this is body point 978. The vectors extend in the longitudinal direction with V1 terminating at the ankle portion (body point 976 in the example) and V2 terminating at the other end of the foot (body point 977 in the example).

Using the vector notation for the body point coordinates above the mathematical model therefore needs to define:

$$V1 = \begin{bmatrix} X(6) - X(8) \\ Y(6) - Y(8) \\ Z(6) - Z(8) \end{bmatrix}$$

$$V2 = \begin{bmatrix} X(7) - X(8) \\ Y(7) - Y(8) \\ Z(7) - Z(8) \end{bmatrix}$$

Once the two vectors have been determined, the mathematical model will attempt to rotate these vectors to the maximum allowable angle. A set of unit vectors, i, j and k are used by the model to define an axis of rotation for vectors V1 and V2 (vector j in FIG. 54 goes into the page). The vectors are set depending on which corner(s) of the foot contacted the terrain. When the unit vectors are set to i=0, j=−1 and k=0 for example, body point 978 acts as a pivot point for rotation of V1 and V2. The direction of rotation is determined also based on which portion of the foot contacted the terrain, i.e. if the front sensors trigger then rotation is clockwise in the longitudinal direction, and if the back sensors trigger then rotation is anti-clockwise.

The angle, $\theta_{rotate}$, required to rotate the vectors V1 and V2 such that they are at the maximum allowable angle in the longitudinal direction is determined by differencing the pre-stored $\theta_{max\_long}$ (which defines the maximum allowable slope angle in the longitudinal direction relative to the horizontal/flat terrain as shown in FIG. 54) with the angle of V2, $\theta_{V2}$ (which can be determined using known mathematical techniques). Therefore $\theta_{rotate} = \theta_{max\_long} - \theta_{V2}$.

Figure 55:
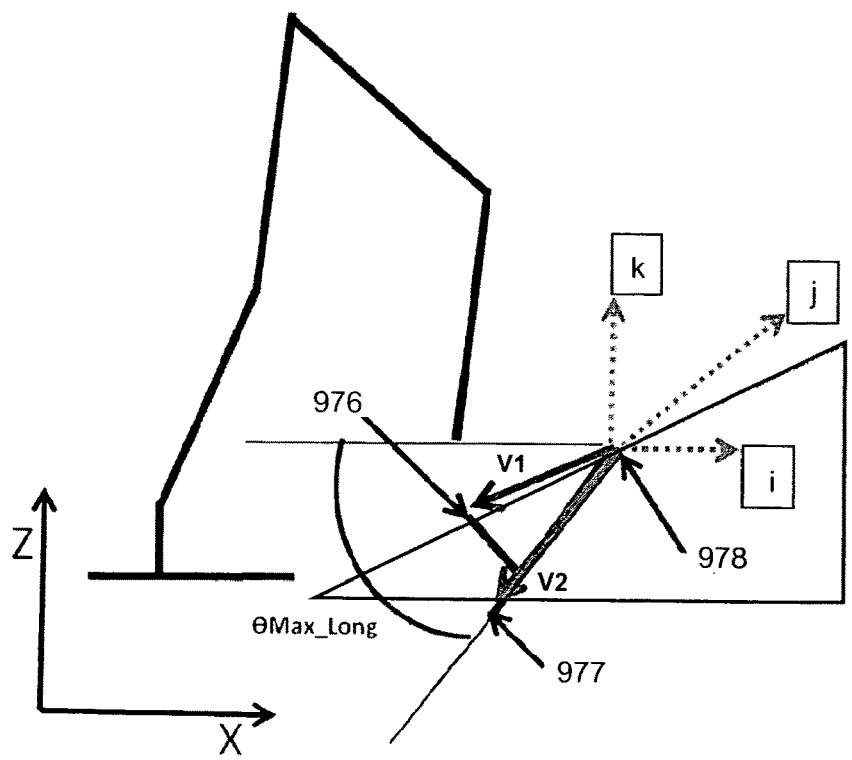

FIG. 55 shows the theoretical location of vectors V1 and V2 after such a rotation (result of step 940 of FIG. 51). As can be seen, V1 and V2, and more importantly body points 976-978 of the exoskeleton are now represented as being oriented at the maximum allowable longitudinal slope. Rotated V1 and V2 now define the desired position of body points 976-978. To achieve this desired position, the knee joint (or body point 975 in the example) needs to move from the position shown in FIG. 56 to the new position labelled 975(new) shown in FIG. 57. To calculate this new desired position 975(new) of body point 975, inverse kinematics is used by the mathematical model (step 945 of FIG. 51).

Figure 56:
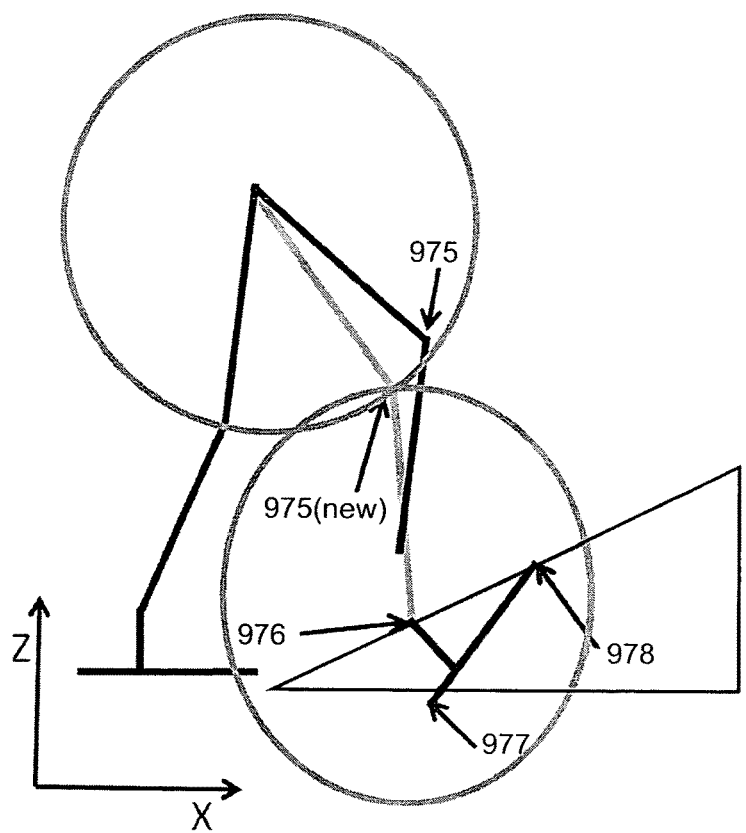
Figure 57:
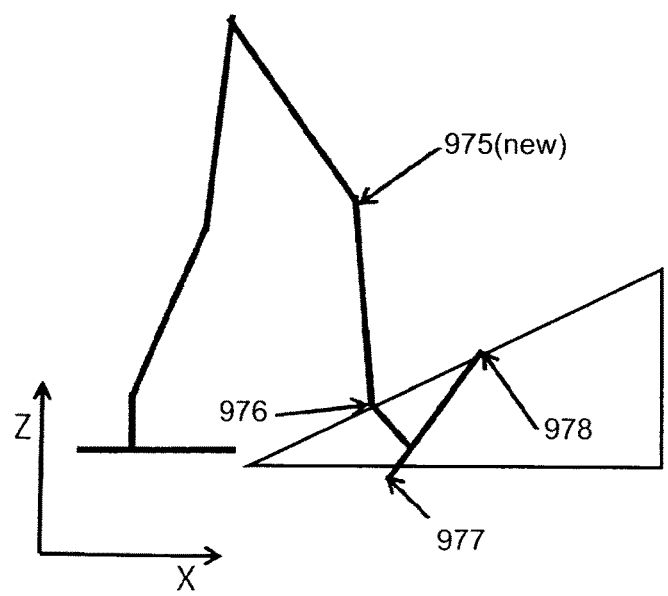

In the preferred form, as can be seen in FIG. 56, the method of intersecting circles is used to link up the lower part of the lower limb to body point 976 and solve for body point 975(new). The XYZ coordinates of 975(new) is taken as the intersection point between the two circles (having their centres at body points 974 and 975 and their radius defined by length 974-975 and 975-976 respectively) that has a higher value in the X coordinate. This ensures the knee joint stays within the human biomechanical limits. This is one known inverse kinematics method that can be used to solve for 975(new) however it will be appreciated that other methods known to a skilled person could alternatively be applied by the model.

Figure 58:
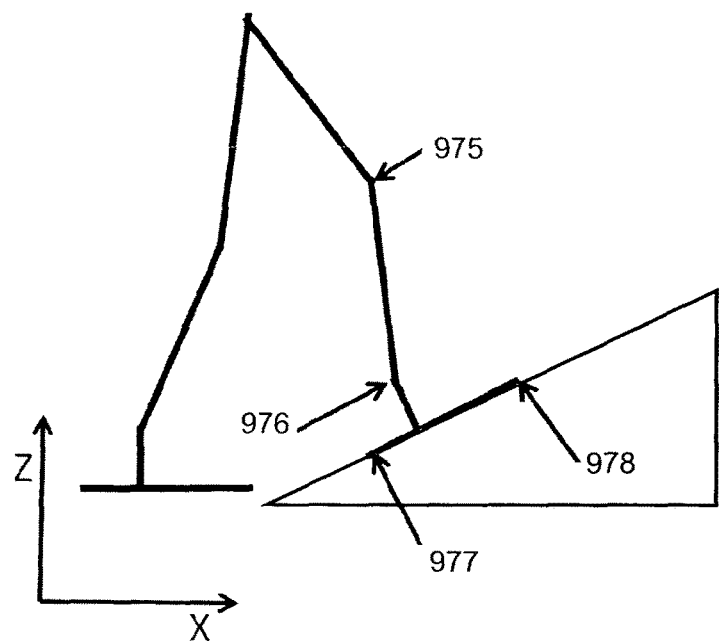

The mathematical model at this stage has determined the new theoretical or desired positions (in XYZ coordinates) of body points 975-978 that will achieve an orientation of the foot that coincides with the maximum allowable slope in the longitudinal direction. These theoretical positions in XYZ coordinates are converted into joint angles (using equation 1.1 previously described—step 950 in FIG. 51) and the joint angles subsequently translated into actuator lengths, step 955 of FIG. 51 (using the linear relationship also previously described). The actuator lengths (that will achieve the maximum allowable foot orientation) are then sent to the motor controllers (or directly to the actuators). The actuators will be activated to adjust towards these desired lengths (step 960 of FIG. 51) until the back sensors contact the terrain surface to bring the foot into alignment with the terrain with respect to the longitudinal direction. At this stage the actuators stop their motion as the angle of the foot in the longitudinal direction matches the angle of the slope as shown in FIG. 58 (step 965 of FIG. 51). The angle of the foot in the longitudinal direction is calculated from the current actuator lengths to update the longitudinal component of the current terrain state.

Achieving Maximum Transverse Angle

The method by which the exoskeleton adjusts to a change in slope in the transversal direction is similar to that described above for the longitudinal. An example will be given however for clarity.

A change in transversal slope is detected when either the left switch(es) or right switch(es) are activated, but not both. Theoretically, the sequence of events required to achieve the maximum transverse angle for both scenarios is the same.

Figure 59:
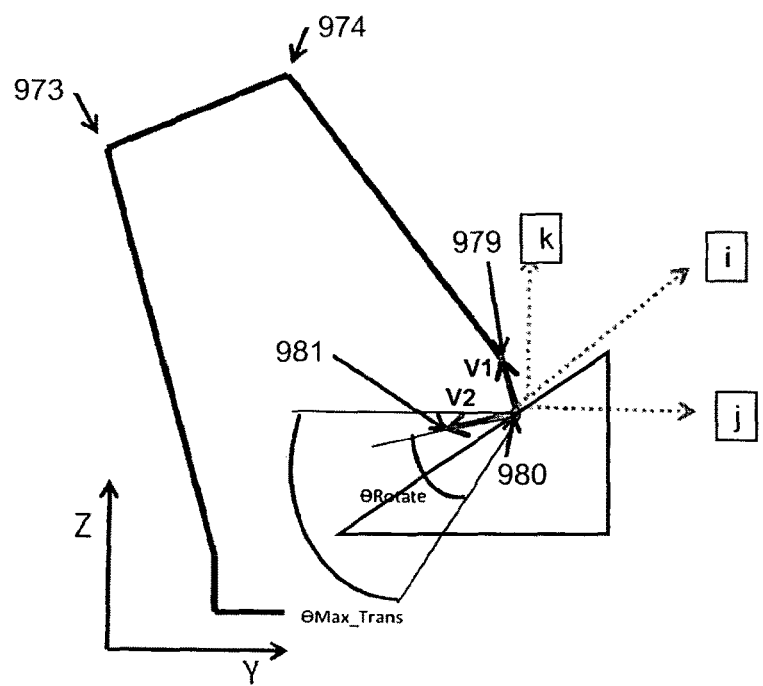
FIGS. 59-63 show an example of the process associated with adjusting a foot of the exoskeleton to a change in terrain slope in the transverse direction with reference to the exoskeleton model.

FIG. 59 shows an example where (one or both of) the right switches are activated but not the left due to a difference in angle between the landing foot and the longitudinal slope of the terrain. As mentioned above, when the tactile switch(es) are activated the actuators halt. The XYZ coordinates of body points 979, 980, and 981 are used by the terrain subsystem to define two vectors, V1 and V2 as shown in FIG. 59 (step 935 of FIG. 51). V1 and V2 have their origins at the point of the foot which contacts the terrain surface. In the case of FIG. 59, this is body point 980. The vectors extend in the transversal direction with V1 terminating at the ankle portion (body point 979 in the example) and V2 terminating at the other end of the foot (body point 981 in the example).

Using the vector notation for the body point coordinates above the mathematical model therefore needs to define:

$$V1 = \begin{bmatrix} X(9) - X(10) \\ Y(9) - Y(10) \\ Z(9) - Z(10) \end{bmatrix}$$

$$V2 = \begin{bmatrix} X(11) - X(10) \\ Y(11) - Y(10) \\ Z(11) - Z(10) \end{bmatrix}$$

Once the two vectors have been determined, the mathematical model will attempt to rotate these vectors to the maximum allowable angle. A set of unit vectors, i, j and k are used by the model to define an axis of rotation for vectors V1 and V2 (vector i in FIG. 59 goes into the page). The vectors are set depending on which corner(s) of the foot contacted the terrain. When the unit vectors are set to i=1, j=0 and k=0 for example, body point 978 acts as a pivot point for rotation of V1 and V2. The direction of rotation is determined also based on which portion of the foot contacted the terrain, i.e. if the right sensors trigger then rotation is anticlockwise in the transversal direction, and if the left sensors trigger then rotation is clockwise.

The angle, $\theta_{rotate}$, required to rotate the vectors V1 and V2 such that they are at the maximum allowable angle in the transversal direction is determined by differencing the pre-stored $\theta_{max\_trans}$ (which defines the maximum allowable slope angle in the transversal direction relative to the horizontal/flat terrain as shown in FIG. 59) with the angle of V2, $\theta_{V2}$ (which can be determined using known mathematical techniques). Therefore $\theta_{rotate} = \theta_{max\_trans} - \theta_{V2}$.

Figure 60:
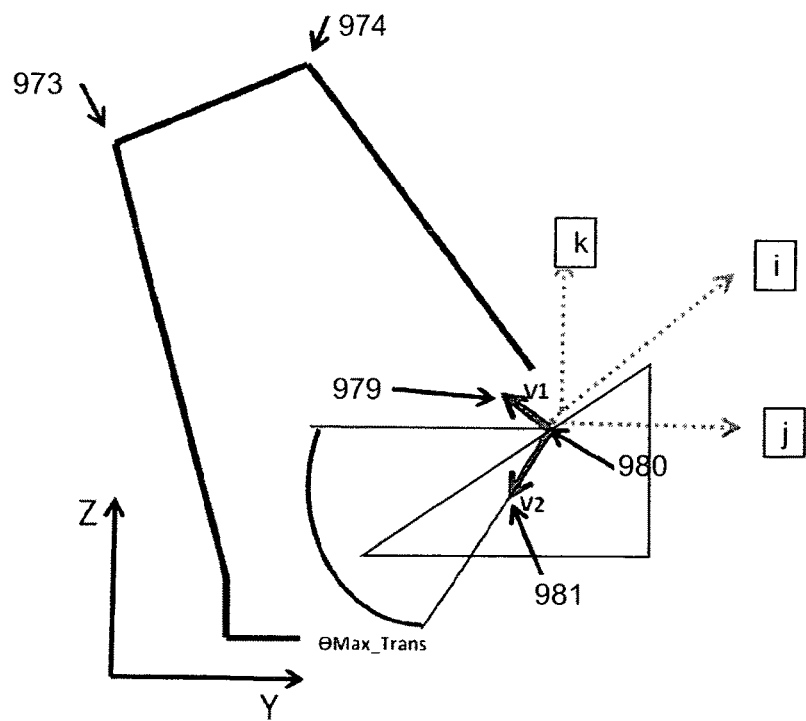

FIG. 60 shows the theoretical location of vectors V1 and V2 after such a rotation (result of step 940 of FIG. 51). As can be seen, V1 and V2, and more importantly body points 979-981 of the exoskeleton are now represented as being oriented at the maximum allowable transverse slope. Rotated V1 and V2 now define the desired position of body points 979-981. To achieve this desired position, the hip joint (or body point 974 in the example) needs to move from the position shown in FIG. 61 to the new position labelled 974(new) shown in FIG. 62. To calculate this new desired position 974(new) of body point 974, inverse kinematics is used by the mathematical model (step 945 of FIG. 51).

Figure 61:
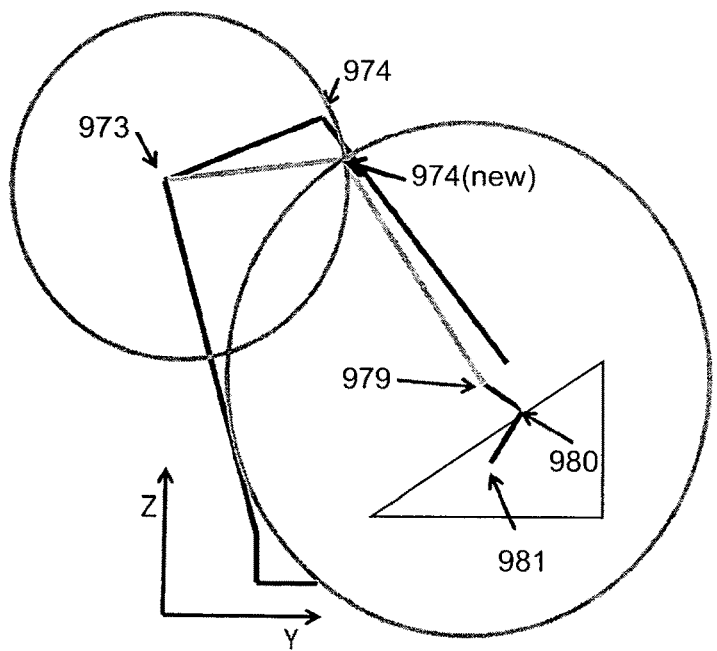
Figure 62:
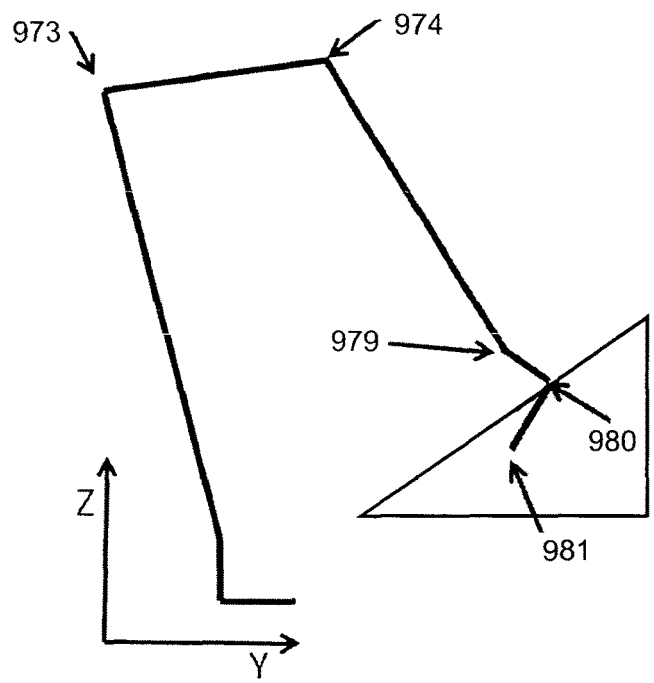

As can be seen in FIG. 61, the method of intersecting circles is used to link up the lower part of the lower limb to body point 979 and solve for body point 974(new). The XYZ coordinates of 974(new) is taken as the intersection point between the two circles (having their centres at body points 973 and 974 and their radius defined by length 973-974 and 974-979 respectively) that has a higher value in the Y coordinate. This ensures the hip joint stays within the human biomechanical limits. This is one known inverse kinematics method that can be used to solve for 974(new) however it will be appreciated that other methods known to a skilled person could alternatively be employed by the model.

Figure 63:
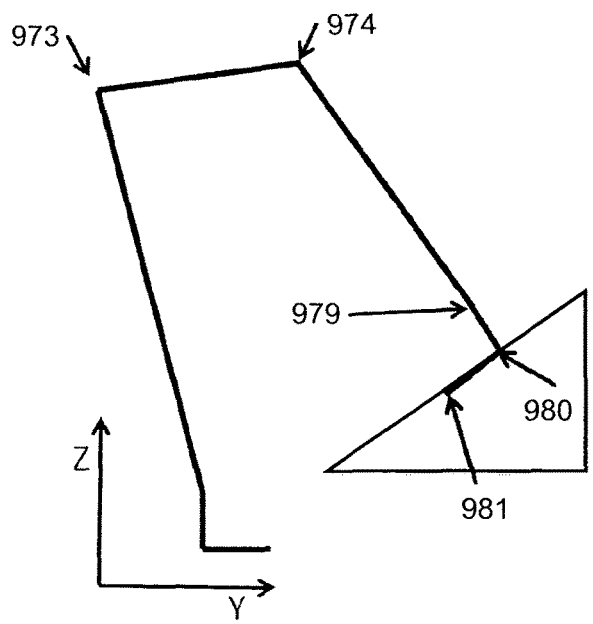

The mathematical model at this stage has determined the new theoretical positions (in XYZ coordinates) of body points 974 and 979-981 that will achieve an orientation of the foot that coincides with the maximum allowable slope in the transversal direction. These theoretical positions in XYZ coordinates are converted into joint angles (using equation 1.1 previously described—step 950 in FIG. 51) and the joint angles subsequently translated into actuator lengths, step 955 of FIG. 51 (using the linear relationship also previously described). The actuator lengths (that will achieve the maximum allowable foot orientation) are then sent to the motor controllers (or directly to the actuators). The actuators will be activated to adjust towards these desired lengths (step 960 of FIG. 51) until the left sensors contact the terrain surface. At this stage the actuators stop their motion as the angle of the foot in alignment in the transversal direction with the angle of the slope as shown in FIG. 63 (step 965 of FIG. 51). The angle of the foot in the transversal direction is calculated from the current actuator lengths to update the transversal component of the current terrain state.

Terrain State Update

Figure 64:
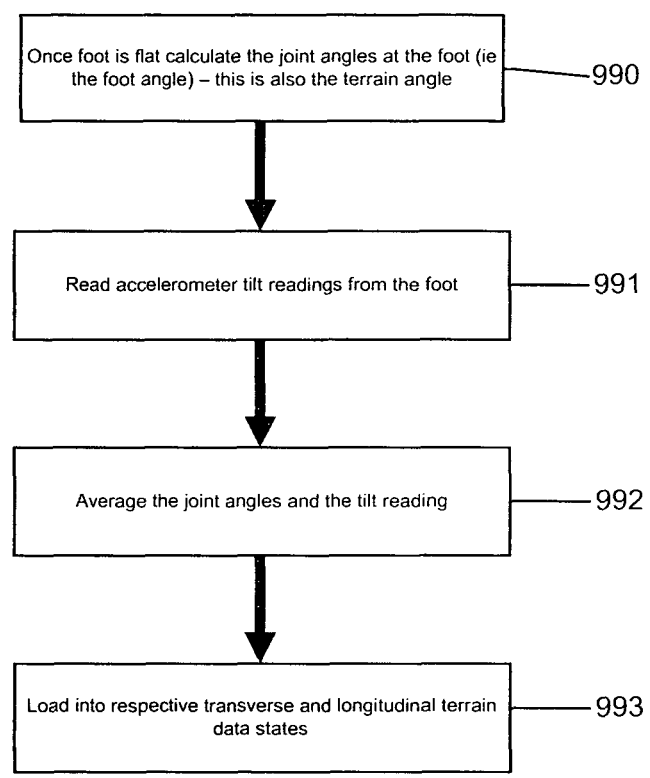
FIG. 64 shows a flow diagram of the process by which the terrain state is updated in the terrain sub-system in accordance with a preferred form of the control system of the WA.

FIG. 64 shows a basic flowchart overview of the terrain state update sequence which occurs after a foot has been adjusted to conform to a new terrain. When the foot of the WA has made full contact with the slope (all tactile switches trigger) as depicted in either FIG. 58 or 63, the WA is loaded with the new actuator lengths. These lengths are converted to angles using the linear relationship of table 7. The angle of the foot in the longitudinal and transverse directions (which is also the angle of the terrain in the longitudinal and transverse direction respectively), is then be calculated from the joint angles (step 990).

Accelerometer tilt readings are also read from the foot in the longitudinal and transverse directions (step 991). The average of both the WA calculated foot angle and the accelerometer results are averaged (step 992) and loaded into the respective transverse and longitudinal terrain data states (step 993) for use with the next instruction.

Balance Sub-system

The balance sub-system modifies actuator positions in real-time to ensure that the centre of pressure (CoP) is within the support polygon during a movement sequence. For a static sequence it is generally sufficient to have the CoP of each foot within the support polygon to maintain stability and balance. For a dynamic system undergoing a movement sequence, it is also necessary to have specific CoP locations within the support polygon for each instruction in the sequence. This prevents the movement sequence from deforming (i.e. it is not sufficient to just have static balance in a dynamic system). If the exoskeleton maintains the desired CoP in each foot during each instruction then the system can appropriately perform the required movement sequence without deforming or losing balance.

Figure 65:
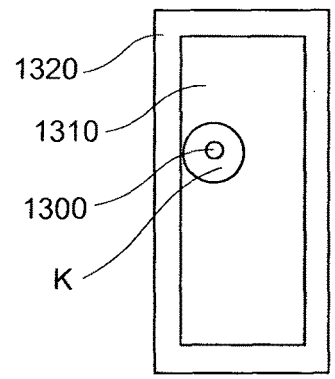
FIG. 65 shows a model of a foot of the exoskeleton and the location of various regions of interest for a balance sub-system in accordance with a preferred form of the control system of the WA.

To achieve the above requirement, offline calculations of CoP location provide a set of target xy positions on each foot for each pre-programmed instruction. The CoP 1300 for each instruction still needs to lie within the support polygon 1310 and within a dead band 1320 formed around each foot as shown in FIG. 65 for the system to be balanced. The dead band is found by balancing the exoskeleton at different angles to determine the point at which it is unbalanced (trial and error).

In general, the balance subsystem will periodically balance the exoskeleton during movement of the one or more actuators according to a current instruction by firstly determining an actual centre of pressure location at the sole of the grounded feet members of the exoskeleton based on input pressure data from pressure sensors indicative of pressure at one or more regions of the foot. Then obtaining the desired centre of pressure location associated with the current instruction to and moving the actuators associated with the orientation of each grounded foot member to a position which shifts the actual centre of pressure under the foot towards the desired centre of pressure for the current instruction.

A proportional integral derivative (PID) controller is used for each of the feet actuators 701, 702, 703 and 704 (of model 700 in FIGS. 45-49) to correct any change in CoP during the instruction (with a tolerance of k as shown in FIG. 65). The error between pre-programmed CoP and the actual CoP during a time instance of a particular instruction is fed into a PID having the form:

$$u_n(t) = K_p e_n(t) + K_i \int_0^t e_n(t) dT + K_d \frac{de_n}{dt}(t)$$

Where:
n=Actuator number 701-704
t=time
$e_n = DCoP_n - ACoP_n$
$DCoP_n$=desired center of pressure
$ACoP_n$=actual center of pressure
$K_p$=Proportional gain constant (trial and error)
$K_i$=Integral gain constant (trial and error)
$K_d$=Derivative gain constant (trial and error)
The output of $u_n$ is in the form $$\frac{\Delta \text{actuator length}}{CoP_{error}}$$

and is the input to the balance control mechanism.

Figure 66:
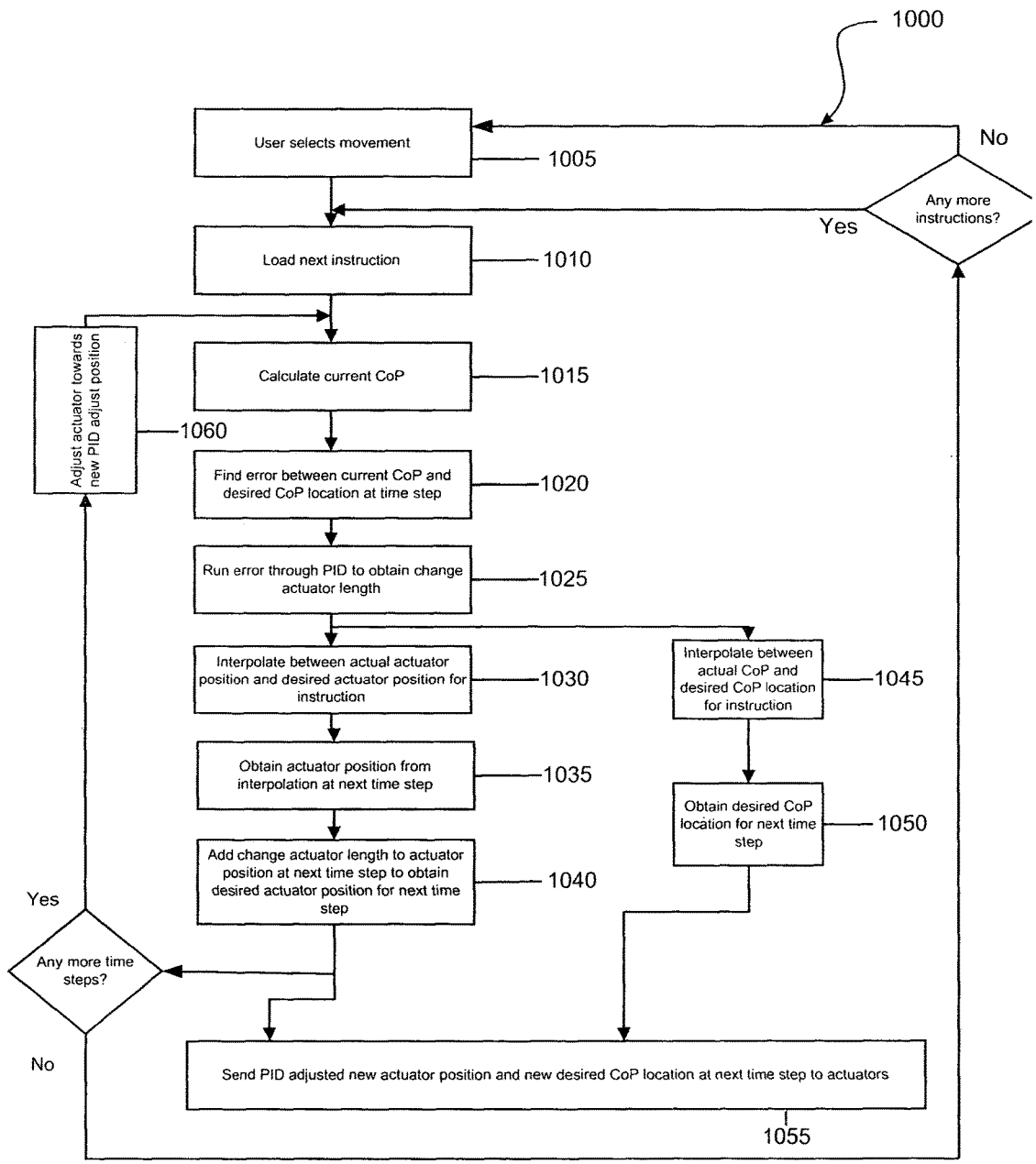
FIG. 66 shows a flow diagram of the sequence of operations performed by the balance sub-system in accordance with a preferred form of the control system of the WA.

FIG. 66 shows the program flow 1000 associated with the balance control sub-system. At step 1005 the user of the exoskeleton selects the particular movement sequence desired. The first instruction is then loaded and the actuators begin to move to perform the instruction (step 1010). The time required to perform a particular instruction is divided into a series of time steps. The time step is a value attained through trial and error and specifies how often over time the balance sub-system is called. It will be appreciated that the balance subsystem may run periodically during a movement sequence at any preset frequency.

After initiating the sequence, the CoP of each grounded foot is calculated (step 1015) at every time step whilst the actuators continue to move. After each time step, the error between the current calculated CoP and a desired CoP location for that particular time step (explained in more detail further) is calculated (step 1020) and fed into the PID controller to obtain the change in actuator length required to correct that error (step 1025).

Figure 67B:
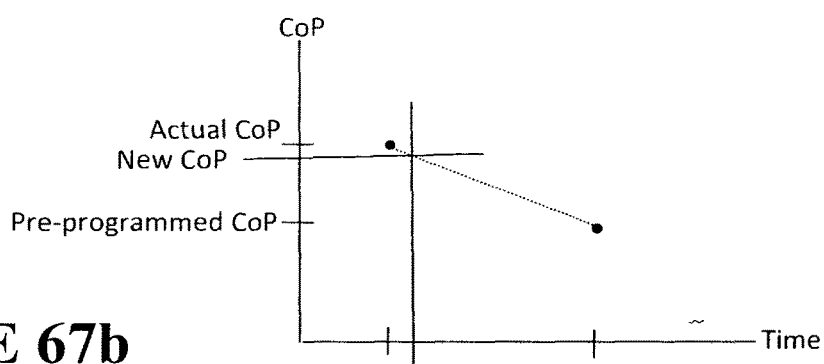
FIGS. 67*a* and 67*b* show graphs of linear interpolations associated with actuator positions and centre of pressure locations respectively for the balance subsystem.
Figure 67A:
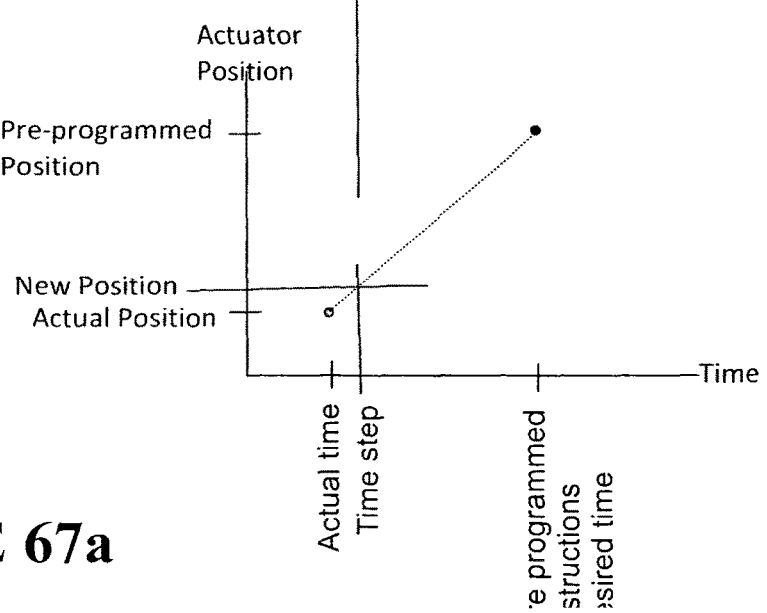

The balance subsystem then interpolates a linear representation between the actual actuator position at the current time step and the desired actuator position at the end of the instruction (step 1030) as shown in FIG. 67*a*. This interpolation allows the actuator position at the next time step to be predicted (step 1035). The output of the PID (change in actuator length) is added to this actuator position prediction to give a desired actuator position for the next time step (1040). In this way the actuator continues to move towards the final desired actuator position for the instruction and also corrects for the CoP error calculated at the current time step.

The mechanism also interpolates a linear representation between the actual CoP and the desired CoP location at the end of the instruction (1045) as shown in FIG. 67*b*. This enables the desired CoP location at the next time step to be determined (step 1050). The desired CoP location at the next time step and the desired actuator position at the next time step are then sent to the actuators (step 1055). At the next time step the actuators will adjust towards this received actuator position (step 1060) and the received CoP location will be used to calculate the error at step 1020. Once the instruction is complete (all time steps have been completed) the next instruction is called (if there are anymore in the sequence) and the process is repeated for the new instruction's desired actuator length and CoP position. This method maintains the CoP of the WA and thus maintains the system in a balanced state.

Calculating Centre of Pressure

A preferred method for calculating the CoP of a foot will now be described with reference to flow chart 1100 of FIG. 68. To calculate the X and Y position of the CoP along the base of a foot (the base of the foot is considered the support polygon), four pressure sensors P1-P4 are used on the four corners of each foot as shown in the foot model 1200 of FIG. 69. The CoP is calculated using the geometrical properties of a triangle, where triangles are formed within larger triangles based on weighting factors that are expressed by pressures detected at the four corners.

Figure 68:
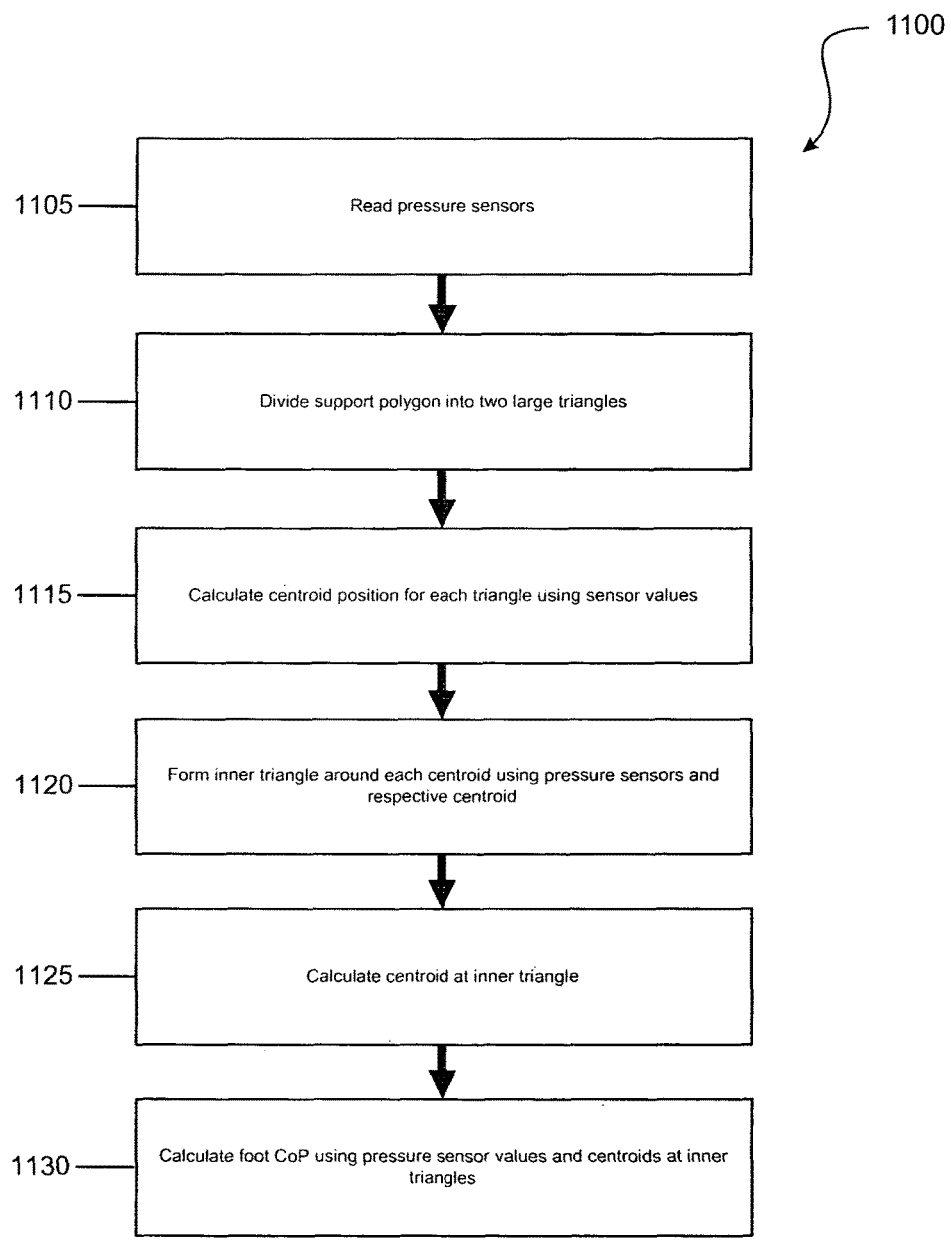
FIG. 68 shows a flow diagram of the sequence of operations performed by the balance subsystem when calculating the centre of pressure associated with a foot of the WA.
Figure 69:
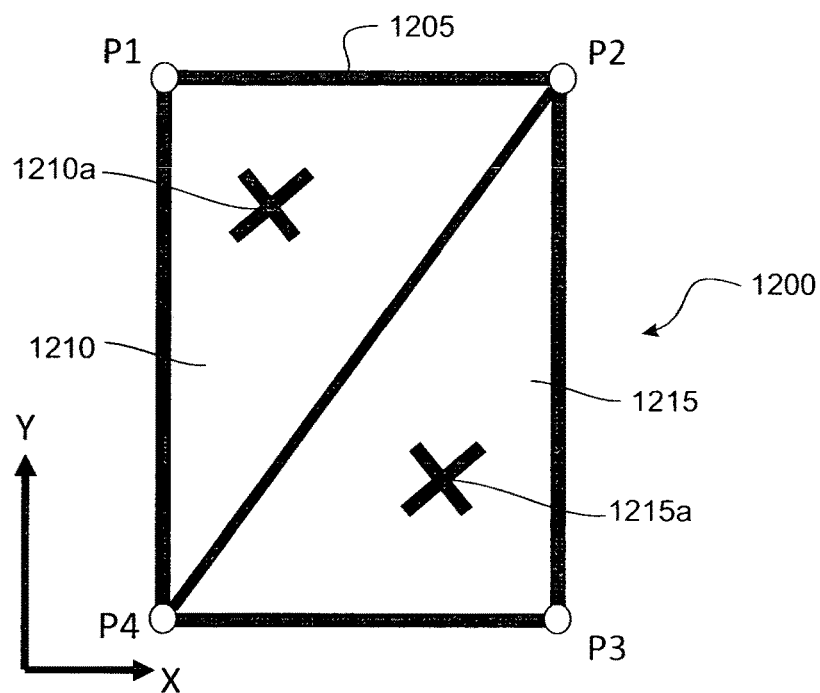
FIGS. 69-72 show an example of the process associated with calculating the centre of pressure of a foot as determined by the balance subsystem in accordance with a preferred form of the control system of the WA.

The rectangle 1205, being a representation of the WA's foot, is split into 2 large triangles 1210 and 1215, as depicted in FIG. 69 (step 1110 of FIG. 68). The centroid 1210*a* of triangle 1210 in the x-direction is calculated using equation 2.1 and the centroid 1210*a* of triangle 1210 in the y-direction is calculated using equation 2.2. Similarly the centroid 1215*a* of triangle 1215 in the x-direction is calculated using equation 2.3 and the centroid 1215*a* of triangle 1215 in the y-direction is calculated using equation 2.4 (step 1115 of FIG. 68).

$$CT1x = FCx - \left( \begin{array}{c} \left(\frac{2*P1}{PT1}\right)*(FCx - lP1x) + \\ \left(\frac{P2}{PT1}\right)*(FCx - lP2x) + \left(\frac{P4}{PT1}\right)*(FCx - lP4x) \end{array} \right) \quad (2.1)$$

$$CT1y = FCy - \left( \begin{array}{c} \left(\frac{2*P1}{PT1}\right)*(FCy - lP1y) + \\ \left(\frac{P2}{PT1}\right)*(FCy - lP2y) + \left(\frac{P4}{PT1}\right)*(FCy - lP4y) \end{array} \right) \quad (2.2)$$

$$CT2x = FCx - \left( \begin{array}{c} \left(\frac{P2}{PT2}\right)*(FCx - lP2x) + \\ \left(\frac{2*P3}{PT2}\right)*(FCx - lP3x) + \left(\frac{P4}{PT2}\right)*(FCx - lP4x) \end{array} \right) \quad (2.3)$$

$$CT2y = FCy - \left( \begin{array}{l} \left(\frac{P2}{PT2}\right)*(FCy - IP2y) + \\ \left(\frac{2*P3}{PT2}\right)*(FCy - IP3y) + \left(\frac{P4}{PT2}\right)*(FCy - IP4y) \end{array} \right) \quad (2.4)$$

Where:
CTnx=Centroid of large triangle n in the x-direction; for n=1,2
CTny=Centroid of large triangle n in the y-direction; for n=1,2
FCx=Centroid of foot in the x-direction
FCy=Centroid of foot in the y-direction
Pn=pressure reading from sensor Pn; for n=1,2,3,4
PT1=P1+P2+P4
PT2=P2+P3+P4
IPnx=x-co-ordinate of pressure sensor Pn, for n=1,2,3,4
IPny=y-co-ordinate of pressure sensor Pn, for n=1,2,3,4

Figure 70:
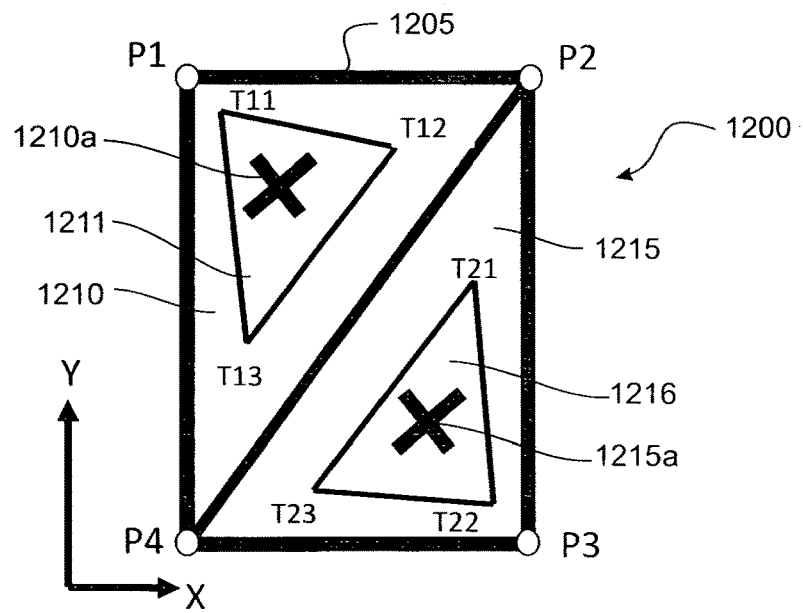

A smaller triangle 1211, 1216 is then formed around the centroid of the larger triangle 1210, 1215, as depicted in FIG. 70 (step 1120 of FIG. 68). The coordinates of the smaller triangles 1211 and 1216 are found using the weighting of respective pressure sensors over the total pressure on the foot and the distance between the centroid of the larger triangle and the respective corner of the foot. The X co-ordinates of the vertices which make up the inner triangles T11, T12, T13, T21, T22, T23 are calculated via equations 2.5-2.10 respectively; While the Y co-ordinates of the vertices which make up the inner triangles T11, T12, T13, T21, T22, T23 are calculated via equations 2.11-2.16 respectively.

$$T11x = CT1x - \left(\left(\frac{P1}{PT1}\right)*(CT1x - IP1x)\right)*2 \quad (2.5)$$

$$T12x = CT1x - \left(\left(\frac{P2}{PT1}\right)*(CT1x - IP2x)\right) \quad (2.6)$$

$$T13x = CT1x - \left(\left(\frac{P4}{PT1}\right)*(CT1x - IP3x)\right) \quad (2.7)$$

$$T21x = CT2x - \left(\left(\frac{P2}{PT1}\right)*(CT2x - IP2x)\right) \quad (2.8)$$

$$T22x = CT2x - \left(\left(\frac{P3}{PT1}\right)*(CT2x - IP3x)\right)*2 \quad (2.9)$$

$$T23x = CT2x - \left(\left(\frac{P4}{PT1}\right)*(CT2x - IP4x)\right) \quad (2.10)$$

$$T11y = CT1y - \left(\left(\frac{P1}{PT1}\right)*(CT1y - IP1y)\right)*2 \quad (2.11)$$

$$T12y = CT1y - \left(\left(\frac{P2}{PT1}\right)*(CT1y - IP2y)\right) \quad (2.12)$$

$$T13y = CT1y - \left(\left(\frac{P4}{PT1}\right)*(CT1y - IP3y)\right) \quad (2.13)$$

$$T21y = CT2y - \left(\left(\frac{P2}{PT1}\right)*(CT2y - IP2y)\right) \quad (2.14)$$

$$T22y = CT2y - \left(\left(\frac{P3}{PT1}\right)*(CT2y - IP3y)\right)*2 \quad (2.15)$$

$$T23y = CT2y - \left(\left(\frac{P4}{PT1}\right)*(CT2y - IP4y)\right) \quad (2.16)$$

Figure 71:
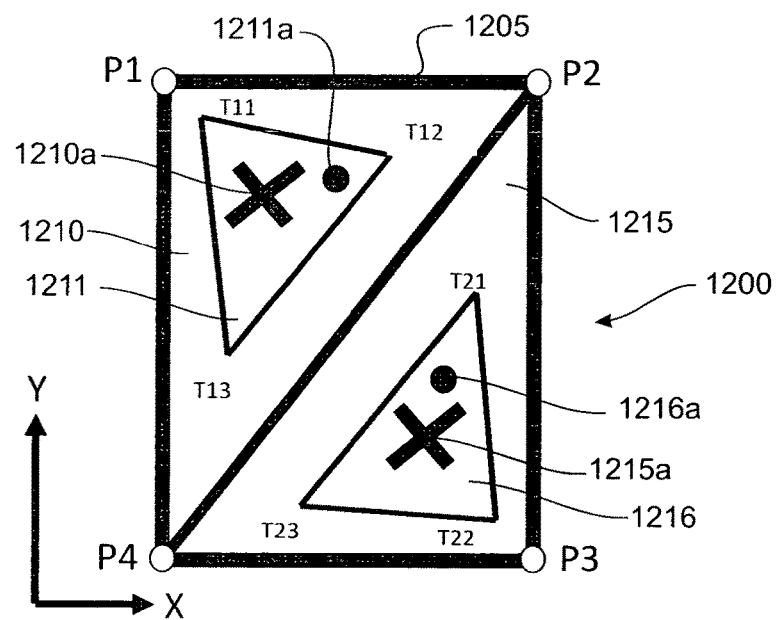

The centroids 1211a and 1216a of the inner triangles 1211 and 1216 are then calculated (step 1125 of FIG. 68) based on a factor which is weighted by the pressures present at the corners of the triangle and the distance between the centre of the two triangles (centre of foot) and the centroid 1211a and 1216a of the inner triangles. This is illustrated in FIG. 71. The X co-ordinates of the centroids 1211a and 1216a of inner triangle 1211 and inner triangle 1216 are calculated using equations 2.17 and 2.18 respectively. The Y co-ordinates of the centroids of inner triangle 1211 and inner triangle 1216 are calculated using equations 2.19 and 2.20 respectively.

$$CiT1x = CT1x - \left( \begin{array}{l} \left(\frac{2.25*P1}{PT1}\right)*(CT1x - T11x) + \\ \left(\frac{P2}{PT1}\right)*(CT1x - T12x) + \\ \left(\frac{P4}{PT1}\right)*(CT1x - T13x) \end{array} \right) \quad (2.17)$$

$$CiT1y = CT1y - \left( \begin{array}{l} \left(\frac{2.25*P1}{PT1}\right)*(CT1y - T11y) + \\ \left(\frac{P2}{PT1}\right)*(CT1y - T12y) + \\ \left(\frac{P4}{PT1}\right)*(CT1y - T13y) \end{array} \right) \quad (2.18)$$

$$CiT2x = CT2x - \left( \begin{array}{l} \left(\frac{P2}{PT2}\right)*(CT2x - T21x) + \\ \left(\frac{2.25*P3}{PT2}\right)*(CT2x - T22x) + \\ \left(\frac{P4}{PT2}\right)*(CT2x - T23x) \end{array} \right) \quad (2.19)$$

$$CiT2y = CT2y - \left( \begin{array}{l} \left(\frac{P2}{PT2}\right)*(CT2y - T21y) + \\ \left(\frac{2.25*P3}{PT2}\right)*(CT2y - T22y) + \\ \left(\frac{P4}{PT2}\right)*(CT2y - T23y) \end{array} \right) \quad (2.20)$$

Figure 72:
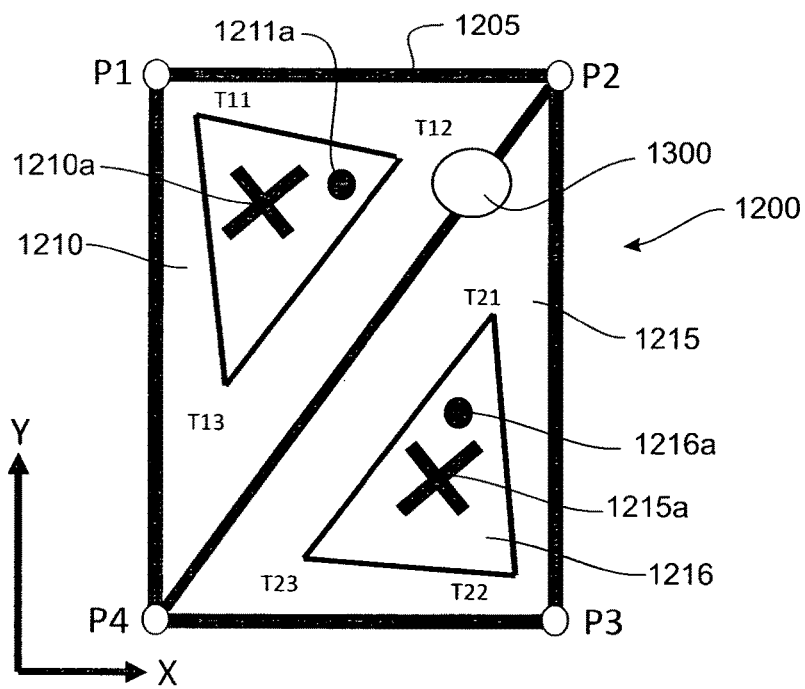

FIG. 72 finally illustrates the CoP 1300 of the foot. The X and Y co-ordinates (CoP_X and CoP_Y) of the CoP 1300 are calculated using the X and Y coordinates of centroids 1211a and 1216a of the inner triangles as applied in equations 2.21 and 2.22 respectively (step 1130 of FIG. 68).

$$CoP\_X = FCx - \left( \begin{array}{l} \left(\frac{PT1}{PT1+PT2}\right)*(FCx - CiT1x) + \\ \left(\frac{PT2}{PT1+PT2}\right)*(FCx - CiT2x) \end{array} \right) \quad (2.21)$$

$$CoP\_Y = FCY - \left( \begin{array}{l} \left(\frac{PT1}{PT1+PT2}\right)*(FCy - CiT1y) + \\ \left(\frac{PT2}{PT1+PT2}\right)*(FCy - CiT2y) \end{array} \right) \quad (2.22)$$

Other Inputs—Pressure Pads

Seat Sensors—There are two sensors in the rear of the WA, one in each "thigh" region. When the user activates the SIT or STAND function these sensors are activated. When activated in the sit function these sensors will determine when the user's weight has been transferred to the seat and cause the sit function to end. When activated in the stand function these sensors will determine when the user's weight is no longer supported by the seat so that it can continue with the stand function The foregoing description of the invention includes preferred forms thereof. Modifications may be made thereto without departing from the scope of the invention as defined by the accompanying claims.

The invention claimed is:

1. A method for controlling an exoskeleton worn by a user and having one or more actuators associated with various body members of the exoskeleton each corresponding to a body part of the user, the method comprising the steps of:
receiving input data indicative of a desired movement sequence;
obtaining from memory pre-programmed movement data indicative of one or more sequential instructions comprising at least a landing foot instruction, the sequential instructions being required to effect the movement sequence, each instruction being associated with relative actuator movements for performing the instruction;
moving the one or more actuators according to the relative actuator movements for each instruction;
sensing contact of a landing foot member with terrain with at least one contact sensor;
receiving data indicative of a change in terrain slope based on the sensed contact of the landing foot member and the terrain; and
adjusting the landing foot instruction based upon the received data indicative of the change in terrain slope, the step of adjusting comprising:
moving one or more of the actuators that are associated with the landing foot member of the exoskeleton to pivot the landing foot member towards a maximum allowable slope angle; and
terminating movement of the one or more actuators associated with the landing foot member upon receiving input indicative of alignment of the landing foot member with the terrain slope;
wherein an underside of the landing foot member comprises at least four corner regions and at least one of said contact sensor in each of the at least four corner regions;
wherein a terrain sub-system configured to adjust the landing foot instruction is triggered in the event that at least one but not all of said contact sensors sense contact of the underside of the landing foot member with the terrain, thereby providing said data indicative of the change in terrain slope; and
wherein the terrain sub-system is configured to perform the step of adjusting the landing foot instruction when one corner region is sensed to be in contact with the terrain by at least one of said contact sensor.

2. A method according to claim 1 wherein each contact sensor is a tactile sensor.

3. A method according to claim 1 wherein each contact sensor is a pressure sensor.

4. A method according to claim 1 wherein the data indicative of the change in terrain slope indicates a change in a longitudinal component of the terrain slope or a change in a transverse component of the terrain slope or both.

5. A method according to claim 4 wherein the maximum allowable slope angle is either a maximum allowable angle between the slope and a longitudinally extending and substantially horizontal line, or a maximum allowable transverse angle between the slope and a transversely extending and substantially horizontal line.

6. A method according to claim 5 wherein said at least four corner regions with contact sensors form two pairs of corner regions aligned in a transverse direction and two pairs of corner regions aligned in a longitudinal direction, and wherein receiving a trigger signal from at least one contact sensor located in only one of the two pairs of transversely aligned corner regions indicates a change in the longitudinal component of the terrain slope, and receiving a trigger signal from at least one contact sensor located in only one of the two pairs of longitudinally aligned corner regions indicates a change in the transverse component of the terrain slope.

7. A method according to claim 6 wherein the step of moving one or more of the actuators that are associated with the landing foot member of the exoskeleton to pivot the landing foot member towards a maximum allowable slope angle comprises pivoting the landing foot member about an axis traversing through one of said pairs of transversely aligned corner regions or longitudinally aligned corner regions from which a trigger signal is received.

8. A method according to claim 7 wherein the step of terminating movement of the one or more actuators comprises terminating the movement upon receiving a new trigger signal from at least one contact sensor not belonging to said one of said pairs of transversely aligned corner regions or longitudinally aligned corner regions from which said trigger signal is received, the new trigger signal indicating alignment of the landing foot member with the slope of the terrain.

9. A method according to claim 1 wherein the maximum allowable slope angle is predetermined and stored in memory.

10. A method according to claim 1 wherein the method further comprises after the step of terminating movement of the one or more actuators, performing a step of storing terrain state data indicative of a current slope of the terrain.

11. A method according to claim 10 wherein the step of storing terrain state data indicative of a current slope of the terrain comprises:
averaging an angle of the landing foot member and input data from an accelerometer associated with the landing foot member; and
storing the averaged angle as the data indicative of the current slope of the terrain.

12. A method according to claim 10 wherein the relative actuator movements are derived from the stored terrain state data indicative of the slope of the terrain during a previous movement sequence.

13. A method according to claim 1 wherein moving each actuator comprises changing a length of the actuator and wherein changing the length of an actuator alters an angle of an associated joint formed between body members of the exoskeleton.

14. A method according to claim 13 wherein the step of moving the one or more actuators associated with the landing foot member to pivot the landing foot member towards a maximum allowable slope angle comprises the steps of:
identifying a pivot axis and a pivot direction required to align the landing foot member with the slope of the terrain;
determining the length of each actuator; and then obtaining from the length of each actuator the angle of the associated joint or joints;
calculating a relative position of a foot joint of the exoskeleton associated with the required pivot axis and pivot direction using the angle of the foot joint;
determining a desired position of the foot joint associated with the landing foot member required to effect a pivot of the landing foot member to the maximum allowable slope angle;

using inverse kinematics to determine a desired position of each joint affecting a position of the foot joint;

determining desired joint angles from the desired positions of the joints affecting the position of the foot joint;

determining a desired change in length of each actuator associated with each desired joint angle; and changing the length of each actuator associated with each desired joint angle towards the desired change in length of the actuator.

15. A method according to claim 1 wherein the landing foot member comprises middle region contact sensors for providing information regarding a state of contact of central front and central back regions of the landing foot member with the terrain to provide increased resolution as to the alignment of the foot member with the terrain.

16. A method according to claim 1 wherein the exoskeleton comprises:
   i) a rigid pelvic support member including a user securing arrangement for fastening a user to at least the pelvic support member to support said user operationally;
   ii) a first leg structure and a second leg structure, each of the first leg structure and the second leg structure being coupled to and extending from said pelvic support member for operational location adjacent a respective leg of a user, each of the first leg structure and second leg structure comprising:
      an upper leg structural member for engagement with the upper leg of the user, the upper leg structural member being pivotally engaged at a first end thereof to the pelvic support member by a hip joint;
      a lower leg structural member for engagement with the lower leg of the user, the lower leg structural member being pivotally engaged at a first end thereof to a second end of the upper leg structural member by a knee joint;
      a foot member for engagement with the foot of a user, the foot member being pivotally engaged to a second end of the lower leg member by a foot joint;
      a main hip actuator configured for actuating rotation of said upper leg structural member relative to said pelvic support member about said hip joint, to in use pivot the upper leg structural member in an anterior/posterior plane;
      a knee actuator configured for actuating rotation of said lower leg structural member relative said upper leg structural member about said knee joint; and
      a main foot actuator configured for actuating rotation of said foot member relative said lower leg structural member about said foot joint about an axis of rotation substantially parallel to the axis of rotation of the knee joint; and
   iii) a power source configurable for providing power to at least one or more of the actuators selected from said main hip actuators, knee actuators, and main foot actuators.

17. A method according to claim 1 wherein the terrain sub-system is further configured to perform the step of adjusting the landing foot instruction when any number of corner regions fewer than all corner regions are sensed to be in contact with the terrain.

18. A method for controlling an exoskeleton worn by a user and having one or more actuators associated with various body members of the exoskeleton each corresponding to a body part of the user, the method comprising the steps of:

receiving input data indicative of a desired movement sequence;

obtaining from memory pre-programmed movement data indicative of one or more sequential instructions required to effect the movement sequence, said sequential instructions comprising at least a landing foot instruction to control the placement of a landing foot onto terrain supporting the exoskeleton, wherein each instruction being associated with relative actuator movements for performing the instruction;

updating the relative actuator movements according to stored adjustment data indicative of a current terrain state;

moving the one or more actuators according to the updated relative actuator movements for each instruction;

sensing contact of the landing foot with terrain with at least one contact sensor;

receiving data indicative of a change in terrain state during the execution of the landing foot instruction based on the sensed contact of the landing foot and the terrain during the execution of the landing foot instruction;

moving the one or more actuators to determine a current terrain state; and updating the adjustment data indicative of the change in terrain state;

wherein an underside of the landing foot comprises at least four corner regions and at least one of said contact sensor in each of the at least four corner regions;

wherein a terrain sub-system configured to adjust the landing foot instruction is triggered in the event that at least one but not all of said contact sensors sense contact of the underside of the landing foot with the terrain, thereby providing said data indicative of the change in terrain slope; and wherein the terrain sub-system is configured to adjust the landing foot instruction when one corner region is sensed to be in contact with the terrain by at least one of said contact sensor.

19. A method according to claim 18 wherein the terrain sub-system is further configured to adjust the landing foot instruction when any number of corner regions fewer than all corner regions are sensed to be in contact with the terrain.

20. A method for controlling an exoskeleton worn by a user and having one or more actuators associated with at least a foot member of the exoskeleton corresponding to a foot of the user to adjust the foot member to a change in terrain slope, the method comprising the steps of:

sensing contact of the foot member with terrain with at least one contact sensor during execution of a landing instruction associated with the foot member;

receiving data indicative of a change in terrain slope during the execution of the landing instruction based on the sensed contact of the foot member and the terrain during the execution of the landing instruction;

moving one or more of the actuators that are associated with the foot member to pivot the foot member towards a maximum allowable slope angle; and terminating movement of the one or more actuators associated with the foot member upon receiving input indicative of alignment of the foot member with the slope;

wherein an underside of the foot member comprises at least four corner regions and at least one of said contact sensor in each of the at least four corner regions;

wherein a terrain sub-system configured to adjust the landing instruction is triggered in the event that at least one but not all of said contact sensors sense contact of the underside of the foot member with the terrain, thereby providing said data indicative of the change in terrain slope; and wherein the terrain sub-system is configured to adjust the landing instruction when one corner region is sensed to be in contact with the terrain by at least one of said contact sensor.

21. A method according to claim 19 wherein the terrain sub-system is further configured to adjust the landing instruction when any number of corner regions fewer than all corner regions are sensed to be in contact with the terrain.

22. A control system for controlling an exoskeleton worn by a user and having one or more actuators associated with various body members of the exoskeleton each corresponding to a body part of the user, the control system comprising:
 a user interface for receiving input data indicative of a desired movement sequence;
 a memory component for storing pre-programmed movement data indicative of one or more sequential instructions comprising at least a landing foot instruction, the one or more sequential instructions required to effect the movement sequence, each instruction being associated with relative actuator movements for performing the instruction;
 an actuator controller for moving the one or more actuators according to the relative actuator movements for each instruction; and
 a terrain sub-system for receiving a sensor output from at least one contact sensor indicative of a terrain state during the execution of the landing foot instruction and adjusting the actuator movements based upon a detected change in terrain state during the execution of the landing foot instruction;
 wherein an underside of a landing foot member comprises at least four corner regions and at least one of said contact sensor in each of the at least four corner regions;
 wherein the terrain sub-system is configured to adjust the landing foot instruction and is triggered in the event that at least one but not all of said contact sensors sense contact of the underside of the landing foot member with the terrain, thereby providing said data indicative of the terrain state; and
 wherein the terrain sub-system is configured to adjust the landing foot instruction when one corner region is sensed to be in contact with the terrain by at least one of said contact sensor.

23. A method according to claim 22 wherein the terrain sub-system is further configured to adjust the landing foot instruction when any number of corner regions fewer than all corner regions are sensed to be in contact with the terrain.

* * * * *